(12) United States Patent
Szpirer

(10) Patent No.: US 9,920,323 B2
(45) Date of Patent: Mar. 20, 2018

(54) GENETICALLY MODIFIED PHAGE AND USE THEREOF

(75) Inventor: Cedric Szpirer, Fleurus (BE)

(73) Assignee: DELPHI GENETICS, Charleroi (BE)

(*) Notice: Subject to any disclaimer, the term of this patent is extended or adjusted under 35 U.S.C. 154(b) by 395 days.

(21) Appl. No.: 13/178,402

(22) Filed: Jul. 7, 2011

(65) Prior Publication Data

US 2013/0011898 A1   Jan. 10, 2013

(51) Int. Cl.
| | | |
|---|---|---|
| *A61K 35/74* | (2015.01) | |
| *C12N 15/70* | (2006.01) | |
| *C12N 7/00* | (2006.01) | |
| *C12P 1/04* | (2006.01) | |

(52) U.S. Cl.
CPC .......... *C12N 15/70* (2013.01); *C12N 7/00* (2013.01); *C12P 1/04* (2013.01); *C12N 2795/10351* (2013.01); *C12N 2795/10352* (2013.01)

(58) Field of Classification Search
None
See application file for complete search history.

(56) References Cited

U.S. PATENT DOCUMENTS

| | | | |
|---|---|---|---|
| 4,952,496 A | 8/1990 | Studier et al. | 435/91.41 |
| 8,153,119 B2* | 4/2012 | Collins et al. | 424/93.6 |
| 2002/0090678 A1 | 7/2002 | Kordyum et al. | 435/69.1 |
| 2003/0003472 A1 | 1/2003 | Cox et al. | |
| 2004/0115811 A1 | 6/2004 | Gabant | |

FOREIGN PATENT DOCUMENTS

| | | |
|---|---|---|
| WO | 01/004288 | 1/2001 |
| WO | WO 2003/050240 | 6/2003 |
| WO | WO 2006/091483 | 8/2006 |
| WO | WO 2008/139153 | 11/2008 |

OTHER PUBLICATIONS

Tabor et al. (PNAS, vol. 82, pp. 1074-1078, 1985).*
Mount et al. (Virology, vol. 35, iss. 1, 1968, p. 1340-1349).*
Borysowski et al. (Exp. Bio. & Medicine, 2006, pp. 366-377).*
Xu et al. (PNAS, vol. 2004, vol. 101, pags 6415-6420).*
Blasi et al. (Molecular Microbiology, 1996, vol. 21 (4), pp. 675-682).*
Loessner (Current Opinion in Microbio., 2005, vol. 8, pp. 480-487).*
Zink et al. (Microbiol., 1995, vol. 141, 2577-2584).*
Vukov et al. (Mol. Microbiol. 2003, vol. 48(1), pp. 173-186).*
Loessner et al. (FEMS Microbiol. Letters, vol. 162, 1998, pp. 265-274).*
Loessner et al. (Molecular Microbiol., 1995, vol. 16(6), pp. 1231-1241).*
Cronan (J of Bact., vol. 185, No. 22, Nov. 2003, pp. 6522-6529).*
Wang et al. (Annu. Rev. Microbiol., 2000, vol. 54, pp. 799-825).*
Tabor (Current Protocols in Mol. Bio., 1990, pp. 16.2.1-16.2.11).*
"Enterobacteria phage DE3", Accession No. EU097592, EMBL Database, published Aug. 2, 2007.
Christensen, "Bacteriophage lambda-based expression vectors," *Molecular Biotechnology*, 17:219-224, 2001.
Lin et al., "Characterization of bacteriophage λ Q-mutant for stable and efficient production of recombinant protein in *Escherichia coli* system," *Biotechnology and Bioengineering*, 57(5):529-535, 1998.
Padukone et al., "λ Vectors for stable cloned gene expression," *Biotechnol. Prog.*, 6:277-282, 1990.
Phue et al., Modified *Escherichia coli* B (BL21), a superior producer of plasmid DNA compared with *Escherichia coli* K (DH5alpha), Biotechnology and Bioengineering, 101, 831-836, 2008.
Makrides et al., Strategies for achieving high-level expression of genes in *Escherichia coli*, Microbiological Reviews, 1996, (60)3:512-538.
Guzman et al., Tight regulation, modulation, and high-level expression by vectors containing the arabinose PBAD promoter, J Bacteriol. Jul. 1995;177(14):4121-30.
Poo et al., Novel high-level constitutive expression system, pHCE vector, for a convenient and cost-effective soluble production of human tumor necrosis factor-α, Biotechnology Letters, 2002, 24:1185-1189.
Jeong et al., Constitutive production of human leptin by fed-batch culture of recombinant rpoS-*Escherichia coli*, Protein expression and purification, 2004, 36:150-156.
Andersen and Reilly, Production technologies for monoclonal antibodies and their fragments, Current Opinion in Biotechnology, 2004, 15:456-462.
Hollinger and Hudson, Engineered antibody fragments and the rise of single domains, Nature Biotechnology, 2005 (23)9: 1126-1136.
Datsenko and Wanner One-step inactivation of chromosomal genes in *Escherichia coli* K-12 using PCR products, PNAS 97(12), 6640-6645, 2000.
Pierce et al., A positive selection vector for cloning high molecular weight DNA by the bacteriophage P1 system: improved cloning efficacy, Proc. Natl. Acad. Sci., vol. 89(6)(1992) p. 2056-2060.
Heinrich et al., Use of the lysis gene of bacteriophage phi X174 for the construction of a positive selection vector, Gene, vol. 42 n[deg.]3 (1986) p. 345-349.
Trudel et al., pGATA: a positive selection vector based on the toxicity of the transcription factor GATA-1 to bacteria, Biotechniques 1996, vol. 20(4), p. 684-693.
Schlieper et al., A positive selection vector for cloning of long polymerase chain reaction fragments based on a lethal mutant of the crp gene of *Escherichia coli*, Anal. Biochem. 1998, vol. 257(2), p. 203-209.
Studier and Moffat, Use of bacteriophage T7 RNA polymerase to direct selective high-level expression of cloned genes, Journal of Molecular Biology, 1986, 189:113-130.
Haldimann and Wanner, Conditional-replication, integration, excision, and retrieval plasmid-host systems for gene structure-function studies of bacteria, Journal of Bacteriology, 183, 6384-6393, 2001).
Warming et al., Simple and highly efficient BAC recombineering using galK selection, Nucleic acid research, 2005, 33(4).
ISR of the PCT patent application PCT/EP2012/063244.

(Continued)

*Primary Examiner* — Hope Robinson
(74) *Attorney, Agent, or Firm* — Norton Rose Fulbright US LLP

(57) ABSTRACT

The present invention relates to a genetically modified phage and use thereof in a method for producing a biomolecule of interest.

15 Claims, 1 Drawing Sheet

(56) References Cited

OTHER PUBLICATIONS

Miao et al, "Characterization of gene expression in recombinant *Escherichia coli* cells infected with phage lambda" Biotechnol. Prog. 1993, 9(2):153-159.
Sternberg, "A characterization of bacteriophage P1 DNA fragments cloned in a lambda vector" Virology, 1979, 96(1):129-142.
Cho et al, "Interactions between integrase and excisionase in the phage lambda excisive nucleoprotein complex." J Bacteriol. Sep. 2001; 184(18):5200-3.
Abremski, Gottesman, "Purification of the bacteriophage lambda xis gene product is required for lambda excisive recombination"; J Biol Chem, 1982, 257(16), 9658-62.
Dorgai et al., "Recognition of core binding sites by bacteriophage integrases". J Mol Biol. Apr. 17, 1998;277(5):1059-70.
Herskowitz, "Control of gene expression in bacteriophage lambda". Annu Rev Genet. 1973;7:289-324.

\* cited by examiner

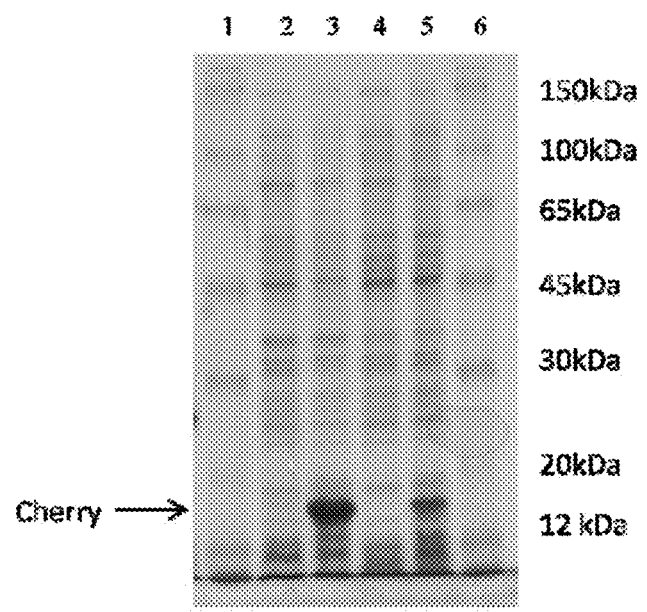

SEQUENCE LISTING

<160> NUMBER OF SEQ ID NOS: 35

<210> SEQ ID NO 1
<211> LENGTH: 324
<212> TYPE: DNA

<213> ORGANISM: Unknown
<220> FEATURE:
<223> OTHER INFORMATION: Enterobacteria phage lambda

<400> SEQUENCE: 1

| | | | | | | |
|---|---|---|---|---|---|---|
| atgaagatgc | cagaaaaaca | tgacctgttg | gccgccattc | tcgcggcaaa | ggaacaaggc | 60 |
| atcgggggcaa | tccttgcgtt | tgcaatggcg | taccttcgcg | gcagatataa | tggcggtgcg | 120 |
| tttacaaaaa | cagtaatcga | cgcaacgatg | tgcgccatta | tcgcctggtt | cattcgtgac | 180 |
| cttctcgact | tcgccggact | aagtagcaat | ctcgcttata | taacgagcgt | gtttatcggc | 240 |
| tacatcggta | ctgactcgat | tggttcgctt | atcaaacgct | tcgctgctaa | aaaagccgga | 300 |
| gtagaagatg | gtagaaatca | ataa | | | | 324 |

<210> SEQ ID NO 2
<211> LENGTH: 477
<212> TYPE: DNA
<213> ORGANISM: Unknown
<220> FEATURE:
<223> OTHER INFORMATION: Enterobacteria phage lambda

<400> SEQUENCE: 2

| | | | | | | |
|---|---|---|---|---|---|---|
| atggtagaaa | tcaataatca | acgtaaggcg | ttcctcgata | tgctggcgtg | gtcggaggga | 60 |
| actgataacg | gacgtcagaa | aaccagaaat | catggttatg | acgtcattgt | aggcggagag | 120 |
| ctattcactg | attactccga | tcaccctcgc | aaacttgtca | cgctaaaccc | aaaactcaaa | 180 |
| tcaacaggcg | ccggacgcta | ccagcttctt | tcccgttggt | gggatgccta | ccgcaagcag | 240 |
| cttggcctga | aagacttctc | tccgaaaagt | caggacgctg | tggcattgca | gcagattaag | 300 |
| gagcgtggcg | ctttacctat | gattgatcgt | ggtgatatcc | gtcaggcaat | cgaccgttgc | 360 |
| agcaatatct | gggcttcact | gccgggcgct | ggttatggtc | agttcgagca | taaggctgac | 420 |
| agcctgattg | caaaattcaa | agaagcgggc | ggaacggtca | gagagattga | tgtatga | 477 |

<210> SEQ ID NO 3
<211> LENGTH: 462
<212> TYPE: DNA
<213> ORGANISM: Unknown
<220> FEATURE:
<223> OTHER INFORMATION: Enterobacteria phage lambda

<400> SEQUENCE: 3

| | | | | | | |
|---|---|---|---|---|---|---|
| atgagcagag | tcaccgcgat | tatctccgct | ctggttatct | gcatcatcgt | ctgcctgtca | 60 |
| tgggctgtta | atcattaccg | tgataacgcc | attacctaca | aagcccagcg | cgacaaaaat | 120 |
| gccagagaac | tgaagctggc | gaacgcggca | attactgaca | tgcagatgcg | tcagcgtgat | 180 |
| gttgctgcgc | tcgatgcaaa | atacacgaag | gagttagctg | atgctaaagc | tgaaaatgat | 240 |
| gctctgcgtg | atgatgttgc | cgctggtcgt | cgtcggttgc | acatcaaagc | agtctgtcag | 300 |
| tcagtgcgtg | aagccaccac | cgcctccggc | gtggataatg | cagcctcccc | ccgactggca | 360 |
| gacaccgctg | aacgggatta | tttcaccctc | agagagaggc | tgatcactat | gcaaaaacaa | 420 |
| ctggaaggaa | cccagaagta | tattaatgag | cagtgcagat | ag | | 462 |

<210> SEQ ID NO 4
<211> LENGTH: 201
<212> TYPE: DNA
<213> ORGANISM: Unknown
<220> FEATURE:
<223> OTHER INFORMATION: Enterobacteria phage lambda

<400> SEQUENCE: 4

```
atgactacga ctattgataa aaatcaatgg tgtggacaat tcaagcgatg caatggatgc    60
aagctgcaat cggaatgcat ggttaagcct gaagaaatgt ttcctgtaat ggaagatggg   120
aaatatgtcg ataaatgggc aatacgaacg acggcaatga ttgccagaga acttggtaaa   180
cagaacaaca aagctgcctg a                                              201

<210> SEQ ID NO 5
<211> LENGTH: 300
<212> TYPE: DNA
<213> ORGANISM: Unknown
<220> FEATURE:
<223> OTHER INFORMATION: Enterobacteria phage lambda

<400> SEQUENCE: 5
atggtaacca ttgtctggaa agaatccaaa ggtacggcaa aaagccgcta caaagctcgc    60
agagcagaac ttattgccga gcgacgcagt aatgaagcac tggcgcgaaa aattgcgcta   120
aagctctctg gttgcgtcag agcagataaa gcagcatcac tcggaagcct tcgctgcaag   180
aaggcagaag aagtcgagcg taaacagaac cgtatttact acagcaagcc acgcagtgaa   240
atgggtgtga cttgtgttgg tcgccagaaa attaaattag gcagcaaacc acttatttga   300

<210> SEQ ID NO 6
<211> LENGTH: 651
<212> TYPE: DNA
<213> ORGANISM: Unknown
<220> FEATURE:
<223> OTHER INFORMATION: Enterobacteria phage lambda

<400> SEQUENCE: 6
atgaatacac aactgatggg tgagcgtatt cgcgctcgca gaaaagaact caagattagg    60
caggctgccc ttggcaagat ggttggcgtg tctaatgttg ctatttccca atgggagcga   120
tctgaaactg agcccaatgg cgaaaaccta ttggccttag ccaaggcttt gcagtgctcc   180
cctgattacc tgttgaaagg agaggatagt ctttcaaaca ttgcctatca cagcaggcat   240
gatccaagag gttcgtatcc tctaattagt tgggtaagcg caggatgttg gatgaaagct   300
gtagagccat atcataggcg tgcaatagat aactggtacg acacaacggt agattgttct   360
gaagactctt tttggctcga cgttaaaggc gattcaatga ctgccccggc aggactgagt   420
attcctgagg ggatgattat tctcgtcgac ccagaagtcg aaccacgtaa tggaaagctg   480
gtagtcgcca aacttgaagg agaaaacgag gcgacattca aaagttagt tattgatgcc   540 ggtagaaaat tcctgaaacc actcaatcca caatacccaa tgattgaaat caatgggaac   600
tgtaaaatca ttggcgttgt cgttgatgcc aagctagcaa accttcctta a            651

<210> SEQ ID NO 7
<211> LENGTH: 1071
<212> TYPE: DNA
<213> ORGANISM: Unknown
<220> FEATURE:
<223> OTHER INFORMATION: Enterobacteria phage lambda

<400> SEQUENCE: 7
atgggaagaa ggcgaagtca tgagcgccgg gatttacccc ctaacccttta tataagaaac    60 aatggatatt actgctacag ggacccaagg acgggtaaag agtttggatt aggcagagac   120
aggcgaatcg caatcactga agctatacag gccaacattg agttattttc aggacacaaa   180
cacaagcctc tgacagcgag aatcaacagt gataattccg ttacgttaca ttcatggctt   240
```

```
gatcgctacg aaaaaatcct ggccagcaga ggaatcaagc agaagacact cataaattac      300
atgagcaaaa ttaaagcaat aaggaggggt ctgcctgatg ctccacttga agacatcacc      360
acaaaagaaa ttgcggcaat gctcaatgga tacatagacg agggcaaggc ggcgtcagcc      420
aagttaatca gatcaacact gagcgatgca ttccgagagg caatagctga aggccatata      480
acaacaaacc atgtcgctgc cactcgcgca gcaaaatcag aggtaaggag atcaagactt      540
acggctgacg aatacctgaa aatttatcaa gcagcagaat catcaccatg ttggctcaga      600
cttgcaatgg aactggctgt tgttaccggg caacgagttg gtgatttatg cgaaatgaag      660
tggtctgata tcgtagatgg atatctttat gtcgagcaaa gcaaacagg cgtaaaaatt       720 gccatcccaa cagcattgca tattgatgct ctcggaatat caatgaagga aacacttgat      780
aaatgcaaag agattcttgg cggagaaacc ataattgcat ctactcgtcg cgaaccgctt      840
tcatccggca cagtatcaag gtattttatg cgcgcacgaa aagcatcagg tctttccttc      900 gaagggggatc cgcctacctt tcacgagttg cgcagtttgt ctgcaagact ctatgagaag      960
cagataagcg ataagtttgc tcaacatctt ctcgggcata agtcggacac catggcatca     1020
cagtatcgtg atgacagagg cagggagtgg gacaaaattg aaatcaaata a              1071

<210> SEQ ID NO 8
<211> LENGTH: 219
<212> TYPE: DNA
<213> ORGANISM: Unknown
<220> FEATURE:
<223> OTHER INFORMATION: Enterobacteria phage lambda

<400> SEQUENCE: 8
atgtacttga cacttcagga gtggaacgca cgccagcgac gtccaagaag ccttgaaaca       60
gttcgtcgat gggttcggga atgcaggata ttcccacctc cggttaagga tggaagagag      120
tatctgttcc acgaatcagc ggtaaaggtt gacttaaatc gaccagtaac aggtggcctt      180
ttgaagagga tcagaaatgg gaagaaggcg aagtcatga                             219

<210> SEQ ID NO 9
<211> LENGTH: 232
<212> TYPE: DNA
<213> ORGANISM: Unknown
<220> FEATURE:
<223> OTHER INFORMATION: Enterobacteria phage lambda

<400> SEQUENCE: 9
tacaggtcac taataccatc taagtagttg attcatagtg actgcatatg ttgtgtttta       60
cagtattatg tagtctgttt tttatgcaaa atctaattta atatattgat atttatatca      120
ttttacgttt ctcgttcagc ttttttatac taagttggca ttataaaaaa gcattgctta     180
tcaatttgtt gcaacgaaca ggtcactatc agtcaaaata aaatcattat tt              232

<210> SEQ ID NO 10
<211> LENGTH: 29865
<212> TYPE: DNA
<213> ORGANISM: Artificial Sequence
<220> FEATURE:
<223> OTHER INFORMATION: Synthetic primer

<400> SEQUENCE: 10
gcttttttat actaagttgg cattataaaa aagcattgct tatcaatttg ttgcaacgaa       60
caggtcacta tcagtcaaaa taaaatcatt atttgatttc aatttgtcc cactccctgc      120 ctctgtcatc acgatactgt gatgccatgg tgtccgactt atgcccgaga agatgttgag      180
```

```
caaacttatc gcttatctgc ttctcataga gtcttgcaga caaactgcgc aactcgtgaa    240
aggtaggcgg atccagatcc cggacaccat cgaatgcgc aaaacctttc gcggtatggc     300
atgatagcgc ccggaagaga gtcaattcag ggtggtgaat gtgaaaccag taacgttata    360
cgatgtcgca gagtatgccg gtgtctctta tcagaccgtt tcccgcgtgg tgaaccaggc    420
cagccacgtt tctgcgaaaa cgcgggaaaa agtggaagcg gcgatggcgg agctgaatta    480
cattcccaac cgcgtggcac aacaactggc gggcaaacag tcgttgctga ttggcgttgc    540
cacctccagt ctggccctgc acgcgccgtc gcaaattgtc gcggcgatta atctcgcgc    600 cgatcaactg ggtgccagcg tggtggtgtc gatggtagaa cgaagcggcg tcgaagcctg    660
taaagcggcg gtgcacaatc ttctcgcgca acgcgtcagt gggctgatca ttaactatcc    720
gctggatgac caggatgcca ttgctgtgga agctgcctgc actaatgttc cggcgttatt    780
tcttgatgtc tctgaccaga cacccatcaa cagtattatt ttctcccatg aagacggtac    840
gcgactgggc gtggagcatc tggtcgcatt gggtcaccag caaatcgcgc tgttagcggg    900
cccattaagt tctgtctcgg cgcgtctgcg tctggctggc tggcataaat atctcactcg    960
caatcaaatt cagccgatag cggaacggga aggcgactgg agtgccatgt ccggttttca   1020
acaaaccatg caaatgctga atgagggcat cgttcccact gcgatgctgg ttgccaacga   1080
tcagatggcg ctgggcgcaa tgcgcgccat taccgagtcc gggctgcgcg ttggtgcgga   1140
tatctcggta gtgggatacg acgataccga agacagctca tgttatatcc cgccgttaac   1200
caccatcaaa caggatttc gcctgctggg gcaaaccagc gtggaccgct tgctgcaact   1260
ctctcagggc caggcggtga agggcaatca gctgttgccc gtctcactgg tgaaaagaaa   1320
aaccaccctg gcgcccaata cgcaaaccgc ctctccccgc gcgttggccg attcattaat   1380
gcagctggca cgacaggttt cccgactgga aagcgggcag tgagcgcaac gcaattaatg   1440
taagttagct cactcattag caccccagg ctttacactt tatgcttccg gctcgtataa    1500
tgtgtggaat tgtgagcgga taacaatttc acacaggaaa cagctatgac catgattacg    1560
gattcactgg ccgtcgtttt acaacgtcgt gactgggaaa accctggcgt tacccaactt    1620
aatcgccttg cagcacatcc cccttcgcc agctggcgta atagcgaaga ggcccgcacc     1680
gatcgccctt cccaacagtt gcgcagcctg aatggcgaat ggcgctttgc ctggtttccg    1740
gcaccagaag cggtgccgga aagctggctg gagtgcgatc ttcctgaggc cgatactgtc    1800
gtcgtcccct caaactggca gatgcacggt tacgatgcgc ccatctacac caacgtgacc    1860
tatcccatta cggtcaatcc gccgtttgtt cccacggaga atccgacggg ttgttactcg    1920
ctcacattta atgttgatga aagctggcta caggaaggcc agacgcgaat tattttgat    1980 ggcgtcggga tctgatccgg atttactaac tggaagaggc actaaatgaa cacgattaac    2040
atcgctaaga acgacttctc tgacatcgaa ctggctgcta tcccgttcaa cactctggct    2100
gaccattacg gtgagcgttt agctcgcgaa cagttggccc ttgagcatga gtcttacgag    2160
atgggtgaag cacgcttccg caagatgttt gagcgtcaac ttaaagctgg tgaggttgcg    2220
gataacgctg ccgccaagcc tctcatcact accctactcc ctaagatgat tgcacgcatc    2280
aacgactggt ttgaggaagt gaaagctaag cgcggcaagc gcccgacagc cttccagttc    2340
ctgcaagaaa tcaagccgga agccgtagcg tacatcacca ttaagaccac tctggcttgc    2400
ctaaccagtg ctgacaatac aaccgttcag gctgtagcaa gcgcaatcgg tcgggccatt    2460
gaggacgagg ctcgcttcgg tcgtatccgt gaccttgaag ctaagcactt caagaaaaac    2520
```

-continued

| | |
|---|---|
| gttgaggaac aactcaacaa gcgcgtaggg cacgtctaca agaaagcatt tatgcaagtt | 2580 |
| gtcgaggctg acatgctctc taagggtcta ctcggtggcg aggcgtggtc ttcgtggcat | 2640 |
| aaggaagact ctattcatgt aggagtacgc tgcatcgaga tgctcattga gtcaaccgga | 2700 |
| atggttagct tacaccgcca aaatgctggc gtagtaggtc aagactctga gactatcgaa | 2760 |
| ctcgcacctg aatacgctga ggctatcgca acccgtgcag gtgcgctggc tggcatctct | 2820 |
| ccgatgttcc aaccttgcgt agttcctcct aagccgtgga ctggcattac tggtggtggc | 2880 |
| tattgggcta acggtcgtcg tcctctggcg ctggtgcgta ctcacagtaa gaaagcactg | 2940 |
| atgcgctacg aagacgttta catgcctgag gtgtacaaag cgattaacat tgcgcaaaac | 3000 |
| accgcatgga aaatcaacaa gaaagtccta gcggtcgcca acgtaatcac caagtggaag | 3060 |
| cattgtccgg tcgaggacat ccctgcgatt gagcgtgaag aactcccgat gaaaccggaa | 3120 |
| gacatcgaca tgaatcctga ggctctcacc gcgtggaaac gtgctgccgc tgctgtgtac | 3180 |
| cgcaaggaca aggctcgcaa gtctcgccgt atcagccttg agttcatgct tgagcaagcc | 3240 |
| aataagtttg ctaaccataa ggccatctgg ttcccttaca acatggactg gcgcggtcgt | 3300 |
| gtttacgctg tgtcaatgtt caacccgcaa ggtaacgata tgaccaaagg actgcttacg | 3360 |
| ctggcgaaag gtaaaccaat cggtaaggaa ggttactact ggctgaaaat ccacggtgca | 3420 |
| aactgtgcgg gtgtcgataa ggttccgttc cctgagcgca tcaagttcat tgaggaaaac | 3480 |
| cacgagaaca tcatggcttg cgctaagtct ccactggaga acacttggtg ggctgagcaa | 3540 |
| gattctccgt tctgcttcct tgcgttctgc tttgagtacg ctggggtaca gcaccacggc | 3600 |
| ctgagctata actgctccct tccgctggcg tttgacgggt cttgctctgg catccagcac | 3660 |
| ttctccgcga tgctccgaga tgaggtaggt ggtcgcgcgg ttaacttgct tcctagtgaa | 3720 |
| accgttcagg acatctacgg gattgttgct aagaaagtca acgagattct acaagcagac | 3780 |
| gcaatcaatg ggaccgataa cgaagtagtt accgtgaccg atgagaacac tggtgaaatc | 3840 |
| tctgagaaag tcaagctggg cactaaggca ctggctggtc aatggctggc ttacggtgtt | 3900 |
| actcgcagtg tgactaagcg ttcagtcatg acgctggctt acgggtccaa agagttcggc | 3960 |
| ttccgtcaac aagtgctgga agataccatt cagccagcta ttgattccgg caagggtctg | 4020 |
| atgttcactc agccgaatca ggctgctgga tacatggcta agctgatttg ggaatctgtg | 4080 |
| agcgtgacgg tggtagctgc ggttgaagca atgaactggc ttaagtctgc tgctaagctg | 4140 |
| ctggctgctg aggtcaaaga taagaagact ggagagattc ttcgcaagcg ttgcgctgtg | 4200 |
| cattgggtaa ctcctgatgg tttccctgtg tggcaggaat acaagaagcc tattcagacg | 4260 |
| cgcttgaacc tgatgttcct cggtcagttc cgcttacagc ctaccattaa caccaacaaa | 4320 |
| gatagcgaga ttgatgcaca caaacaggag tctggtatcg ctcctaactt tgtacacagc | 4380 |
| caagacggta gccaccttcg taagactgta gtgtgggcac acgagaagta cggaatcgaa | 4440 |
| tcttttgcac tgattcacga ctccttcggt accattccgg ctgacgctgc gaacctgttc | 4500 |
| aaagcagtgc gcgaaactat ggttgacaca tatgagtctt gtgatgtact ggctgatttc | 4560 |
| tacgaccagt tcgctgacca gttgcacgag tctcaattgg acaaaatgcc agcacttccg | 4620 |
| gctaaaggta acttgaacct ccgtgacatc ttagagtcgg acttcgcgtt cgcgtaacgc | 4680 |
| caaatcaata cgactccgga tccccttcga aggaaagacc tgatgctttt cgtgcgcgca | 4740 |
| taaaatacct tgatactgtg ccggatgaaa gcggttcgcg acgagtagat gcaattatgg | 4800 |
| tttctccgcc aagaatctct ttgcatttat caagtgtttc cttcattgat attccgagag | 4860 |
| catcaatatg caatgctgtt gggatggcaa tttttacgcc tgttttgctt tgctcgacat | 4920 |

```
aaagatatcc atctacgata tcagaccact tcatttcgca taaatcacca actcgttgcc    4980
cggtaacaac agccagttcc attgcaagtc tgagccaaca tggtgatgat tctgctgctt    5040
gataaatttt caggtattcg tcagccgtaa gtcttgatct ccttacctct gattttgctg    5100
cgcgagtggc agcgacatgg tttgttgtta tatggccttc agctattgcc tctcggaatg    5160
catcgctcag tgttgatctg attaacttgg ctgacgccgc cttgccctcg tctatgtatc    5220
cattgagcat tgccgcaatt tcttttgtgg tgatgtcttc aagtggagca tcaggcagac    5280
ccctccttat tgctttaatt ttgctcatgt aatttatgag tgtcttctgc ttgattcctc    5340
tgctggccag gattttttcg tagcgatcaa gccatgaatg taacgtaacg gaattatcac    5400
tgttgattct cgctgtcaga ggcttgtgtt tgtgtcctga aaataactca atgttggcct    5460
gtatagcttc agtgattgcg attcgcctgt ctctgcctaa tccaaactct ttacccgtcc    5520
ttgggtccct gtagcagtaa tatccattgt ttcttatata aaggttaggg ggtaaatccc    5580
ggcgctcatg acttcgcctt cttcacactg gagggcaaag aagatttcca ataatcagaa    5640
caagtcggct cctgtttagt tacgagcgac attgctccgt gtattcactc gttggaatga    5700
atacacagtg cagtgtttat tctgttattt atgccaaaaa taaaggccac tatcaggcag    5760 cttttgttgtt ctgtttacca agttctctgg caatcattgc cgtcgttcgt attgcccatt    5820
tatcgacata tttcccatct tccattacag gaaacatttc ttcaggctta accatgcatt    5880
ccgattgcag cttgcatcca ttgcatcgct tgaattgtcc acaccattga ttttatcaa     5940 tagtcgtagt catacggata gtcctggtat tgttccatca catcctgagg atgctcttcg    6000
aactcttcaa attcttcttc catatatcac ctcaaataag tggtttgctg cctaatttaa    6060
ttttctggcg accaacacaa gtcacaccca tttcactgcg tggcttgctg tagtaaatac    6120
ggttctgttt acgctcgact tcttctgcct tcttgcagcg aaggcttccg agtgatgctg    6180
ctttatctgc tctgacgcaa ccagagagct ttagcgcaat ttttcgcgcc agtgcttcat    6240
tactgcgtcg ctcggcaata agttctgctc tgcgagcttt gtagcggctt tttgccgtac    6300
ctttggattc tttccagaca atggttacca tgatggtctc ctttaagtgg ctttggcgca    6360
tgacgcgtcg aggtgcttat cttctcgatc gctgtcttgt agctgcaatt cgcgccatcc    6420
ccaaaaccac tcaagttctg gtctcaacgg ttaggttgag agtccgtcga tgttaaagag    6480
cctgccaatc tgttccgttt ggcttccagc gtcctgctga tggcttaaat ttaagacttc    6540
ttaatttatt ggtcaagtgc attttttgaag aaaacttaat tttatgggcg tgaatttagt    6600
ttgtctttga ttttttaacgg gaaataaaaa aggggcgaaa gccccttaag gaaggtttgc    6660
tagcttggca tcaacgacaa cgccaatgat tttacagttc ccattgattt caatcattgg    6720
gtattgtgga ttgagtggtt tcaggaattt tctaccggca tcaataacta acttttttgaa   6780 tgtcgcctcg ttttctcctt caagtttggc gactaccagc tttccattac gtggttcgac    6840
ttctgggtcg acgagaataa tcatcccctc aggaatactc agtcctgccg gggcagtcat    6900
tgaatcgcct ttaacgtcga gccaaaaaga gtcttcagaa caatctaccg ttgtgtcgta    6960
ccagttatct attgcacgcc tatgatatgg ctctacagct ccatccaac atcctgcgct     7020 tacccaacta attagaggat acgaacctct tggatcatgc ctgctgtgat aggcaatgtt    7080
tgaaagacta tcctctcctt tcaacaggta atcagggggag cactgcaaag ccttggctaa    7140
ggccaatagg ttttcgccat tgggctcagt ttcagatcgc tcccattggg aaatagcaac    7200
attagacacg ccaaccatct tgccaagggc agcctgccta atcttgagtt cttttctgcg    7260
```

```
agcgcgaata cgctcaccca tcagttgtgt attcatagtt aagacatctt aaataaactt      7320
gacttaagat tcctttggtg gataatttaa gtgttcttta atttcggagc gagtctatgt      7380
acaaaaaaga tgttattgac cacttcggaa cccagcgtgc tgttgctaaa gcactaggca      7440
ttagcgatgc agcagtctct cagtggaaag aagttatccc agagaaagac gcctatcgat      7500
tggaaatcgt tacagctggc gccctgaagt atcaagaaag tgcttaccgc caagcggcat      7560
aagcaaattg ctctttaaca gttctggcct ttcacctcta accgggtgag caaacatcag      7620
cggcaaatcc attgggtgtg ccgctataac tcaatatcaa tataggtaaa ttaacaaatg      7680
gcacaagcaa gctacagcaa gccaacacag cgagaaattg atcgcgctga aactgattta      7740
ctcatcaacc tgtcaacgct tacccagcgc ggtctggcaa agatgattgg ctgtcatgaa      7800
tcgaagataa gcagaacgga ctggagattt attgcttcgg tcttgtgtgc tttcggaatg      7860
gcatcagaca tcagtccgat tagcagggct tttaagtatg cgcttgatgg actcacaaag      7920
aaaaaacgcc cggtgtgcaa gaccgagcgt tctgaacaaa tccagatgga gttctgaggt      7980
cattactgga tctatcaaca ggagtcatta tgacaaatac agcaaaaata ctcaacttcg      8040
gcagaggtaa cttttgccgga caggagcgta atgtggcaga tctcgatgat ggttacgcca      8100
gactatcaaa tatgctgctt gaggcttatt cgggcgcaga tctgaccaag cgacagttta      8160
aagtgctgct tgccattctg cgtaaaacct atgggtggaa taaaccaatg gacagaatca      8220
ccgattctca acttagcgag attacaaagt tacctgtcaa acggtgcaat gaagccaagt      8280
tagaactcgt cagaatgaat attatcaagc agcaaggcgg catgtttgga ccaaataaaa      8340
acatctcaga atggtgtatc cctcaaaacg agggaaaatc ccctaaaacg agggataaaa      8400
catccctcaa attgggggat tgctatccct caaaacaggg ggacacaaaa gacactatta      8460
caaaagaaaa aagaaaagat tattcgtcag agaattctgg cgaatcctct gaccagccag      8520
aaaacgacct ttctgtggtg aaaccggatg ctgcaattca gagcggcagc aagtggggga      8580
cagcagaaga cctgaccgcc gcagagtgga tgtttgacat ggtgaagact atcgcaccat      8640
cagccagaaa accgaatttt gctgggtggg ctaacgatat ccgcctgatg cgtgaacgtg      8700
acggacgtaa ccaccgcgac atgtgtgtgc tgttccgctg gcatgccag acaacttct      8760 ggtccggtaa cgtgctgagc ccggccaaac tccgcgataa gtggacccaa ctcgaaatca      8820
accgtaacaa gcaacaggca ggcgtgacag ccagcaaacc aaaactcgac ctgacaaaca      8880
cagactggat ttacggggtg gatctatgaa aaacatcgcc gcacagatgg ttaactttga      8940
ccgtgagcag atgcgtcgga tcgccaacaa catgccggaa cagtacgacg aaaagccgca      9000
ggtacagcag gtagcgcaga tcatcaacgg tgtgttcagc cagttactgg caactttccc      9060
ggcgagcctg gctaaccgtg accagaacga agtgaacgaa atccgtcgcc agtgggttct      9120
ggcttttcgg gaaaacggga tcaccacgat ggaacaggtt aacgcaggaa tgcgcgtagc      9180
ccgtcggcag aatcgaccat ttctgccatc acccgggcag tttgttgcat ggtgccggga      9240
agaagcatcc gttaccgccg gactgccaaa cgtcagcgag ctggttgata tggtttacga      9300
gtattgccgg aagcgaggcc tgtatccgga tgcggagtct atccgtggaa atcaaacgc      9360 gcactactgg ctggttacca acctgtatca gaacatgcgg gccaatgcgc ttactgatgc      9420
ggaattacgc cgtaaggccg cagatgagct tgtccatatg actgcgagaa ttaaccgtgg      9480
tgaggcgatc cctgaaccag taaaacaact tcctgtcatg ggcggtagac ctctaaatcg      9540
tgcacaggct ctggcgaaga tcgcagaaat caaagctaag ttcggactga aaggagcaag      9600
tgtatgacgg gcaaagaggc aattattcat tacctgggga cgcataatag cttctgtgcg      9660
```

```
ccggacgttg ccgcgctaac aggcgcaaca gtaaccagca taaatcaggc cgcggctaaa   9720
atggcacggg caggtcttct ggttatcgaa ggtaaggtct ggcgaacggt gtattaccgg   9780
tttgctacca gggaagaacg ggaaggaaag atgagcacga acctgatgaa caaactggat   9840
acgattggat tcgacaacaa aaaagacctg cttatctcgg tgggcgattt ggttgatcgt   9900
ggtgcagaga acgttgaatg cctggaatta atcacattcc cctggttcag agctgtacgt   9960
ggaaaccatg agcaaatgat gattgatggc ttatcagagc gtggaaacgt taatcactgg  10020
ctgcttaatg gcggtggctg gttctttaat ctcgattacg acaaagaaat tctggctaaa  10080
gctcttgccc ataaagcaga tgaacttccg ttaatcatcg aactggtgag caaagataaa  10140
aaatatgtta tctgccacgc cgattatccc tttgacgaat acgagtttgg aaagccagtt  10200
gatcatcagc aggtaatctg gaaccgcgaa cgaatcagca actcacaaaa cgggatcgtg  10260
aaagaaatca aggcgcgga cacgttcatc tttggtcata cgccagcagt gaaaccactc  10320
aagtttgcca accaaatgta tatcgatacc ggcgcagtgt tctgcggaaa cctaacattg  10380
attcaggtac agggagaagg cgcatgagac tcgaaagcgt agctaaattt cattcgccaa  10440
aaagcccgat gatgagcgac tcaccacggg ccacggcttc tgactctctt tccggtactg  10500
atgtgatggc tgctatgggg atggcgcaat cacaagccgg attcggtatg gctgcattct  10560
gcggtaagca cgaactcagc cagaacgaca aacaaaaggc tatcaactat ctgatgcaat  10620
ttgcacacaa ggtatcgggg aaataccgtg gtgtggcata tcttgaagga aatactaagg  10680
caaaggtact gcaagtgctc gcaacattcg cttatgcgga ttattgccgt agtgccgcga  10740
cgccgggggc aagatgcaga gattgccatg gtacaggccg tgcggttgat attgccaaaa  10800
cagagctgtg ggggagagtt gtcgagaaag agtgcggaag atgcaaaggc gtcggctatt  10860
caaggatgcc agcaagcgca gcatatcgcg ctgtgacgat gctaatccca aaccttaccc  10920
aacccacctg gtcacgcact gttaagccgc tgtatgacgc tctggtggtg caatgccaca  10980
aagaagagtc aatcgcagac aacattttga atgcggtcac acgttagcag catgattgcc  11040
acggatggca acatattaac ggcatgatat tgacttattg aataaaattg ggtaaatttg  11100
actcaacgat gggttaattc gctcgttgtg gtagtgagat gaaaagaggc ggcgcttact  11160
accgattccg cctagttggt cacttcgacg tatcgtctgg aactccaacc atcgcaggca  11220
gagaggtctg caaaatgcaa tcccgaaaca gttcgcaggt aatagttaga gcctgcataa  11280
cggtttcggg attttttata tctgcacaac aggtaagagc attgagtcga taatcgtgaa  11340
gagtcggcga gcctggttag ccagtgctct ttccgttgtg ctgaattaag cgaataccgg  11400
aagcagaacc ggatcaccaa atgcgtacag gcgtcatcgc cgcccagcaa cagcacaacc  11460
caaactgagc cgtagccact gtctgtcctg aattccatgc ttgaacccgc ctatgcgcgg  11520
gttttctttt gtgcgcttgc aggccagctt gggatcagca gcctgacgga tgcggtgtcc  11580
ggcgacagcc tgactgccca ggaggcactc gcgacgctgg cattatccgg tgatgatgac  11640
ggaccacgac aggcccgcag ttatcaggtc atgaacggca tcgccgtgct gccggtgtcc  11700
ggcacgctgg tcagccggac gcgggcgctg cagccgtact cggggatgac cggttacaac  11760
ggcattatcg cccgtctgca acaggctgcc agcgatccga tggtgacgg cattctgctc  11820 gatatggaca cgcccggcgg gatggtggcg ggggcatttg actgcgctga catcatcgcc  11880
cgtgtgcgtg acataaaacc ggtatgggcg cttgccaacg acatgaactg cagtgcaggt  11940
cagttgcttg ccagtgccgc ctcccggcgt ctggtcacgc agaccgcccg gacaggctcc  12000
```

```
atcggcgtca tgatggctca cagtaattac ggtgctgcgc tggagaaaca gggtgtggaa    12060
atcacgctga tttacagcgg cagccataag gtggatggca accccctacag ccatcttccg   12120 gatgacgtcc gggagacact gcagtccggg atggacgcaa cccgccagat gtttgcgcag    12180
aaggtgtcgg catataccgg cctgtccgtg caggttgtgc tggataccga ggctgcagtg    12240
tacagcggtc aggaggccat tgatgccgga ctggctgatg aacttgttaa cagcaccgat    12300
gcgatcaccg tcatgcgtga tgcactggat gcacgtaaat cccgtctctc aggagggcga    12360
atgaccaaag agactcaatc aacaactgtt tcagccactg cttcgcaggc tgacgttact    12420
gacgtggtgc cagcgacgga gggcgagaac gccagcgcgg cgcagccgga cgtgaacgcg    12480
cagatcaccg cagcggttgc ggcagaaaac agccgcatta tggggatact caactgtgag    12540
gaggctcacg gacgcgaaga acaggcacgc gtgctggcag aaaccccggg tatgaccgtg    12600
aaaacggccc gccgcattct ggccgcagca ccacagagtg cacaggcgcg cagtgacact    12660
gcgctggatc gtctgatgca gggggcaccg gcaccgctgg ctgcaggtaa cccggcatct    12720
gatgccgtta acgatttgct gaacacacca gtgtaaggga tgtttatgac gagcaaagaa    12780
acctttaccc attaccagcc gcagggcaac agtgacccgg ctcataccgc aaccgcgccc    12840
ggcggattga gtgcgaaagc gcctgcaatg accccgctga tgctggacac ctccagccgt    12900
aagctggttg cgtgggatgg caccaccgac ggtgctgccg ttggcattct tgcggttgct    12960
gctgaccaga ccagcaccac gctgacgttc tacaagtccg gcacgttccg ttatgaggat    13020
gtgctctggc cggaggctgc cagcgacgag acgaaaaaac ggaccgcgtt tgccggaacg    13080
gcaatcagca tcgtttaact ttacccttca tcactaaagg ccgcctgtgc ggcttttttt    13140
acgggatttt tttatgtcga tgtacacaac cgcccaactg ctggcggcaa atgagcagaa    13200
atttaagttt gatccgctgt ttctgcgtct cttttttccgt gagagctatc ccttcaccac    13260
ggagaaagtc tatctctcac aaattccggg actggtaaac atggcgctgt acgtttcgcc    13320 gattgttttcc ggtgaggtta tccgttcccg tggcggctcc acctctgaat ttacgccggg   13380
atatgtcaag ccgaagcatg aagtgaatcc gcagatgacc ctgcgtcgcc tgccggatga    13440
agatccgcag aatctggcgg acccggctta ccgccgccgt cgcatcatca tgcagaacat    13500
gcgtgacgaa gagctggcca ttgctcaggt cgaagagatg caggcagttt ctgccgtgct    13560
taagggcaaa tacaccatga ccggtgaagc cttcgatccg gttgaggtgg atatgggccg    13620
cagtgaggag aataacatca cgcagtccgg cggcacggag tggagcaagc gtgacaagtc    13680
cacgtatgac ccgaccgacg atatcgaagc ctacgcgctg aacgccagcg gtgtggtgaa    13740
tatcatcgtg ttcgatccga aaggctgggc gctgttccgt tccttcaaag ccgtcaagga    13800
gaagctggat acccgtcgtg gctctaattc cgagctggag acagcggtga agacctggg    13860 caaagcggtg tcctataagg ggatgtatgg cgatgtggcc atcgtcgtgt attccggaca    13920
gtacgtggaa aacggcgtca aaagaacttt cctgccggac aacacgatgg tgctggggaa    13980
cactcaggca cgcggtctgc gcacctatgg ctgcattcag gatgcggacg cacagcgcga    14040
aggcattaac gcctctgccc gttacccgaa aaactgggtg accaccggcg atccggcgcg   14100
tgagttcacc atgattcagt cagcaccgct gatgctgctg gctgaccctg atgagttcgt    14160
gtccgtacaa ctggcgtaat catggccctt cggggccatt gtttctctgt ggaggagtcc    14220
atgacgaaag atgaactgat tgcccgtctc cgctcgctgg gtgaacaact gaaccgtgat    14280
gtcagcctga cggggacgaa agaagaactg gcgctccgtg tggcagagct gaaagaggag    14340
cttgatgaca cggatgaaac tgccggtcag gacaccccctc tcagccggga aaatgtgctg    14400
```

```
accggacatg aaaatgaggt gggatcagcg cagccggata ccgtgattct ggatacgtct   14460
gaactggtca cggtcgtggc actggtgaag ctgcatactg atgcacttca cgccacgcgg   14520
gatgaacctg tggcatttgt gctgccggga acggcgtttc gtgtctctgc cggtgtggca   14580
gccgaaatga cagagcgcgg cctggccaga atgcaataac gggaggcgct gtggctgatt   14640
tcgataacct gttcgatgct gccattgccc gcgccgatga acgatacgc gggtacatgg    14700 gaacgtcagc caccattaca tccggtgagc agtcaggtgc ggtgatacgt ggtgtttttg   14760
atgaccctga aaatatcagc tatgccggac agggcgtgcg cgttgaaggc tccagcccgt   14820
ccctgtttgt ccggactgat gaggtgcggc agctgcggcg tggagacacg ctgaccatcg   14880
gtgaggaaaa tttctgggta gatcgggttt cgccggatga tggcggaagt tgtcatctct   14940
ggcttggacg gggcgtaccg cctgccgtta accgtcgccg ctgaaagggg gatgtatggc   15000
cataaaaggt cttgagcagg ccgttgaaaa cctcagccgt atcagcaaaa cggcggtgcc   15060
tggtgccgcc gcaatggcca ttaaccgcgt tgcttcatcc gcgatatcgc agtcggcgtc   15120
acaggttgcc cgtgagacaa aggtacgccg gaaactggta aaggaaaggg ccaggctgaa   15180
aagggccacg gtcaaaaatc cgcaggccag aatcaaagtt aaccgggggg atttgcccgt   15240
aatcaagctg ggtaatgcgc gggttgtcct ttcgcgccgc aggcgtcgta aaaggggca    15300 gcgttcatcc ctgaaaggtg gcggcagcgt gcttgtggtg ggtaaccgtc gtattcccgg   15360
cgcgtttatt cagcaactga aaaatggccg gtggcatgtc atgcagcgtg tggctgggaa   15420
aaaccgttac cccattgatg tggtgaaaat cccgatggcg gtgccgctga ccacggcgtt   15480
taaacaaaat attgagcgga tacggcgtga acgtcttccg aaagagctgg gctatgcgct   15540
gcagcatcaa ctgaggatgg taataaagcg atgaaacata ctgaactccg tgcagccgta   15600
ctggatgcac tggagaagca tgacaccggg gcgacgtttt ttgatggtcg ccccgctgtt   15660
tttgatgagg cggattttcc ggcagttgcc gtttatctca ccggcgctga atacacgggc   15720
gaagagctgg acagcgatac ctggcaggcg gagctgcata tcgaagtttt cctgcctgct   15780
caggtgccgg attcagagct ggatgcgtgg atggagtccc ggatttatcc ggtgatgagc   15840
gatatcccgg cactgtcaga tttgatcacc agtatggtgg ccagcggcta tgactaccgg   15900
cgcgacgatg atgcgggctt gtggagttca gccgatctga cttatgtcat tacctatgaa   15960
atgtgaggac gctatgcctg taccaaatcc tacaatgccg gtgaaaggtg ccgggaccac   16020
cctgtgggtt tataagggga gcggtgaccc ttacgcgaat ccgctttcag acgttgactg   16080
gtcgcgtctg gcaaaagtta aagacctgac gcccggcgaa ctgaccgctg agtcctatga   16140
cgacagctat ctcgatgatg aagatgcaga ctggactgcg accgggcagg gcagaaatc    16200 tgccggagat accagcttca cgctggcgtg atgcccgga gagcagggc agcaggcgct     16260 gctggcgtgg tttaatgaag gcgataccg tgcctataaa atccgcttcc gaacggcac     16320 ggtcgatgtg ttccgtggct gggtcagcag tatcggtaag gcggtgacgg cgaaggaagt   16380
gatcacccgc acggtgaaag tcaccaatgt gggacgtccg tcgatggcag aagatcgcag   16440
cacggtaaca gcggcaaccg gcatgaccgt gacgcctgcc agcacctcgg tggtgaaagg   16500
gcagagcacc acgctgaccg tggccttcca gccgagggc gtaaccgaca agagctttcg    16560
tgcggtgtct gcggataaaa caaaagccac cgtgtcggtc agtggtatga ccatcaccgt   16620
gaacggcgtt gctgcaggca aggtcaacat tccggttgta tccggtaatg gtgagtttgc   16680
tgcggttgca gaaattaccg tcaccgccag ttaatccgga gagtcagcga tgttcctgaa   16740
```

```
aaccgaatca tttgaacata acggtgtgac cgtcacgctt tctgaactgt cagccctgca   16800
gcgcattgag catctcgccc tgatgaaacg gcaggcagaa caggcggagt cagacagcaa   16860
ccggaagttt actgtggaag acgccatcag aaccggcgcg tttctggtgg cgatgtccct   16920
gtggcataac catccgcaga agacgcagat gccgtccatg aatgaagccg ttaaacagat   16980
tgagcaggaa gtgcttacca cctggcccac ggaggcaatt tctcatgctg aaaacgtggt   17040
gtaccggctg tctggtatgt atgagtttgt ggtgaataat gccctgaac agacaggag    17100 cgccgggccc gcagagcctg tttctgcggg aaagtgttcg acggtgagct gagttttgcc   17160
ctgaaactgg cgcgtgagat ggggcgaccc gactggcgtg ccatgcttgc cgggatgtca   17220
tccacggagt atgccgactg gcaccgcttt tacagtaccc attattttca tgatgttctg   17280
ctggatatgc acttttccgg gctgacgtac accgtgctca gcctgttttt cagcgatccg   17340
gatatgcatc cgctggattt cagtctgctg aaccggcgcg aggctgacga agagcctgaa   17400
gatgatgtgc tgatgcagaa agcggcaggg cttgccggag gtgtccgctt tggcccggac   17460
gggaatgaag ttatccccgc ttccccggat gtggcggaca tgacggagga tgacgtaatg   17520
ctgatgacag tatcagaagg gatcgcagga ggagtccggt atggctgaac cggtaggcga   17580
tctggtcgtt gatttgagtc tggatgcggc cagatttgac gagcagatgg ccagagtcag   17640
gcgtcatttt tctggtacgg aaagtgatgc gaaaaaaaca gcggcagtcg ttgaacagtc   17700
gctgagccga caggcgctgg ctgcacagaa agcggggatt tccgtcgggc agtataaagc   17760
cgccatgcgt atgctgcctg cacagttcac cgacgtggcc acgcagcttg caggcgggca   17820
aagtccgtgg ctgatcctgc tgcaacaggg ggggcaggtg aaggactcct tcggcgggat   17880
gatccccatg ttcaggggc ttgccggtgc gatcaccctg ccgatggtgg ggccacctc    17940 gctggcggtg gcgaccggtg cgctggcgta tgcctggtat cagggcaact caaccctgtc   18000
cgatttcaac aaaacgctgg tccttttccgg caatcaggcg ggactgacgg cagatcgtat   18060
gctggtcctg tccagagccg ggcaggcggc agggctgacg tttaaccaga ccagcgagtc   18120
actcagcgca ctggttaagg cggggtaag cggtgaggct cagattgcgt ccatcagcca   18180
gagtgtggcc cgtttctcct ctgcatccgg cgtggaggtg gacaaggtcg ctgaagcctt   18240
cgggaagctg accacagacc cgacgtcggg gctgacggcg atggctcgcc agttccataa   18300
cgtgtcggcg gagcagattg cgtatgttgc tcagttgcag cgttccggcg atgaagccgg   18360
ggcattgcag gcggcgaacg aggccgcaac gaaagggttt gatgaccaga cccgccgcct   18420
gaaagagaac atgggcacgc tggagacctg ggcagacagg actgcgcggg cattcaaatc   18480
catgtgggat gcggtgctgg atattggtcg tcctgatacc gcgcaggaga tgctgattaa   18540
ggcagaggct gcgtataaga aagcagacga catctggaat ctgcgcaagg atgattattt   18600
tgttaacgat gaagcgcggg cgcgttactg ggatgatcgt gaaaaggccc gtcttgcgct   18660
tgaagccgcc cgaaagaagg ctgagcagca gactcaacag gacaaaaatg cgcagcagca   18720
gagcgatacc gaagcgtcac ggctgaaata taccgaagag gcgcagaagg cttacgaacg   18780
gctgcagacg ccgctggaga aatataccgc ccgtcaggaa gaactgaaca aggcactgaa   18840
agacgggaaa atcctgcagg cggattacaa cacgctgatg gcggcggcga aaaggatta   18900 tgaagcgacg ctgaaaaagc cgaaacagtc cagcgtgaag gtgtctgcgg gcgatcgtca   18960
ggaagacagt gctcatgctg ccctgctgac gcttcaggca gaactccgga cgctggagaa   19020
gcatgccgga gcaaatgaga aaatcagcca gcagcgccgg gatttgtgga aggcggagag   19080
tcagttcgcg gtactggagg aggcggcgca acgtcgccag ctgtctgcac aggagaaatc   19140
```

```
cctgctggcg cataaagatg agacgctgga gtacaaacgc cagctggctg cacttggcga    19200
caaggttacg tatcaggagc gcctgaacgc gctggcgcag caggcggata aattcgcaca    19260
gcagcaacgg gcaaaacggg ccgccattga tgcgaaaagc cggggggctga ctgaccggca    19320 ggcagaacgg gaagccacgg aacagcgcct gaaggaacga tatggcgata tccgctggc    19380 gctgaataac gtcatgtcag agcagaaaaa gacctgggcg gctgaagacc agcttcgcgg    19440
gaactggatg gcaggcctga agtccggctg gagtgagtgg gaagagagcg ccacggacag    19500
tatgtcgcag gtaaaaagtg cagccacgca gacctttgat ggtattgcac agaatatggc    19560
ggcgatgctg accggcagtg agcagaactg gcgcagcttc acccgttccg tgctgtccat    19620
gatgacagaa attctgctta agcaggcaat ggtggggatt gtcgggagta tcggcagcgc    19680
cattggcggg gctgttggtg gcggcgcatc cgcgtcaggc ggtacagcca ttcaggccgc    19740
tgcggcgaaa ttccattttg caaccggagg atttacggga accggcggca aatatgagcc    19800
agcggggatt gttcaccgtg gtgagtttgt cttcacgaag gaggcaacca gccggattgg    19860
cgtggggaat ctttaccggc tgatgcgcgg ctatgccacc ggcggttatg tcggtacacc    19920
gggcagcatg gcagacagcc ggtcgcaggc gtccgggacg tttgagcaga ataaccatgt    19980
ggtgattaac aacgacggca cgaacgggca gataggtccg gctgctctga aggcggtgta    20040
tgacatggcc cgcaagggtg cccgtgatga aattcagaca cagatgcgtg atggtggcct    20100
gttctccgga ggtggacgat gaagaccttc cgctggaaag tgaaacccgg tatggatgtg    20160
gcttcggtcc cttctgtaag aaaggtgcgc tttggtgatg gctattctca gcagcgcct    20220 gccgggctga atgccaacct gaaaacgtac agcgtgacgc tttctgtccc ccgtgaggag    20280
gccacggtac tggagtcgtt tctggaagag cacgggggct ggaaatcctt tctgtggacg    20340
ccgccttatg agtggcggca gataaaggtg acctgcgcaa aatggtcgtc gcgggtcagt    20400
atgctgcgtg ttgagttcag cgcagagttt gaacaggtgg tgaactgatg caggatatcc    20460
ggcaggaaac actgaatgaa tgcacccgtg cggagcagtc ggccagcgtg gtgctctggg    20520
aaatcgacct gacagaggtc ggtggagaac gttattttt ctgtaatgag cagaacgaaa    20580
aaggtgagcc ggtcacctgg caggggcgac agtatcagcc gtatcccatt caggggagcg    20640
gttttgaact gaatggcaaa ggcaccagta cgcgccccac gctgacggtt tctaacctgt    20700
acggtatggt caccgggatg gcggaagata tgcagagtct ggtcggcgga acggtggtcc    20760
ggcgtaaggt ttacgcccgt tttctggatg cggtgaactt cgtcaacgga aacagttacg    20820
ccgatccgga gcaggaggtg atcagccgct ggcgcattga gcagtgcagc gaactgagcg    20880
cggtgagtgc ctcctttgta ctgtccacgc cgacggaaac ggatggcgct gttttttccgg    20940 gacgtatcat gctggccaac acctgcacct ggacctatcg cggtgacgag tgcggttata    21000
gcggtccggc tgtcgcggat gaatatgacc agccaacgtc cgatatcacg aaggataaat    21060
gcagcaaatg cctgagcggt tgtaagttcc gcaataacgt cggcaacttt gcggcttcc    21120 tttccattaa caaactttcg cagtaaatcc catgacacag acagaatcag cgattctggc    21180
gcacgcccgg cgatgtgcgc cagcggagtc gtgcggcttc gtggtaagca cgccggaggg    21240
ggaaagatat ttcccctgcg tgaatatctc cggtgagccg gaggcgtatt tccgtatgtc    21300 gccgaagac tggctgcagg cagaaatgca gggtgagatt gtggcgctgg tccacagcca    21360
ccccggtggt ctgccctggc tgagtgaggc cgaccggcgg ctgcaggtgc agagtgattt    21420
gccgtggtgg ctggtctgcc gggggacgat tcataagttc cgctgtgtgc cgcatctcac    21480
```

```
cgggcggcgc tttgagcacg gtgtgacgga ctgttacaca ctgttccggg atgcttatca    21540
tctggcgggg attgagatgc cggactttca tcgtgaggat gactggtggc gtaacggcca    21600
gaatctctat ctggataatc tggaggcgac ggggctgtat caggtgccgt tgtcagcggc    21660
acagccgggc gatgtgctgc tgtgctgttt tggttcatca gtgccgaatc acgccgcaat    21720
ttactgcggc gacggcgagc tgctgcacca tattcctgaa caactgagca acgagagag    21780 gtacaccgac aaatggcagc gacgcacaca ctccctctgg cgtcaccggg catgcgcgc    21840 atctgccttt acggggattt acaacgattt ggtcgccgca tcgaccttcg tgtgaaaacg    21900
ggggctgaag ccatccgggc actgccaca cagctcccgg cgtttcgtca gaaactgagc    21960
gacggctggt atcaggtacg gattgccggg cgggacgtca gcacgtccgg gttaacggcg    22020
cagttacatg agactctgcc tgatggcgct gtaattcata ttgttcccag agtcgccggg    22080
gccaagtcag gtggcgtatt ccagattgtc ctgggggctg ccgccattgc cggatcattc    22140
tttaccgccg gagccaccct tgcagcatgg ggggcagcca ttggggccgg tggtatgacc    22200
ggcatcctgt tttctctcgg tgccagtatg gtgctcggtg gtgtgcgca gatgctggca    22260 ccgaaagcca gaactccccg tatacagaca acggataacg gtaagcagaa cacctatttc    22320
tcctcactgg ataacatggt tgcccagggc aatgttctgc ctgttctgta cggggaaatg    22380
cgcgtggggt cacgcgtggt ttctcaggag atcagcacgg cagacgaagg ggacggtggt    22440
caggttgtgg tgattggtcg ctgatgcaaa atgttttatg tgaaaccgcc tgcgggcggt    22500
tttgtcattt atggagcgtg aggaatgggt aaaggaagca gtaaggggca taccccgcgc    22560
gaagcgaagg acaacctgaa gtccacgcag ttgctgagtg tgatcgatgc catcagcgaa    22620
gggccgattg aaggtccggt ggatggctta aaaagcgtgc tgctgaacag tacgccggtg    22680
ctggacactg aggggaatac caacatatcc ggtgtcacgg tggtgttccg ggctggtgag    22740
caggagcaga ctccgccgga gggatttgaa tcctccggct ccagacggt gctgggtacg    22800 gaagtgaaat atgacacgcc gatcacccgc accattacgc tgcaaacat cgaccgtctg    22860 cgctttacct tcggtgtaca ggcactggtg gaaaccacct caaagggtga caggaatccg    22920
tcggaagtcc gcctgctggt tcagatacaa cgtaacggtg gctgggtgac ggaaaaagac    22980
atcaccatta agggcaaaac cacctcgcag tatctggcct cggtggtgat gggtaacctg    23040
ccgccgcgcc cgtttaatat ccggatgcgc aggatgacgc cggacagcac cacagaccag    23100
ctgcagaaca aaacgctctg gtcgtcatac actgaaatca tcgatgtgaa acagtgctac    23160
ccgaacacgg cactggtcgg cgtgcaggtg gactcggagc agttcggcag ccagcaggtg    23220
agccgtaatt atcatctgcg cgggcgtatt ctgcaggtgc cgtcgaacta taacccgcag    23280
acgcggcaat acagcggtat ctgggacgga acgtttaaac cggcatacag caacaacatg    23340
gcctggtgtc tgtgggatat gctgacccat ccgcgctacg gcatggggaa acgtcttggt    23400
gcggcggatg tggataaatg ggcgctgtat gtcatcggcc agtactgcga ccagtcagtg    23460
ccggacggct ttggcggcac ggagccgcgc atcacctgta atgcgtacct gaccacacag    23520
cgtaaggcgt gggatgtgct cagcgatttc tgctcggcga tgcgctgtat gccggtatgg    23580
aacgggcaga cgctgacgtt cgtgcaggac cgaccgtcgg ataagacgtg gacctataac    23640
cgcagtaatg tggtgatgcc ggatgatggc gcgccgttcc gctacagctt cagcgccctg    23700
aaggaccgcc ataatgccgt tgaggtgaac tggattgacc cgaacaacgg ctgggagacg    23760
gcgacagagc ttgttgaaga tacgcaggcc attgcccgtt acggtcgtaa tgttacgaag    23820
atggatgcct ttggctgtac cagccgggg caggcacacc gcgccgggct gtggctgatt    23880
```

```
aaaacagaac tgctggaaac gcagaccgtg gatttcagcg tcggcgcaga agggcttcgc    23940
catgtaccgg gcgatgttat tgaaatctgc gatgatgact atgccggtat cagcaccggt    24000
ggtcgtgtgc tggcggtgaa cagccagacc cggacgctga cgctcgaccg tgaaatcacg    24060
ctgccatcct ccggtaccgc gctgataagc ctggttgacg gaagtggcaa tccggtcagc    24120
gtggaggttc agtccgtcac cgacggcgtg aaggtaaaag tgagccgtgt tcctgacggt    24180
gttgctgaat acagcgtatg ggagctgaag ctgccgacgc tgcgccagcg actgttccgc    24240 tgccgtgagta tccgtgagaa cgacgacggc acgtatgcca tcaccgccgt gcagcatgtg    24300
ccggaaaaag aggccatcgt ggataacggg gcgcactttg acggcgaaca gagtggcacg    24360
gtgaatggtg tcacgccgcc agcggtgcag cacctgaccg cagaagtcac tgcagacagc    24420
ggggaatatc aggtgctggc gcgatggac acaccgaagg tggtgaaggg cgtgagtttc    24480
ctgctccgtc tgaccgtaac agcggacgac ggcagtgagc ggctggtcag cacggcccgg    24540
acgacggaaa ccacataccg cttcacgcaa ctggcgctgg ggaactacag gctgacagtc    24600
cgggcggtaa atgcgtgggg gcagcagggc gatccggcgt cggtatcgtt ccggattgcc    24660
gcaccggcag caccgtcgag gattgagctg acgcccgggct attttcagat aaccgccacg    24720
ccgcatcttg ccgtttatga cccgacggta cagtttgagt tctggttctc ggaaaagcag    24780
attgcggata tcagacaggt tgaaaccagc acgcgttatc ttggtacggc gctgtactgg    24840
atagccgcca gtatcaatat caaaccgggc catgattatt acttttatat ccgcagtgtg    24900
aacaccgttg gcaaatcggc attcgtggag gccgtcggtc gggcgagcga tgatgcggaa    24960
ggttacctgg atttttttcaa aggcaagata accgaatccc atctcggcaa ggagctgctg    25020
gaaaaagtcg agctgacgga ggataacgcc agcagactgg aggagttttc gaaagagtgg    25080
aaggatgcca gtgataagtg gaatgccatg tgggctgtca aaattgagca gaccaaagac    25140
ggcaaacatt atgtcgcggg tattggcctc agcatggagg acacggagga aggcaaactg    25200
agccagtttc tggttgccgc caatcgtatc gcatttattg acccggcaaa cgggaatgaa    25260
acgccgatgt ttgtgcgcgca gggcaaccag atattcatga cgacgtgtt cctgaagcgc    25320 ctgacggccc ccaccattac cagcggcggc aatcctccgg ccttttccct gacaccggac    25380
ggaaagctga ccgctaaaaa tgcggatatc agtggcagtg tgaatgcgaa ctccgggacg    25440
ctcagtaatg tgacgatagc tgaaaactgt acgataaacg gtacgctgag gcggaaaaa    25500 atcgtcgggg acattgtaaa ggcggcgagc gcggcttttc cgcgccagcg tgaaagcagt    25560
gtggactggc cgtcaggtac ccgtactgtc accgtgaccg atgaccatcc ttttgatcgc    25620
cagatagtgg tgcttccgct gacgtttcgc ggaagtaagc gtactgtcag cggcaggaca    25680
acgtattcga tgtgttatct gaaagtactg atgaacggtg cggtgattta tgatggcgcg    25740
gcgaacgagg cggtacaggt gttctcccgt attgttgaca tgccagcggg tcggggaaac    25800
gtgatcctga cgttcacgct tacgtccaca cggcattcgg cagatattcc gccgtatacg    25860
tttgccagcg atgtgcaggt tatggtgatt aagaaacagg cgctgggcat cagcgtggtc    25920
tgagtgtgtt acagaggttc gtccgggaac gggcgtttta ttataaaaca gtgagaggtg    25980
aacgatgcgt aatgtgtgta ttgccgttgc tgtctttgcc gcacttgcgg tgacagtcac    26040
tccggcccgt gcggaaggtg gacatggtac gtttacggtg ggctattttc aagtgaaacc    26100
gggtacattg ccgtcgttgt cgggcgggga taccggtgtg agtcatctga aagggattaa    26160
cgtgaagtac cgttatgagc tgacggacag tgtgggggtg atggcttccc tggggttcgc    26220
```

```
cgcgtcgaaa aagagcagca cagtgatgac cggggaggat acgtttcact atgagagcct    26280
gcgtggacgt tatgtgagcg tgatggccgg accggtttta caaatcagta agcaggtcag    26340
tgcgtacgcc atggccggag tggctcacag tcggtggtcc ggcagtacaa tggattaccg    26400
taagacggaa atcactcccg ggtatatgaa agagacgacc actgccaggg acgaaagtgc    26460
aatgcggcat acctcagtgg cgtggagtgc aggtatacag attaatccgg cagcgtccgt    26520
cgttgttgat attgcttatg aaggctccgg cagtggcgac tggcgtactg acggattcat    26580
cgttggggtc ggttataaat tctgattagc caggtaacac agtgttatga cagcccgccg    26640
gaaccggtgg gctttttgt ggggtgaata tggcagtaaa gatttcagga gtcctgaaag    26700
acggcacagg aaaaccggta cagaactgca ccattcagct gaaagccaga cgtaacagca    26760
ccacggtggt ggtgaacacg gtgggctcag agaatccgga tgaagccggg cgttacagca    26820
tggatgtgga gtacggtcag tacagtgtca tcctgcaggt tgacggtttt ccaccatcgc    26880
acgccgggac catcaccgtg tatgaagatt cacaaccggg gacgctgaat gattttctct    26940
gtgccatgac ggaggatgat gcccggccgg aggtgctgcg tcgtcttgaa ctgatggtgg    27000
aagaggtggc gcgtaacgcg tccgtggtgg cacagagtac ggcagacgcg aagaaatcag    27060
ccggcgatgc cagtgcatca gctgctcagg tcgcggccct tgtgactgat gcaactgact    27120
cagcacgcgc cgccagcacg tccgccggac aggctgcatc gtcagctcag gaagcgtcct    27180
ccggcgcaga agcggcatca gcaaaggcca ctgaagcgga aaaaagtgcc gcagccgcag    27240
agtcctcaaa aaacgcggcg gccaccagtg ccggtgcggc gaaaacgtca gaaacgaatg    27300
ctgcagcgtc acaacaatca gccgccacgt ctgcctccac cgcggccacg aaagcgtcag    27360
aggccgccac ttcagcacga gatgcggtgg cctcaaaaga ggcagcaaaa tcatcagaaa    27420
cgaacgcatc atcaagtgcc ggtcgtgcag cttcctcggc aacggcggca gaaaattctg    27480
ccagggcggc aaaaacgtcc gagacgaatg ccaggtcatc tgaaacagca gcggaacgga    27540
gcgcctctgc cgcggcagac gcaaaaacag cggcggcggg gagtgcgtca acggcatcca    27600
cgaaggcgac agaggctgcg ggaagtgcgg tatcagcatc gcagagcaaa agtgcggcag    27660
aagcggcgga atacgtgca gaaaattcgg caaaacgtgc agaagatata gcttcagctg    27720
tcgcgcttga ggatgcggac acaacgagaa aggggatagt gcagctcagc agtgcaacca    27780
acagcacgtc tgaaacgctt gctgcaacgc caaaggcggt taaggtggta atggatgaaa    27840
cgaacagaaa agcccactgg acagtccggc actgaccgga acgccaacag caccaaccgc    27900
gctcagggga caaacaata cccagattgc gaacaccgct tttgtactgg ccgcgattgc    27960
agatgttatc gacgcgtcac ctgacgcact gaatacgctg aatgaactgg ccgcagcgct    28020
cgggaatgat ccagattttg ctaccaccat gactaacgcg cttgcgggta acaaccgaa    28080 gaatgcgaca ctgacggcgc tggcagggct ttccacggcg aaaaataaat taccgtattt    28140
tgcggaaaat gatgccgcca gcctgactga actgactcag gttggcaggg atattctggc    28200
aaaaaattcc gttgcagatg ttcttgaata ccttggggcc ggtgagaatt ctaagcggag    28260
atcgcctagt gattttaaac tattgctggc agcattcttg agtccaatat aaaagtattg    28320 tgtaccttt gctgggtcag gttgttcttt aggaggagta aaaggatcaa atgcactaaa    28380
cgaaactgaa acaagcgatc gaaatatcc ctttgggatt cttgactcga taagtctatt    28440
attttcagag aaaaaatatt cattgttttc tgggttggtg attgcaccaa tcattccatt    28500
caaaattgtt gttttaccac acccattccg cccgataaaa gcatgaatgt tcgtgctggg    28560
catagaatta accgtcacct caaaaggtat agttaaatca ctgaatccgg gagcactttt    28620
```

| | | | | |
|---|---|---|---|---|
| tctattaaat | gaaaagtgga | aatctgacaa | ttctggcaaa | ccatttaaca cacgtgcgaa | 28680 |
| ctgtccatga | atttctgaaa | gagttacccc | tctaagtaat | gaggtgttaa ggacgctttc | 28740 |
| attttcaatg | tcggctaatc | gatttggcca | tactactaaa | tcctgaatag ctttaagaag | 28800 |
| gttatgttta | aaaccatcgc | ttaatttgct | gagattaaca | tagtagtcaa tgctttcacc | 28860 |
| taaggaaaaa | aacatttcag | ggagttgact | gaattttta | tctattaatg aataagtgct | 28920 |
| tacttcttct | ttttgaccta | caaaaccaat | tttaacattt | ccgatatcgc atttttcacc | 28980 |
| atgctcatca | aagacagtaa | gataaaacat | tgtaacaaag | gaatagtcat tccaaccatc | 29040 |
| tgctcgtagg | aatgccttat | ttttttctac | tgcaggaata | tacccgcctc tttcaataac | 29100 |
| actaaactcc | aacatatagt | aacccttaat | tttattaaaa | taaccgcaat ttatttggcg | 29160 |
| gcaacacagg | atctctcttt | taagttactc | tctattacat | acgttttcca tctaaaaatt | 29220 |
| agtagtattg | aacttaacgg | ggcatcgtat | tgtagttttc | catatttagc tttctgcttc | 29280 |
| cttttggata | acccactgtt | attcatgttg | catggtgcac | tgtttatacc aacgatatag | 29340 |
| tctattaatg | catatatagt | atcgccgaac | gattagctct | tcaggcttct gaagaagcgt | 29400 |
| ttcaagtact | aataagccga | tagatagcca | cggacttcgt | agccattttt cataagtgtt | 29460 |
| aacttccgct | cctcgctcat | aacagacatt | cactacagtt | atggcggaaa ggtatgcatg | 29520 |
| ctgggtgtgg | ggaagtcgtg | aaagaaaaga | agtcagctgc | gtcgtttgac atcactgcta | 29580 |
| tcttcttact | ggttatgcag | gtcgtagtgg | gtggcacaca | aagctttgca ctggattgcg | 29640 |
| aggctttgtg | cttctctgga | gtgcgacagg | tttgatgaca | aaaattagc gcaagaagac | 29700 |
| aaaaatcacc | ttgcgctaat | gctctgttac | aggtcactaa | taccatctaa gtagttgatt | 29760 |
| catagtgact | gcatatgttg | tgttttacag | tattatgtag | tctgtttttt atgcaaaatc | 29820 |
| taatttaata | tattgatatt | tatatcattt | tacgtttctc | gttca | 29865 |

<210> SEQ ID NO 11
<211> LENGTH: 2244
<212> TYPE: DNA
<213> ORGANISM: Escherichia coli

<400> SEQUENCE: 11

| | | | | |
|---|---|---|---|---|
| atggcgcgtt | ccaaaactgc | tcagccaaaa | cactcactgc | gtaaaatcgc agttgtagta | 60 |
| gccacagcgg | ttagcggcat | gtctgtttat | gcacaggcag | cggttgaacc gaaagaagac | 120 |
| actatcaccg | ttaccgctgc | acctgcgccg | caagaaagcg | catgggggcc tgctgcaact | 180 |
| attgcggcgc | gacagtctgc | taccggcact | aaaaccgata | cgccgattca aaaagtgcca | 240 |
| cagtctattt | ctgttgtgac | cgccgaagag | atggcgctgc | atcagccgaa gtcggtaaaa | 300 |
| gaagcgctta | gctacacgcc | gggtgtctct | gttggtacgc | gtggcgcatc caacacctat | 360 |
| gaccacctga | tcattcgcgg | ctttgcggca | gaaggccaaa | gccagaataa ctatctgaat | 420 |
| ggcctgaagt | tgcagggcaa | cttctataac | gatgcggtca | ttgacccgta tatgctggaa | 480 |
| cgcgctgaaa | ttatgcgtgg | cccggtttcc | gtgctttacg | gtaaaagcag tcctggcggc | 540 |
| ctgttgaata | tggtcagcaa | gcgtccgacc | accgaaccgc | tgaaagaagt tcagtttaaa | 600 |
| gccggtactg | acagcctgtt | ccagactggt | tttgacttta | gcgattcgtt ggatgatgac | 660 |
| ggtgtttact | cttatcgcct | gaccggtctt | gcgcgttctg | ccaatgccca gcagaaaggg | 720 |
| tcagaagagc | agcgttatgc | tattgcaccg | gcgttcacct | ggcgtccgga tgataaaacc | 780 |
| aattttacct | tcctttctta | cttccagaac | gagccggaaa | ccggttatta cggctggttg | 840 |

```
ccgaaagagg gaaccgttga gccgctgccg aacggtaagc gtctgccgac agactttaat    900
gaagggcga agaacaacac ctattctcgt aatgagaaga tggtcggcta cagcttcgat    960
cacgaattta acgacaccct tactgtgcgt cagaacctgc gctttgctga aacaaaacc   1020
tcgcaaaaca gcgtttatgg ttacggcgtc tgctccgatc cggcgaatgc ttacagcaaa   1080
cagtgtgcgg cattagcgcc agcggataaa ggccattatc tggcacgtaa atacgtcgtt   1140
gatgatgaga agctgcaaaa cttctccgtt gatacccagt tgcagagcaa gtttgccact   1200
ggcgatatcg accacaccct gctgaccggt gtcgacttta tgcgtatgcg taatgacatc   1260
aacgcctggt ttggttacga cgactctgtg ccactgctca atctgtacaa tccggtgaat   1320
accgatttcg acttcaatgc caaagatccg gcaaactccg gcccttaccg cattctgaat   1380
aaacagaaac aaacgggcgt ttatgttcag gatcaggcgc agtgggataa agtgctggtc   1440
accctaggcg gtcgttatga ctgggcagat caagaatctc ttaaccgcgt tgccgggacg   1500
accgataaac gtgatgacaa acagtttacc tggcgtggtg gtgttaacta cctgtttgat   1560
aatggtgtaa caccttactt cagctatagc gaatcgtttg aaccttcttc gcaagttggg   1620
aaggatggta atattttcgc accgtctaaa ggtaagcagt atgaagtcgg cgtgaaatat   1680
gtaccggaag atcgtccgat tgtagttact ggtgccgtgt ataatctcac taaaaccaac   1740
aacctgatgg cggaccctga gggttccttc ttctcggttg aaggtggcga gatccgcgca   1800
cgtggcgtag aaatcgaagc gaaagcggcg ctgtcggcga gtgttaacgt agtcggttct   1860
tatacttaca ccgatgcgga ataccaccac gatactacct ataaaggcaa tacgcctgca   1920
caggtgccaa aacacatggc ttcgttgtgg gctgactaca ccttctttga cggtccgctt   1980
tcaggtctga cgctgggcac cggtggtcgt tatactggct ccagttatgg tgatccggct   2040
aactcctttta aagtgggaag ttatacggtc gtggatgcgt tagtacgtta tgatctggcg   2100
cgagtcggca tggctggctc caacgtggcg ctgcatgtta acaacctgtt cgatcgtgaa   2160
tacgtcgcca gctgctttaa cacttatggc tgcttctggg gcgcagaacg tcaggtcgtt   2220
gcaaccgcaa ccttccgttt ctaa                                          2244

<210> SEQ ID NO 12
<211> LENGTH: 1149
<212> TYPE: DNA
<213> ORGANISM: Escherichia coli

<400> SEQUENCE: 12
atgagtctga agaaaaaaac acaatctctg tttgccaacg catttggcta ccctgccact    60
cacaccattc aggcgcctgg ccgcgtgaat ttgattggtg aacacaccga ctacaacgac   120
ggtttcgttc tgccctgcgc gattgattat caaaccgtga tcagttgtgc accacgcgat   180
gaccgtaaag ttcgcgtgat ggcagccgat tatgaaaatc agctcgacga gttttccctc   240
gatgcgccca ttgtcgcaca tgaaaaactat caatgggcta actacgttcg tggcgtggtg   300
aaacatctgc aactgcgtaa caacagcttc ggcggcgtgg acatggtgat cagcggcaat   360
gtgccgcagg gtgccgggtt aagttcttcc gcttcactgg aagtcgcggt cggaaccgta   420
ttgcagcagc tttatcatct gccgctggac ggcgcacaaa tcgcgcttaa cggtcaggaa   480
gcagaaaaac cagtttgtagg ctgtaactgc gggatcatgg atcagctaat tccgcgctc   540
ggcaagaaag atcatgcctt gctgatcgat tgccgctcac tggggaccaa agcagtttcc   600
atgcccaaag tgtggctgt cgtcatcatc aacagtaact tcaaacgtac cctggttggc   660
agcgaataca cacccgtcg tgaacagtgc gaaaccggtg cgcgtttctt ccagcagcca   720
```

```
gccctgcgtg atgtcaccat tgaagagttc aacgctgttg cgcatgaact ggacccgatc    780
gtggcaaaac gcgtgcgtca tatactgact gaaaacgccc gcaccgttga agctgccagc    840
gcgctggagc aaggcgacct gaaacgtatg ggcgagttga tggcggagtc tcatgcctct    900
atgcgcgatg atttcgaaat caccgtgccg caaattgaca ctctggtaga aatcgtcaaa    960
gctgtgattg cgacaaagg tggcgtacgc atgaccggcg cggatttgg cggctgtatc     1020 gtcgcgctga tcccggaaga gctggtgcct gccgtacagc aagctgtcgc tgaacaatat    1080
gaagcaaaaa caggtattaa agagacttt tacgtttgta aaccatcaca aggagcagga     1140
cagtgctga                                                           1149
```

<210> SEQ ID NO 13
<211> LENGTH: 1701
<212> TYPE: DNA
<213> ORGANISM: Escherichia coli

<400> SEQUENCE: 13

```
atggcgattg caattggcct cgattttggc agtgattctg tgcgagcttt ggcggtggac     60
tgcgctaccg gtgaagagat cgccaccagc gtagagtggt atccccgttg gcagaaaggg    120
caattttgtg atgccccgaa taaccagttc cgtcatcatc cgcgtgacta cattgagtca    180
atggaagcgg cactgaaaac cgtgcttgca gagcttagcg tcgaacagcg cgcagctgtg    240
gtcgggattg gcgttgacag taccggctcg acgcccgcac cgattgatgc cgacggaaac    300
gtgctggcgc tgcgcccgga gtttgccgaa aacccgaacg cgatgttcgt attgtggaaa    360
gaccacactg cggttgaaga agcggaagag attacccgtt tgtgccacgc gccgggcaac    420
gttgactact cccgctacat tggtggtatt tattccagcg aatggttctg ggcaaaaatc    480
ctgcatgtga ctcgccagga cagcgccgtg gcgcaatctg ccgcatcgtg gattgagctg    540
tgcgactggg tgccagctct gctttccggt accacccgcc cgcaggatat tcgtcgcgga    600
cgttgcagcg ccgggcataa atctctgtgg cacgaaagct ggggcggcct gccgccagcc    660
agtttctttg atgagctgga cccgatcctc aatcgccatt tgccttcccc gctgttcact    720
gacacttgga ctgccgatat tccggtgggc accttatgcc cggaatgggc gcagcgtctc    780
ggcctgcctg aaagcgtggt gatttccggc ggcgcgtttg actgccatat gggcgcagtt    840
ggcgcaggcg cacagcctaa cgcactggta aaagttatcg gtacttccac ctgcgacatt    900
ctgattgccg acaaacagag cgttggcgag cgggcagtta aggtatttg cggtcaggtt    960 gatggcagcg tggtgcctgg atttatcggt ctggaagcag ccaatcggc gtttggtgat     1020 atctacgcct ggtttggtcg cgtactcggc tggccgctgg aacagcttgc cgcccagcat     1080
ccggaactga aaacgcaaat caacgccagc cagaaacaac tgcttccggc gctgaccgaa     1140
gcatgggcca aaatccgtc tctggatcac ctgccggtgg tgctcgactg gtttaacggc     1200
cgccgcacac cgaacgctaa ccaacgcctg aaaggggtga ttaccgatct taacctcgct     1260
accgacgctc cgctgctgtt cggcggtttg attgctgcca ccgcctttgg cgcacgcgca     1320
atcatggagt gctttaccga tcaggggatc gccgttaata cgtgatggc actgggcggc     1380 atcgcgcgga aaaccaggt cattatgcag gcctgctgcg acgtgctgaa tcgcccgctg     1440
caaattgttg cctctgacca gtgctgtgcg ctcggtgcgg cgattttgc tgccgtcgcc     1500 gcgaaagtgc acgcagacat cccatcagct cagcaaaaaa tggccagtgc ggtagagaaa     1560
accctgcaac cgtgcagcga gcaggcacaa cgctttgaac agctttatcg ccgctatcag     1620
```

```
caatgggcga tgagcgccga acaacactat cttccaactt ccgccccggc acaggctgcc   1680
caggccgttg cgactctata a                                             1701
```

<210> SEQ ID NO 14
<211> LENGTH: 1503
<212> TYPE: DNA
<213> ORGANISM: Escherichia coli

<400> SEQUENCE: 14

```
atgacgattt ttgataatta tgaagtgtgg tttgtcattg gcagccagca tctgtatggc     60
ccggaaaccc tgcgtcaggt cacccaacat gccgagcacg tcgttaatgc gctgaatacg    120
gaagcgaaac tgccctgcaa actggtgttg aaaccgctgg caccacgcc ggatgaaatc     180
accgctattt gccgcgacgc gaattacgac gatcgttgcg ctggtctggt ggtgtggctg    240
cacaccttct ccccggccaa aatgtggatc aacggcctga ccatgctcaa caaaccgttg    300
ctgcaattcc acaccagtt caacgcggcg ctgccgtggg acagtatcga tatggacttt    360
atgaacctga ccagactgc acatggcggt cgcgagttcg gcttcattgg cgcgcgtatg    420
cgtcagcaac atgccgtggt taccggtcac tggcaggata acaagccca tgagcgtatc    480
ggctcctgga tgcgtcaggc ggtctctaaa caggatccc gtcatctgaa agtctgccga    540
tttggcgata acatgcgtga agtggcggtc accgatggcg ataaagttgc cgcacagatc    600
aagttcggtt tctccgtcaa tacctgggcg gttggcgatc tggtgcaggt ggtgaactcc    660
atcagcgacg gcgatgttaa cgcgctggtc gatgagtacg aaagctgcta caccatgacg    720
cctgccacac aaatccacgg caaaaaacga cagaacgtgc tggaagcggc gcgtattgag    780
ctggggatga agcgtttcct ggaacaaggt ggcttccacg cgttcaccac cacctttgaa    840
gatttgcacg gtctgaaaca gcttcctggt ctggccgtac agcgtctgat gcagcagggt    900
tacggctttg cgggcgaagg cgactggaaa actgccgccc tgcttcgcat catgaaggtg    960
atgtcaaccg gtctgcaggg cggcacctcc tttatggagg actacaccta tcacttcgag   1020
aaaggtaatg aacctggtgct cggctcccat atgctggaag tctgcccgtc gatcgccgca   1080
gaagagaaac cgatcctcga cgttcagcat ctccggtattg gtggtaagga cgatcctgcc   1140
cgcctgatct tcaataccca aaccggccca gcgattgtcg ccagcttgat tgatctcggc   1200
gatcgttacc gtctactggt taactgcatc gacacggtga aaacaccgca ctccctgccg   1260
aaactgccgg tggcgaatgc gctgtggaaa gcgcaaccgg atctgccaac tgcttccgaa   1320
gcgtggatcc tcgctggtgg cgcgcaccat accgtcttca gccatgcact gaacctcaac   1380
gatatgcgcc aattcgccga tgcacgac attgaaatca cggtgattga taacgacaca   1440
cgcctgccag cgtttaaaga cgcgctgcgc tggaacgaag tgtattacgg gtttcgtcgc   1500
taa                                                                 1503
```

<210> SEQ ID NO 15
<211> LENGTH: 2355
<212> TYPE: DNA
<213> ORGANISM: Escherichia coli

<400> SEQUENCE: 15

```
atgaatcctg agcgttctga acgcattgaa atccccgtat tgccgctgcg cgatgtggtg     60
gtttatccgc acatggtcat ccccttattt gtcggcgggg aaaaatctat ccgttgtctg    120
gaagcggcga tggaccatga taaaaaaatt atgctggtcg cgcagaaaga agcttcaacg    180
gatgagccgg gtgtaaacga tcttttcacc gtcgggaccg tggcctctat attgcagatg    240
```

```
ctgaaactgc ctgacggcac cgtcaaagtg ctggtcgagg ggttacagcg cgcgcgtatt      300
tctgcgctct ctgacaatgg cgaacacttt tctgcgaagg cggagtatct ggagtcgccg      360
accattgatg agcgggaaca ggaagtgctg gtgcgtactg caatcagcca gttcgaaggc      420
tacatcaagc tgaacaaaaa aatcccacca gaagtgctga cgtcgctgaa tagcatcgac      480
gatccggcgc gtctggcgga taccattgct gcacatatgc cgctgaaact ggctgacaaa      540
cagtctgttc tggagatgtc cgacgttaac gaacgtctgg aatatctgat ggcaatgatg      600
gaatcggaaa tcgatctgct gcaggttgag aaacgcattc gcaaccgcgt taaaaagcag      660
atggagaaat cccagcgtga gtactatctg aacgagcaaa tgaaagctat tcagaaagaa      720
ctcggtgaaa tggacgacgc gccggacgaa aacgaagccc tgaagcgcaa aatcgacgcg      780
gcgaagatgc cgaaagaggc aaaagagaaa cggaagcag agttgcagaa gctgaaaatg       840
atgtctccga tgtcggcaga agcgaccgta gtgcgtggtt atatcgactg gatggtacag      900
gtgccgtgga atgcgcgtag caaggtcaaa aaagacctgc gtcaggcgca ggaaatcctt      960
gataccgacc attatggtct ggagcgcgtg aaagatcgaa tccttgagta tcttgcggtt     1020
caaagccgtg tcaacaaaat caagggaccg atcctctgcc tggtagggcc gccggggta     1080 ggtaaaacct ctcttggtca gtccattgcc aaagccaccg ggcgtaaata tgtccgtatg     1140
gcgctgggcg gcgtgcgtga tgaagcggaa atccgtggtc accgccgtac ttacatcggt     1200
tctatgccgg gtaaactgat ccagaaaatg gcgaaagtgg gcgtgaaaaa cccgctgttc     1260
ctgctcgatg agatcgacaa aatgtcttct gacatgcgtg gcgatccggc ctctgcactg     1320
cttgaagtgc tggatccaga gcagaacgta gcgttcagcg accactacct ggaagtggat     1380
tacgatctca gcgacgtgat gtttgtcgcg acgtcgaact ccatgaacat tccggcaccg     1440
ctgctggatc gtatggaagt gattcgcctc tccggttata ccgaagatga aaaactgaac     1500
atcgccaaac gtcacctgct gccgaagcag attgaacgta atgcactgaa aaaaggtgag     1560
ctgaccgtcg acgatagcgc cattatcggc attattcgtt actacacccg tgaggcgggc     1620
gtgcgtggtc tggagcgtga aatctccaaa ctgtgtcgca aagcggttaa gcagttactg     1680
ctcgataagt cattaaaaca tatcgaaatt aacggcgata acctgcatga ctatctcggt     1740
gttcagcgtt tcgactatgg tcgcgcggat aacgaaaacc gtgtcggtca ggtaaccggt     1800
ctggcgtgga cggaagtggg cggtgacttg ctgaccattg aaaccgcatg tgttccgggt     1860
aaaggcaaac tgacctatac cggttcgctc ggcgaagtga tgcaggagtc cattcaggcg     1920
gcgttaacga tggttcgtgc gcgtgcgaa aaactgggga tcaaccctga tttttacgaa     1980
aaacgtgaca tccacgtcca cgtaccggaa ggtgcgacgc cgaaagatgg tccgagtgcc     2040
ggtattgcta tgtgcaccgc gctggtttct tgcctgaccg gtaacccggt tcgtgccgat     2100
gtggcaatga ccggtgagat cactctgcgt ggtcaggtac tgccgatcgg tggtttgaaa     2160
gaaaaactcc tggcagcgca tcgcggcggg attaaaacag tgctaattcc gttcgaaaat     2220
aaacgcgatc tggaagagat tcctgacaac gtaattgccg atctggacat tcatcctgtg     2280
aagcgcattg aggaagttct gactctggcg ctgcaaaatg aaccgtctgg tatgcaggtt     2340
gtgactgcaa aatag                                                     2355
```

<210> SEQ ID NO 16
<211> LENGTH: 954
<212> TYPE: DNA
<213> ORGANISM: Escherichia coli

<400> SEQUENCE: 16

```
atgcgggcga aacttctggg aatagtcctg acaacccta ttgcgatcag ctcttttgct      60
tctaccgaga ctttatcgtt tactcctgac aacataaatg cggacattag tcttggaact    120
ctgagcggaa aaacaaaaga gcgtgtttat ctagccgaag aaggaggccg aaaagtcagt    180
caactcgact ggaaattcaa taacgctgca attattaaag gtgcaattaa ttgggatttg    240
atgccccaga tatctatcgg ggctgctggc tggacaactc tcggcagccg aggtggcaat    300
atggtcgatc aggactggat ggattccagt aaccccggaa cctggacgga tgaaagtaga    360
caccctgata cacaactcaa ttatgccaac gaatttgatc tgaatatcaa aggctggctc    420
ctcaacgaac ccaattaccg cctgggactc atggccggat atcaggaaag ccgttatagc    480
tttacagcca gaggtggttc ctatatctac agttctgagg agggattcag agatgatatc    540
ggctccttcc gaatggagaa aagagcaatc ggctacaaac aacgttttaa aatgccctac    600
attggcttga ctggaagtta tcgttatgaa gattttgaac tcggtggcac atttaaatac    660
agcggctggg tggaatcatc tgataacgat gaacactatg cccgggaaaa agaatcact    720
tatcgcagta aggtcaaaga ccaaaattac tattctgttg cagtcaatgc aggttattac    780
gtcacaccta acgcaaaagt ttatgttgaa ggcgcatgga atcgggttac gaataaaaaa    840
ggtaatactt cactttatga tcacaataat aacacttcag actacagcaa aatggagca     900
ggtatagaaa actataactt catcactact gctggtctta agtacacatt ttaa           954
```

<210> SEQ ID NO 17
<211> LENGTH: 624
<212> TYPE: DNA
<213> ORGANISM: Escherichia coli

<400> SEQUENCE: 17

```
atgtcaacga ttattatgga tttatgtagt tacacccgac taggtttaac cgggtatctg     60
ttgagtagag gggttaaaaa aagagaaatc aacgacattg aaaccgttga tgacctttgcc   120
atagcttgtg attcacagcg cccttcagtg gtgtttatta atgaggactg tttcatccac    180
gatgcttcta cagtcagcg tatcaagctc atcattaatc aacatcccaa tacgttattt    240
atcgtttta tggcaattgc caatgttcat tttgatgaat atctattggt cagaaaaaat    300
ttattgatca gttctaaatc gattaaaccg aatctctcg acgatatcct tggcgatatt    360
ctgaaaaaag agacaacgat aacctcgttt ttaaatatgc cgacgttatc attgagccga    420
accgaatcga gtatgttgcg aatgtggatg gcaggtcagg gaaccattca atctctgac    480
caaatgaata tcaaagccaa gaccgtttca tcgcataaag gtaatattaa acgtaagatc    540
aaaacgcata taaacaggt tatctaccat gtcgtccgac tgacggataa tgtgactaat    600
ggtatttttg tcaacatgcg ctaa                                            624
```

<210> SEQ ID NO 18
<211> LENGTH: 3567
<212> TYPE: DNA
<213> ORGANISM: Escherichia coli

<400> SEQUENCE: 18

```
atgttatggg ccttaaatat tggacaggc ccgcacagca atggattaat aacaatgatg      60
aataaatcca ttttgaatt cctgaagggc gtcaacgact tcacttatgc catcgcctgt    120
gcggcgaaa ataactaccc ggatgatccc aacacgacgc tgattaaaat gcgtatgttt    180
ggcgaagcca cagcgaaaca tcttggtctg ttactcaaca tcccccttg tgagaatcaa    240
```

-continued

```
cacgatctcc tgcgtgaact cggcaaaatc gcctttgttg atgacaacat cctctctgta    300
tttcacaaat tacgccgcat tggtaaccag gcggtgcacg aatatcataa cgatctcaac    360
gatgcccaga tgtgcctgcg actcgggttc cgcctggctg tctggtacta ccgtctggtc    420
actaaagatt atgacttccc ggtgccggtg tttgtgttgc cggaacgtgg tgaaaacctc    480
tatcaccagg aagtgctgac gctaaaacaa cagcttgaac agcaggtgcg agaaaaagcg    540
cagactcagg cagaagtcga agcgcaacag cagaagctgg ttgccctgaa cggctatatc    600
gccattctgg aaggcaaaca gcaggaaacc gaagcgcaaa cccaggctcg ccttgcggca    660
ctggaagcac agctcgccga agaacgcg gaactggcaa acagaccga acaggaacgt    720 aaggcttacc acaaagaaat taccgatcag gccatcaagc gcacactcaa ccttagcgaa    780
gaagagagtc gcttcctgat tgatgcgcaa ctgcgtaaag caggctggca ggccgacagc    840
aaaaccctgc gcttctccaa aggcgcacgt ccggaacccg gcgtcaataa agccattgcc    900
gaatggccga ccggaaaaga tgaaacgggt aatcagggct ttgcggatta tgtgctgttt    960
gtcggcctca acccatcgc ggtggtagag gcgaaacgta acaatatcga cgttcccgcc   1020
aggctcaatg agtcgtatcg ctacagtaaa tgtttcgata atggcttcct gcgggaaacc   1080
ttgcttgagc actactcacc ggatgaagtg catgaagcag tgccagagta tgaaaccagc   1140
tggcaggaca ccagcggcaa caacggtttt aaaatcccct tctgctactc gaccaacggg   1200
cgcgaatacc gcgcaacaat gaagaccaaa agcggcatct ggtatcgcga cgtgcgtgat   1260
acccgcaata tgtcgaaagc cttacccgag tggcaccgcc cggaagagct gctggaaatg   1320
ctcggcagcg aaccgcaaaa acagaatcag tggtttgccg ataaccctgg catgagcgag   1380
ctgggcctgc gttattatca ggaagatgcc gtccgcgcgg ttgaaaaggc aatcgtcaag   1440
gggcaacaag agatcctgct ggcgatggcg accggtaccg gtaaaacccg tacggcaatc   1500
gccatgatgt tccgcctgat ccagtcccag cgttttaaac gcattctctt ccttgtcgac   1560
cgccgttctc ttggcgaaca ggcgctgggc gcgtttgaag atacgcgtat taacggcgac   1620
accttcaaca gcattttcga cattaaaggg ctgacggata aattcccgga agacagcacc   1680
aaaattcacg ttgccaccgt acagtcgctg gtgaaacgca ccctgcaatc agatgaaccg   1740
atgccggtgg cccgttacga ctgtatcgtc gttgacgaag cgcatcgcgg ctatattctc   1800
gataaagagc agaccgaagg cgaactgcag ttccgcagcc agctggatta cgtctctgcc   1860
taccgtcgca ttctcgatca cttcgatgcg gtaaaaatcg ctctcaccgc caccccggcg   1920
ctacatactg tgcagatttt cggcgagccg gtttaccgtt atacctaccg taccgcggtt   1980
atcgacggtt ttctgatcga ccaggatccg cctattcaga tcatcaccccg caacgcgcag   2040 gaggggtttt atctctccaa aggcgagcag gtagagcgca tcagcccgca gggagaagtg   2100
atcaatgaca ccctggaaga cgatcaggat tttgaagtcg ccgactttaa ccgtggcctg   2160
gtgatcccgg cgtttaaccg cgccgtctgt aacgaactca ccaattatct tgacccgacc   2220
ggatcgcaaa aaacgctggt cttctgcgtc accaatgccc atgccgatat ggtggtggaa   2280
gagctgcgtg ccgcgttcaa gaaaaagtat ccgcaactgg agcacgacgc gatcatcaag   2340
atcaccggtg atgccgataa agacgcgcgc aaagtgcaga ccatgatcac ccgcttcaat   2400
aaagagcggc tgcccaatat cgtggtaacc gtcgacctgc tgacgaccgg cgtcgatatt   2460
ccgtcgatct gtaatatcgt gttcctgcgt aaagtacgca gccgcattct gtacgaacag   2520
atgaaaggcc gcgccacgcg cttatgcccg gaggtgaata aaaccagctt taagattttt   2580
```

-continued

```
gactgtgtcg atatctacag cacgctggag agcgtcgaca ccatgcgtcc ggtggtggtg    2640
cgcccgaagg tggaactgca aacgctggtc aatgaaatta ccgattcaga aacctataaa    2700
atcaccgaag cggatggccg cagttttgcc gagcacagcc atgaacaact ggtggcgaag    2760
ctccagcgta tcatcggtct ggccacgttt aaccgtgacc gcagcgaaac gatagataaa    2820
caggtgcgtc gtctggatga gctatgccag gacgcggcgg gcgtgaactt taacggcttc    2880
gcctcgcgcc tgcgggaaaa agggccgcac tggagcgccg aagtctttaa caaactgcct    2940
ggctttatcg cccgtctgga aaagctgaaa acggacatca acaacctgaa tgatgcgccg    3000
atcttcctcg atatcgacga tgaagtggtg agtgtaaaat cgctgtacgg tgattacgac    3060
acgccgcagg atttcctcga agcctttgac tcgctggtgc aacgttcccc gaacgcgcaa    3120
ccggcattgc aggcagttat taatcgcccg cgcgatctca cccgtaaagg ctggtcgag     3180 ctacaggagt ggtttgaccg ccagcacttt gaggaatctt ccctgcgcaa agcatggaaa    3240
gagacgcgca atgaagatat cgccgcccgg ctgattggtc atattcgccg cgctgcggtg    3300
ggcgatgcgc tgaaaccgtt tgaggaacgt gtcgatcacg cgctgacgcg cattaagggc    3360
gaaaacgact ggagcagcga gcaattaagc tggctcgatc gtttagcgca ggcgctgaaa    3420
gagaaagtgg tgctcgacga cgatgtcttc aaaaccggca acttccaccg tcgcggcggg    3480
aaggcgatgc tgcaaagaac ctttgacgat aatctcgata ccctgctggg caaattcagc    3540
gattatatct gggacgagct ggcctga                                        3567
```

<210> SEQ ID NO 19
<211> LENGTH: 915
<212> TYPE: DNA
<213> ORGANISM: Escherichia coli

<400> SEQUENCE: 19

```
atgacggttc ctacctatga caaatttatt gaacctgttc tgcgttatct ggcaacaaaa     60
ccggaaggtg cagccgcgcg tgatgttcat gaggctgccg cggatgcatt aggactggat    120
gacagccagc gagcgaaagt cattaccagc ggacaacttg tttataaaaa tcgtgcaggc    180
tgggcgcatg accgtttaaa acgtgccggg ttgtcgcaaa gtttgtcgcg tggcaaatgg    240
tgcctgactc ctgcgggttt tgactgggtt gcgtctcatc cccagccaat gacggagcag    300
gagacgaacc atctggcctt cgcttttgtg aatgtcaaac ttaagtcacg gccgatgcc    360 gtcgatttag atccgaaagc cgactctccc gatcatgaag aacttgcaaa gagcagcccg    420
gacgatcggt tagatcaggc gctaaaagag cttcgtgatg cggtggctga tgaggttctg    480
gaaaacttat tgcaggtttc tccttcgcgc tttgaagtca ttgttctgga tgttttgcat    540
cgcctggggt atggcggcca ccgtgatgat ttgcagcgtg ttggcggtac tggagatggt    600
ggcatcgatg gtgtgatatc gcttgataaa cttggcctgg agaaagttta tgttcaggca    660
aaacgttggc agaatactgt aggcaggcca gaattacagg cattttacgg cgcactggct    720
gggcaaaaag cgaaacgtgg ggtgtttatt accacttctg gatttacttc tcaggcgcgt    780
gactttgccc aatccgtcga gggtatggtg ttggttgatg gggaacgcct ggtgcactta    840
atgatcgaaa acgaagtagg ggtttcttca cgtttgttga aggtgccgaa actggatatg    900
gactattttg agtga                                                    915
```

<210> SEQ ID NO 20
<211> LENGTH: 708
<212> TYPE: DNA
<213> ORGANISM: Escherichia coli

<400> SEQUENCE: 20

```
atgtaccgtt atttgtctat tgctgcggtg gtactgagcg cagcattttc cggcccggcg      60
ttggccgaag gtatcaatag ttttttctcag gcgaaagccg cggcggtaaa agtccacgct     120
gacgcgcccg gtacgtttta ttgcggatgt aaaattaact ggcagggcaa aaaaggcgtt     180
gttgatctgc aatcgtgcgg ctatcaggtg cgcaaaaatg aaaaccgcgc cagccgcgta     240
gagtgggaac atgtcgttcc cgcctggcag ttcggtcacc agcgccagtg ctggcaggac     300
ggtggacgta aaaactgcgc taaagatccg gtctatcgca agatggaaag cgatatgcat     360
aacctgcagc cgtcagtcgg tgaggtgaat ggcgatcgcg gcaactttat gtacagccag     420
tggaatggcg gtgaaggcca gtacggtcaa tgcgccatga aggtcgattt caaagaaaaa     480
gctgccgaac caccagcgcg tgcacgcggt gccattgcgc gcacctactt ctatatgcgc     540
gaccaataca acctgacact ctctcgccag caaacgcagc tgttcaacgc atggaacaag     600
atgtatccgg ttaccgactg ggagtgcgag cgcgatgaac gcatcgcgaa ggtgcagggc     660
aatcataacc cgtatgtgca acgcgcttgc caggcgcgaa agagctaa                  708
```

<210> SEQ ID NO 21
<211> LENGTH: 1062
<212> TYPE: DNA
<213> ORGANISM: Escherichia coli

<400> SEQUENCE: 21

```
atggctatcg acgaaaacaa acagaaagcg ttggcggcag cactgggcca gattgagaaa      60
caatttggta aaggctccat catgcgcctg ggtgaagacc gttccatgga tgtggaaacc     120
atctctaccg ttcgctttc actggatatc gcgcttgggg caggtggtct gccgatgggc     180
cgtatcgtcg aaatctacgg accggaatct tccggtaaaa ccacgctgac gctgcaggtg     240
atcgccgcag cgcagcgtga aggtaaaacc tgtgcgtttta tcgatgctga acacgcgctg     300
gacccaatct acgcacgtaa actgggcgtc gatatcgaca acctgctgtg ctcccagccg     360
gacaccggcg agcaggcact ggaaatctgt gacgccctgg cgcgttctgg cgcagtagac     420
gttatcgtcg ttgactccgt ggcggcactg acgccgaaag cggaaatcga aggcgaaatc     480
ggcgactctc acatgggcct tgcggcacgt atgatgagcc aggcgatgcg taagctggcg     540
ggtaacctga agcagtccaa cacgctgctg atcttcatca accagatccg tatgaaaatt     600
ggtgtgatgt tcggtaaccc ggaaaccact accggtggta acgcgctgaa attctacgcc     660
tctgttcgtc tcgacatccg tcgtatcggc gcggtgaaag agggcgaaaa cgtggtgggt     720
agcgaaaccc gcgtgaaagt ggtgaagaac aaaatcgctg cgccgtttaa acaggctgaa     780
ttccagatcc tctacggcga aggtatcaac ttctacggcg aactggttga cctgggcgta     840
aaagagaagc tgatcgagaa agcaggcgcg tggtacagct acaaaggtga aagatcggt      900
cagggtaaag cgaatgcgac tgcctggctg aaagataacc cggaaccgcg aaagagatc     960
gagaagaaag tacgtgagtt gctgctgagc aacccgaact caacgccgga tttctctgta    1020
gatgatagcg aaggcgtagc agaaactaac gaagatttt aa                        1062
```

<210> SEQ ID NO 22
<211> LENGTH: 306
<212> TYPE: DNA
<213> ORGANISM: Escherichia coli

<400> SEQUENCE: 22

```
atgcagttta aggtttacac ctataaaaga gagagccgtt atcgtctgtt tgtggatgta      60
cagagtgata ttattgacac gcccgggcga cggatggtga tccccctggc cagtgcacgt     120
ctgctgtcag ataaagtctc ccgtgaactt tacccggtgg tgcatatcgg ggatgaaagc     180
tggcgcatga tgaccaccga tatggccagt gtgccggtct ccgttatcgg ggaagaagtg     240
gctgatctca gccaccgcga aaatgacatc aaaaacgcca ttaacctgat gttctgggga     300
atataa                                                                306

<210> SEQ ID NO 23
<211> LENGTH: 219
<212> TYPE: DNA
<213> ORGANISM: Escherichia coli

<400> SEQUENCE: 23
atgaagcagc gtattacagt gacagttgac agcgacagct atcagttgct caaggcatat      60
gatgtcaata tctccggtct ggtaagcaca accatgcaga atgaagcccg tcgtctgcgt     120
gccgaacgct ggaaagcgga aaatcaggaa gggatggctg aggtcgcccg gtttattgaa     180
atgaacggct cttttgctga cgagaacagg gactggtga                            219

<210> SEQ ID NO 24
<211> LENGTH: 59
<212> TYPE: DNA
<213> ORGANISM: Artificial Sequence
<220> FEATURE:
<223> OTHER INFORMATION: Synthetic Primer

<400> SEQUENCE: 24
gggggtaaat cccggcgctc atgacttcgc cttcttccca gaattcctgt tgacaatta       59

<210> SEQ ID NO 25
<211> LENGTH: 60
<212> TYPE: DNA
<213> ORGANISM: Artificial Sequence
<220> FEATURE:
<223> OTHER INFORMATION: Synthetic Primer

<400> SEQUENCE: 25
gttctgatta ttggaaatct tctttgccct ccagtgtgag cagcactgtc ctgctccttg      60

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
gtcttcaagt ggagcatcag                                                  20

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
accaggacta tccgtatgac                                                  20

<210> SEQ ID NO 28
<211> LENGTH: 35
```

<212> TYPE: DNA
<213> ORGANISM: Artificial Sequence
<220> FEATURE:
<223> OTHER INFORMATION: Synthetic Primer

<400> SEQUENCE: 28
ccaaacggaa cagatgaaga aggcgaagtc atgag                          35

<210> SEQ ID NO 29
<211> LENGTH: 35
<212> TYPE: DNA
<213> ORGANISM: Artificial Sequence
<220> FEATURE:
<223> OTHER INFORMATION: Synthetic Primer

<400> SEQUENCE: 29
gacttcgcct tcttcatctg ttccgtttgg cttcc                          35

<210> SEQ ID NO 30
<211> LENGTH: 21
<212> TYPE: DNA
<213> ORGANISM: Artificial Sequence
<220> FEATURE:
<223> OTHER INFORMATION: Synthetic Primer

<400> SEQUENCE: 30
gtaatggaaa gctggtagtc g                                         21

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
cagccgtaag tcttgatctc                                           20

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer

<400> SEQUENCE: 32
cagcaggcat gatccaagag                                           20

<210> SEQ ID NO 33
<211> LENGTH: 35
<212> TYPE: DNA
<213> ORGANISM: Artificial Sequence
<220> FEATURE:
<223> OTHER INFORMATION: Synthetic Primer

<400> SEQUENCE: 33
tttgccctcc agtgtgaaga aggcgaagtc atgag                          35

<210> SEQ ID NO 34
<211> LENGTH: 39
<212> TYPE: DNA
<213> ORGANISM: Artificial Sequence
<220> FEATURE:
<223> OTHER INFORMATION: Synthetic Primer

<400> SEQUENCE: 34
ctcatgactt cgccttcttc acactggagg gcaaagaag      39

<210> SEQ ID NO 35
<211> LENGTH: 48502
<212> TYPE: DNA
<213> ORGANISM: Unknown
<220> FEATURE:
<223> OTHER INFORMATION: Enterobacteria phage lambda

<400> SEQUENCE: 35

| | | |
|---|---|---|
| gggcggcgac ctcgcgggtt ttcgctattt atgaaaattt tccggtttaa ggcgtttccg | 60 |
| ttcttcttcg tcataactta atgtttttat ttaaaatacc ctctgaaaag aaaggaaacg | 120 |
| acaggtgctg aaagcgaggc tttttggcct ctgtcgtttc ctttctctgt ttttgtccgt | 180 |
| ggaatgaaca atggaagtca acaaaaagca gctggctgac attttcggtg cgagtatccg | 240 |
| taccattcag aactggcagg aacagggaat gcccgttctg cgaggcggtg gcaagggtaa | 300 |
| tgaggtgctt tatgactctg ccgccgtcat aaaatggtat gccgaaaggg atgctgaaat | 360 |
| tgagaacgaa aagctgcgcc gggaggttga agaactgcgg caggcagcg aggcagatct | 420 |
| ccagccagga actattgagt acgaacgcca tcgacttacg cgtgcgcagg ccgacgcaca | 480 |
| ggaactgaag aatgccagag actccgctga agtggtggaa accgcattct gtactttcgt | 540 |
| gctgtcgcgg atcgcaggtg aaattgccag tattctcgac gggctccccc tgtcggtgca | 600 |
| gcggcgtttt ccggaactgg aaaaccgaca tgttgatttc ctgaaacggg atatcatcaa | 660 |
| agccatgaac aaagcagccg cgctggatga actgataccg gggttgctga gtgaatatat | 720 |
| cgaacagtca ggttaacagg ctgcggcatt ttgtccgcgc cgggcttcgc tcactgttca | 780 |
| ggccggagcc acagaccgcc gttgaatggg cgatgctaa ttactatctc ccgaaagaat | 840 |
| ccgcatacca ggaagggcgc tgggaaacac tgcccttca gcgggccatc atgaatgcga | 900 |
| tgggcagcga ctacatccgt gaggtgaatg tggtgaagtc tgcccgtgtc ggttattcca | 960 |
| aaatgctgct gggtgtttat gcctacttta tagagcataa gcagcgcaac acccttatct | 1020 |
| ggttgccgac ggatggtgat gccgagaact ttatgaaaac ccacgttgag ccgactattc | 1080 |
| gtgatattcc gtcgctgctg cgcgctggcc cgtggtatgg caaaaagcac cgggataaca | 1140 |
| cgctcaccat gaagcgtttc actaatgggc gtggcttctg gtgcctgggc ggtaaagcgg | 1200 |
| caaaaaacta ccgtgaaaag tcggtggatg tggcgggtta tgatgaactt gctgcttttg | 1260 |
| atgatgatat tgaacaggaa ggctctccga cgttcctggg tgacaagcgt attgaaggct | 1320 |
| cggtctggcc aaagtccatc cgtggctcca cgccaaaagt gagaggcacc tgtcagattg | 1380 |
| agcgtgcagc cagtgaatcc ccgcatttta tgcgttttca tgttgcctgc ccgcattgcg | 1440 |
| gggaggagca gtatcttaaa tttgcgcgaca aagagacgcc gtttggcctc aaatggacgc | 1500 |
| cggatgaccc ctccagcgtg ttttatctct gcgagcataa tgcctgcgtc atccgccagc | 1560 |
| aggagctgga ctttactgat gcccgttata tctgcgaaaa gaccgggatc tggaccccgtg | 1620 |
| atggcattct ctggttttcg tcatccggtg aagagattga gccacctgac agtgtgacct | 1680 |
| ttcacatctg gacagcgtac agcccgttca ccacctgggt gcagattgtc aaagactgga | 1740 |
| tgaaaacgaa aggggatacg ggaaaacgta aaaccttcgt aaacaccacg ctcggtgaga | 1800 |
| cgtgggaggc gaaaattggc gaacgtccgg atgctgaagt gatggcagag cggaaagagc | 1860 |
| attattcagc gcccgttcct gaccgtgtgg cttacctgac cgccggtatc gactcccagc | 1920 |
| tggaccgcta cgaaatgcgc gtatgggat ggggccggg tgaggaaagc tggctgattg | 1980 |
| accggcagat tattatgggc cgccacgacg atgaacagac gctgctgcgt gtggatgagg | 2040 |

```
ccatcaataa aacctatacc cgccggaatg gtgcagaaat gtcgatatcc cgtatctgct    2100
gggatactgg cgggattgac ccgaccattg tgtatgaacg ctcgaaaaaa catgggctgt    2160
tccgggtgat ccccattaaa ggggcatccg tctacggaaa gccggtggcc agcatgccac    2220
gtaagcgaaa caaaaacggg gtttaccttta ccgaaatcgg tacggatacc gcgaaagagc    2280
agatttataa ccgcttcaca ctgacgccgg aaggggatga accgcttccc ggtgccgttc    2340
acttcccgaa taacccggat attttttgatc tgaccgaagc gcagcagctg actgctgaag    2400
agcaggtcga aaatgggtg gatggcagga aaaaatact gtgggacagc aaaaagcgac    2460
gcaatgaggc actcgactgc ttcgtttatg cgctggcggc gctgcgcatc agtatttccc    2520
gctggcagct ggatctcagt gcgctgctgg cgagcctgca ggaagaggat ggtgcagcaa    2580
ccaacaagaa aacactggca gattacgccc gtgccttatc cggagaggat gaatgacgcg    2640
acaggaagaa cttgccgctg cccgtgcggc actgcatgac ctgatgacag gtaaacgggt    2700
ggcaacagta cagaaagacg gacgaagggt ggagtttacg gccacttccg tgtctgacct    2760
gaaaaaatat attgcagagc tggaagtgca gaccggcatg acacagcgac gcaggggacc    2820
tgcaggattt tatgtatgaa aacgcccacc attcccaccc ttctggggcc ggacggcatg    2880
acatcgctgc gcgaatatgc cggttatcac ggcggtggca gcggatttgg agggcagttg    2940
cggtcgtgga acccaccgag tgaaagtgtg gatgcagccc tgttgcccaa ctttacccgt    3000
ggcaatgccc gcgcagacga tctggtacgc aataacggct atgccgccaa cgccatccag    3060
ctgcatcagg atcatatcgt cgggtctttt ttccggctca gtcatcgccc aagctggcgc    3120
tatctgggca tcggggagga agaagcccgt gccttttccc gcgaggttga agcggcatgg    3180
aaagagtttg ccgaggatga ctgctgctgc attgacgttg agcgaaaacg cacgtttacc    3240
atgatgattc gggaaggtgt ggccatgcac gcctttaacg gtgaactgtt cgttcaggcc    3300
acctgggata ccagttcgtc gcggcttttc cggacacagt tccggatggt cagcccgaag    3360
cgcatcagca acccgaacaa taccggcgac agccggaact gccgtgccgg tgtgcagatt    3420
aatgacagcg gtgcggcgct gggatattac gtcagcgagg acgggtatcc tggctggatg    3480
ccgcagaaat ggacatggat accccgtgag ttacccggcg ggcgcgcctc gttcattcac    3540 gttttttgaac ccgtggagga cgggcagact cgcggtgcaa atgtgtttta cagcgtgatg    3600
gagcagatga agatgctcga cacgctgcag aacacgcagc tgcagagcgc cattgtgaag    3660
gcgatgtatg ccgccaccat tgagagtgag ctggatacgc agtcagcgat ggattttatt    3720
ctgggcgcga acagtcagga gcagcgggaa aggctgaccg gctggattgg tgaaattgcc    3780
gcgtattacg ccgcagcgcc ggtccggctg ggaggcgcaa aagtaccgca cctgatgccg    3840
ggtgactcac tgaacctgca gacggctcag gatacggata acggctactc cgtgtttgag    3900
cagtcactgc tgcggtatat cgctgccggg ctgggtgtct cgtatgagca gctttcccgg    3960
aattacgccc agatgagcta ctccacggca cgggccagtg cgaacgagtc gtgggcgtac    4020
tttatggggc ggcgaaaatt cgtcgcatcc cgtcaggcga gccagatgtt tctgtgctgg    4080
ctggaagagg ccatcgttcg ccgcgtggtg acgttacctt caaaagcgcg cttcagtttt    4140
caggaagccc gcagtgcctg ggggaactgc gactggatag gctccggtcg tatggccatc    4200
gatggtctga agaagttca ggaagcggtg atgctgatag aagccggact gagtacctac    4260
gagaaagagt gcgcaaaacg cggtgacgac tatcaggaaa ttttttgccca gcaggtccgt    4320 gaaacgatgg agcgccgtgc agccggtctt aaaccgcccg cctgggcggc tgcagcattt    4380
```

```
gaatccgggc tgcgacaatc aacagaggag gagaagagtg acagcagagc tgcgtaatct    4440
cccgcatatt gccagcatgg cctttaatga gccgctgatg cttgaacccg cctatgcgcg    4500
ggttttcttt tgtgcgcttg caggccagct tgggatcagc agcctgacgg atgcggtgtc    4560
cggcgacagc ctgactgccc aggaggcact cgcgacgctg gcattatccg gtgatgatga    4620
cggaccacga caggcccgca gttatcaggt catgaacggc atcgccgtgc tgccggtgtc    4680
cggcacgctg gtcagccgga cgcgggcgct gcagccgtac tcggggatga ccggttacaa    4740
cggcattatc gcccgtctgc aacaggctgc cagcgatccg atggtggacg gcattctgct    4800
cgatatggac acgcccggcg ggatggtggc gggggcattt gactgcgctg acatcatcgc    4860
ccgtgtgcgt gacataaaac cggtatgggc gcttgccaac gacatgaact gcagtgcagg    4920
tcagttgctt gccagtgccg cctcccggcg tctggtcacg cagaccgccc ggacaggctc    4980
catcggcgtc atgatggctc acagtaatta cggtgctgcg ctggagaaac agggtgtgga    5040
aatcacgctg atttacagcg gcagccataa ggtggatggc aacccctaca gccatcttcc    5100
ggatgacgtc cgggagacac tgcagtcccg gatggacgca acccgccaga tgtttgcgca    5160
gaaggtgtcg gcatataccg gcctgtccgt gcaggttgtg ctggataccg aggctgcagt    5220
gtacagcggt caggaggcca ttgatgccgg actggctgat gaacttgtta acagcaccga    5280
tgcgatcacc gtcatgcgtg atgcactgga tgcacgtaaa tcccgtctct caggagggcg    5340
aatgaccaaa gagactcaat caacaactgt ttcagccact gcttcgcagg ctgacgttac    5400
tgacgtggtg ccagcgacgg agggcgagaa cgccagcgcg gcgcagccgg acgtgaacgc    5460
gcagatcacc gcagcggttg cggcagaaaa cagccgcatt atggggatcc tcaactgtga    5520
ggaggctcac ggacgcgaag aacaggcacg cgtgctggca gaaaccccg gtatgaccgt    5580 gaaaacggcc cgccgcattc tggccgcagc accacagagt gcacaggcgc gcagtgacac    5640
tgcgctggat cgtctgatgc aggggcacc ggcaccgctg gctgcaggta acccggcatc    5700
tgatgccgtt aacgatttgc tgaacacacc agtgtaaggg atgtttatga cgagcaaaga    5760
aacctttacc cattaccagc cgcagggcaa cagtgacccg gctcataccg caaccgcgcc    5820
cggcggattg agtgcgaaag cgcctgcaat gaccccgctg atgctggaca cctccagccg    5880
taagctggtt gcgtgggatg gcaccaccga cggtgctgcc gttggcattc ttgcggttgc    5940
tgctgaccag accagcacca cgctgacgtt ctacaagtcc ggcacgttcc gttatgagga    6000
tgtgctctgg ccggaggctg ccagcgacga gacgaaaaaa cggaccgcgt tgccggaac    6060 ggcaatcagc atcgtttaac tttacccttc atcactaaag gccgcctgtg cggcttttt    6120 tacgggattt ttttatgtcg atgtacacaa ccgcccaact gctggcggca aatgagcaga    6180
aatttaagtt tgatccgctg tttctgcgtc tcttttccg tgagagctat cccttcacca    6240
cggagaaagt ctatctctca caaattccgg gactggtaaa catggcgctg tacgtttcgc    6300
cgattgtttc cggtgaggtt atccgttccc gtggcggctc cacctctgaa tttacgccgg    6360
gatatgtcaa gccgaagcat gaagtgaatc cgcagatgac cctgcgtcgc ctgccggatg    6420
aagatccgca gaatctggcg gacccggctt accgccgccg tcgcatcatc atgcagaaca    6480
tgcgtgacga agagctggcc attgctcagg tcgaagagat gcaggcagtt tctgccgtgc    6540
ttaagggcaa atacaccatg accggtgaag ccttcgatcc ggttgaggtg gatatgggcc    6600
gcagtgagga gaataacatc acgcagtccg gcggcacgga gtggagcaag cgtgacaagt    6660
ccacgtatga cccgaccgac gatatcgaag cctacgcgct gaacgccagc ggtgtggtga    6720
atatcatcgt gttcgatccg aaaggctggg cgctgttccg ttccttcaaa gccgtcaagg    6780
```

-continued

```
agaagctgga tacccgtcgt ggctctaatt ccgagctgga gacagcggtg aaagacctgg   6840
gcaaagcggt gtcctataag gggatgtatg gcgatgtggc catcgtcgtg tattccggac   6900
agtacgtgga aaacggcgtc aaaaagaact tcctgccgga caacacgatg gtgctgggga   6960
acactcaggc acgcggtctg cgcacctatg gctgcattca ggatgcggac gcacagcgcg   7020
aaggcattaa cgcctctgcc cgttacccga aaaactgggt gaccaccggc gatccggcgc   7080
gtgagttcac catgattcag tcagcaccgc tgatgctgct ggctgaccct gatgagttcg   7140
tgtccgtaca actggcgtaa tcatggccct tcggggccat tgtttctctg tggaggagtc   7200
catgacgaaa gatgaactga ttgcccgtct ccgctcgctg ggtgaacaac tgaaccgtga   7260
tgtcagcctg acggggacga aagaagaact ggcgctccgt gtggcagagc tgaaagagga   7320
gcttgatgac acggatgaaa ctgccggtca ggacacccct ctcagccggg aaaatgtgct   7380
gaccggacat gaaaatgagg tgggatcagc gcagccggat accgtgattc tggatacgtc   7440
tgaactggtc acggtcgtgg cactggtgaa gctgcatact gatgcacttc acgccacgcg   7500
ggatgaacct gtggcatttg tgctgccggg aacggcgttt cgtgtctctg ccggtgtggc   7560
agccgaaatg acagagcgcg gcctggccag aatgcaataa cgggaggcgc tgtggctgat   7620
ttcgataacc tgttcgatgc tgccattgcc cgcgccgatg aaacgatacg cgggtacatg   7680
ggaacgtcag ccaccattac atccggtgag cagtcaggtg cggtgatacg tggtgttttt   7740
gatgaccctg aaaatatcag ctatgccgga cagggcgtgc gcgttgaagg ctccagcccg   7800 tccctgttg tccggactga tgaggtgcgg cagctgcggc gtggagacac gctgaccatc   7860
ggtgaggaaa atttctgggt agatcgggtt cgccggatg atggcggaag ttgtcatctc   7920
tggcttggac ggggcgtacc gcctgccgtt aaccgtcgcc gctgaaaggg ggatgtatgg   7980
ccataaaagg tcttgagcag gccgttgaaa acctcagccg tatcagcaaa acggcggtgc   8040
ctggtgccgc cgcaatggcc attaaccgcg ttgcttcatc cgcgtatatcg cagtcggcgt   8100 cacaggttgc ccgtgagaca aaggtacgcc ggaaactggt aaaggaaagg gccaggctga   8160
aaagggccac ggtcaaaaat ccgcaggcca gaatcaaagt taaccggggg gatttgcccg   8220
taatcaagct gggtaatgcg cgggttgtcc tttcgcgccg caggcgtcgt aaaaaggggc   8280
agcgttcatc cctgaaaggt ggcggcagcg tgcttgtggt gggtaaccgt cgtattcccg   8340
gcgcgtttat tcagcaactg aaaaatggcc ggtggcatgt catgcagcgt gtggctggga   8400
aaaaccgtta ccccattgat gtggtgaaaa tcccgatggc ggtgccgctg accacggcgt   8460
ttaaacaaaa tattgagcgg atacggcgtg aacgtcttcc gaaagagctg gctatgcgc   8520 tgcagcatca actgaggatg gtaataaagc gatgaaacat actgaactcc gtgcagccgt   8580
actggatgca ctggagaagc atgacaccgg ggcgacgttt tttgatggtc gccccgctgt   8640
ttttgatgag gcggattttc cggcagttgc cgtttatctc accggcgctg aatacacggg   8700
cgaagagctg gacagcgata cctggcaggc ggagctgcat atcgaagttt tcctgcctgc   8760
tcaggtgccg gattcagagc tggatgcgtg gatggagtcc ggatttatc cggtgatgag   8820 cgatatcccg gcactgtcag atttgatcac cagtatggtg ccagcggct atgactaccg   8880 gcgcgacgat gatgcgggct tgtggagttc agccgatctg acttatgtca ttacctatga   8940
aatgtgagga cgctatgcct gtaccaaatc ctacaatgcc ggtgaaaggt gccgggacca   9000
ccctgtgggt ttataagggg agcggtgacc cttacgcgaa tccgctttca gacgttgact   9060
ggtcgcgtct ggcaaaagtt aaagacctga cgcccggcga actgaccgct gagtcctatg   9120
```

-continued

```
acgacagcta tctcgatgat gaagatgcag actggactgc gaccgggcag gggcagaaat   9180
ctgccggaga taccagcttc acgctggcgt ggatgcccgg agagcagggg cagcaggcgc   9240
tgctggcgtg gtttaatgaa ggcgatacco gtgcctataa aatccgcttc ccgaacggca   9300
cggtcgatgt gttccgtggc tgggtcagca gtatcggtaa ggcggtgacg gcgaaggaag   9360
tgatcacccg cacggtgaaa gtcaccaatg tgggacgtcc gtcgatggca gaagatcgca   9420
gcacggtaac agcggcaacc ggcatgaccg tgacgcctgc cagcacctcg gtggtgaaag   9480
ggcagagcac cacgctgacc gtggccttcc agccggaggg cgtaaccgac aagagctttc   9540
gtgcggtgtc tgcggataaa acaaaagcca ccgtgtcggt cagtggtatg accatcaccg   9600
tgaacggcgt tgctgcaggc aaggtcaaca ttccggttgt atccggtaat ggtgagtttg   9660
ctgcggttgc agaaattacc gtcaccgcca gttaatccgg agagtcagcg atgttcctga   9720
aaaccgaatc atttgaacat aacggtgtga ccgtcacgct ttctgaactg tcagccctgc   9780
agcgcattga gcatctcgcc ctgatgaaac ggcaggcaga acaggcggag tcagacagca   9840
accggaagtt tactgtggaa gacgccatca gaaccggcgc gtttctggtg gcgatgtccc   9900
tgtggcataa ccatccgcag aagacgcaga tgccgtccat gaatgaagcc gttaaacaga   9960
ttgagcagga agtgcttacc acctggccca cggaggcaat ttctcatgct gaaaacgtgg  10020
tgtaccggct gtctggtatg tatgagtttg tggtgaataa tgcccctgaa cagacagagg  10080
acgccgggcc cgcagagcct gtttctgcgg gaaagtgttc gacggtgagc tgagttttgc  10140
cctgaaactg gcgcgtgaga tggggcgacc cgactggcgt gccatgcttg ccgggatgtc  10200
atccacggag tatgccgact ggcaccgctt ttacagtacc cattattttc atgatgttct  10260
gctggatatg cactttttcc ggctgacgta caccgtgctc agcctgtttt tcagcgatcc  10320
ggatatgcat ccgctggatt tcagtctgct gaaccggcgc gaggctgacg aagagcctga  10380
agatgatgtg ctgatgcaga aagcggcagg gcttgccgga ggtgtccgct ttggcccgga  10440
cgggaatgaa gttatccccg cttccccgga tgtggcggac atgacggagg atgacgtaat  10500
gctgatgaca gtatcagaag ggatcgcagg aggagtccgg tatggctgaa ccggtaggcg  10560
atctggtcgt tgatttgagt ctggatgcgg ccagatttga cgagcagatg ccagagtca   10620
ggcgtcattt ttctggtacg gaaagtgatg cgaaaaaaac agcggcagtc gttgaacagt  10680
cgctgagccg acaggcgctg gctgcacaga aagcggggat ttccgtcggg cagtataaag  10740
ccgccatgcg tatgctgcct gcacagttca ccgacgtggc cacgcagctt gcaggcgggc  10800
aaagtccgtg gctgatcctg ctgcaacagg gggcaggt gaaggactcc ttcggcggga   10860
tgatccccat gttcaggggg cttgccggtg cgatcaccct gccgatggtg ggggccacct  10920
cgctggcggt ggcgaccggt gcgctggcgt atgcctggta tcagggcaac tcaaccctgt  10980
ccgatttcaa caaaacgctg gtcctttccg gcaatcaggc gggactgacg gcagatcgta  11040
tgctggtcct gtccagagcc gggcaggcgg cagggctgac gtttaaccag accagcgagt  11100
cactcagcgc actggttaag gcgggggtaa gcggtgaggc tcagattgcg tccatcagcc  11160
agagtgtggc gcgtttctcc tctgcatccg gcgtggaggt ggacaaggtc gctgaagcct  11220
tcgggaagct gaccacagac ccgacgtcgg ggctgacggc gatggctcgc cagttccata  11280
acgtgtcggc ggagcagatt gcgtatgttg ctcagttgca gcgttccggc gatgaagccg  11340
gggcattgca ggcggcgaac gaggccgcaa cgaaagggtt tgatgaccag acccgccgcc  11400
tgaaagagaa catgggcacg ctggagacct gggcagacag gactgcgcgg gcattcaaat  11460
ccatgtggga tgcggtgctg gatattggtc gtcctgatac cgcgcaggag atgctgatta  11520
```

| | | | | |
|---|---|---|---|---|
| aggcagaggc | tgcgtataag | aaagcagacg | acatctggaa | tctgcgcaag gatgattatt 11580 |
| ttgttaacga | tgaagcgcgg | gcgcgttact | gggatgatcg | tgaaaaggcc cgtcttgcgc 11640 |
| ttgaagccgc | ccgaaagaag | gctgagcagc | agactcaaca | ggacaaaaat gcgcagcagc 11700 |
| agagcgatac | cgaagcgtca | cggctgaaat | ataccgaaga | ggcgcagaag gcttacgaac 11760 |
| ggctgcagac | gccgctggag | aaatataccg | cccgtcagga | gaactgaac aaggcactga 11820 |
| aagacgggaa | aatcctgcag | gcggattaca | acacgctgat | ggcggcggcg aaaaaggatt 11880 |
| atgaagcgac | gctgaaaaag | ccgaaacagt | ccagcgtgaa | ggtgtctgcg gcgatcgtc 11940 |
| aggaagacag | tgctcatgct | gccctgctga | cgcttcaggc | agaactccgg acgctggaga 12000 |
| agcatgccgg | agcaaatgag | aaaatcagcc | agcagcgccg | ggatttgtgg aaggcggaga 12060 |
| gtcagttcgc | ggtactggag | gaggcggcgc | aacgtcgcca | gctgtctgca caggagaaat 12120 |
| ccctgctggc | gcataaagat | gagacgctgg | agtacaaacg | ccagctggct gcacttggcg 12180 |
| acaaggttac | gtatcaggag | cgcctgaacg | cgctggcgca | gcaggcggat aaattcgcac 12240 |
| agcagcaacg | ggcaaaacgg | gccgccattg | atgcgaaaag | ccggggctg actgaccggc 12300 |
| aggcagaacg | ggaagccacg | gaacagcgcc | tgaaggaaca | gtatggcgat aatccgctgg 12360 |
| cgctgaataa | cgtcatgtca | gagcagaaaa | agacctgggc | ggctgaagac cagcttcgcg 12420 |
| ggaactggat | ggcaggcctg | aagtccggct | ggagtgagtg | ggaagagagc gccacggaca 12480 |
| gtatgtcgca | ggtaaaaagt | gcagccacgc | agacctttga | tggtattgca cagaatatgg 12540 |
| cggcgatgct | gaccggcagt | gagcagaact | ggcgcagctt | cacccgttcc gtgctgtcca 12600 |
| tgatgacaga | aattctgctt | aagcaggcaa | tggtggggat | tgtcgggagt atcggcagcg 12660 |
| ccattggcgg | ggctgttggt | ggcggcgcat | ccgcgtcagg | cggtacagcc attcaggccg 12720 |
| ctgcggcgaa | attccatttt | gcaaccggag | gatttacggg | aaccggcggc aaatatgagc 12780 |
| cagcggggat | tgttcaccgt | ggtgagtttg | tcttcacgaa | ggaggcaacc agccggattg 12840 |
| gcgtggggaa | tctttaccgg | ctgatgcgcg | gctatgccac | cggcggttat gtcggtacac 12900 |
| cgggcagcat | ggcagacagc | cggtcgcagg | cgtccgggac | gtttgagcag aataaccatg 12960 |
| tggtgattaa | caacgacggc | acgaacgggc | agataggtcc | ggctgctctg aaggcggtgt 13020 |
| atgacatggc | ccgcaagggt | gcccgtgatg | aaattcagac | acagatgcgt gatggtggcc 13080 |
| tgttctccgg | aggtggacga | tgaagacctt | ccgctgaaa | gtgaacccg gtatggatgt 13140 |
| ggcttcggtc | ccttctgtaa | gaaaggtgcg | ctttggtgat | ggctattctc agcgagcgcc 13200 |
| tgccgggctg | aatgccaacc | tgaaaacgta | cagcgtgacg | ctttctgtcc cccgtgagga 13260 |
| ggccacggta | ctggagtcgt | ttctggaaga | gcacgggggc | tggaaatcct ttctgtggac 13320 |
| gccgccttat | gagtggcggc | agataaaggt | gacctgcgca | aaatggtcgt cgcgggtcag 13380 |
| tatgctgcgt | gttgagttca | gcgcagagtt | tgaacaggtg | gtgaactgat gcaggatatc 13440 |
| cggcaggaaa | cactgaatga | atgcacccgt | gcggagcagt | cggccagcgt ggtgctctgg 13500 |
| gaaatcgacc | tgacagaggt | cggtggagaa | cgttattttt | tctgtaatga gcagaacgaa 13560 |
| aaaggtgagc | cggtcacctg | gcaggggcga | cagtatcagc | cgtatcccat tcaggggagc 13620 |
| ggttttgaac | tgaatggcaa | aggcaccagt | acgcgcccca | cgctgacggt ttctaacctg 13680 |
| tacggtatgg | tcaccgggat | ggcggaagat | atgcagagtc | tggtcggcgg aacggtggtc 13740 |
| cggcgtaagg | tttacgcccg | ttttctggat | gcggtgaact | cgtcaacgg aaacagttac 13800 |
| gccgatccgg | agcaggaggt | gatcagccgc | tggcgcattg | agcagtgcag cgaactgagc 13860 |

```
gcggtgagtg cctcctttgt actgtccacg ccgacggaaa cggatggcgc tgttttccg    13920
ggacgtatca tgctggccaa cacctgcacc tggacctatc gcggtgacga gtgcggttat   13980
agcggtccgg ctgtcgcgga tgaatatgac cagccaacgt ccgatatcac gaaggataaa   14040
tgcagcaaat gcctgagcgg ttgtaagttc cgcaataacg tcggcaactt tggcggcttc   14100
ctttccatta acaaactttc gcagtaaatc ccatgacaca gacagaatca gcgattctgg   14160
cgcacgcccg gcgatgtgcg ccagcggagt cgtgcggctt cgtggtaagc acgccggagg   14220
gggaaagata tttcccctgc gtgaatatct ccggtgagcc ggaggctatt tccgtatgtc   14280
gccggaagac tggctgcagg cagaaatgca gggtgagatt gtggcgctgg tccacagcca   14340
ccccggtggt ctgccctggc tgagtgaggc cgaccggcgg ctgcaggtgc agagtgattt   14400
gccgtggtgg ctggtctgcc gggggacgat tcataagttc cgctgtgtgc cgcatctcac   14460
cgggcggcgc tttgagcacg gtgtgacgga ctgttacaca ctgttccggg atgcttatca   14520
tctggcgggg attgagatgc cggactttca tcgtgaggat gactggtggc gtaacggcca   14580
gaatctctat ctggataatc tggaggcgac ggggctgtat caggtgccgt tgtcagcggc   14640
acagccgggc gatgtgctgc tgtgctgttt tggttcatca gtgccgaatc acgccgcaat   14700
ttactgcgga gacggcgagc tgctgcacca tattcctgaa caactgagca aacgagagag   14760
gtacaccgac aaatggcagc gacgcacaca ctccctctgg cgtcaccggg catggcgcgc   14820
atctgccttt acgggatttt acaacgattt ggtcgccgca tcgaccttcg tgtgaaaacg   14880
ggggctgaag ccatccgggc actggccaca cagctcccgg cgtttcgtca gaaactgagc   14940
gacggctggt atcaggtacg gattgccggg cgggacgtca gcacgtccgg gttaacggcg   15000
cagttacatg agactctgcc tgatggcgct gtaattcata ttgttcccag agtcgccggg   15060
gccaagtcag gtgcgtatt ccagattgtc ctgggggctg ccgccattgc cggatcattc   15120
tttaccgccg gagccaccct tgcagcatgg ggggcagcca ttggggccgg tggtatgacc   15180
ggcatcctgt tttctctcgg tgccagtatg gtgctcggtg gtgtggcgca gatgctggca   15240
ccgaaagcca gaactccccg tatacagaca acggataacg gtaagcagaa cacctatttc   15300
tcctcactgg ataacatggt tgcccagggc aatgttctgc ctgttctgta cggggaaatg   15360
cgcgtggggt cacgcgtggt ttctcaggag atcagcacgg cagacgaagg ggacggtggt   15420
caggttgtgg tgattggtcg ctgatgcaaa atgttttatg tgaaccgcc tgcgggcggt   15480
tttgtcattt atggagcgtg aggaatgggt aaaggaagca gtaaggggca taccccgcgc   15540
gaagcgaagg acaacctgaa gtccacgcag ttgctgagtg tgatcgatgc catcagcgaa   15600
gggccgattg aaggtccggt ggatggctta aaaagcgtgc tgctgaacag tacgccggtg   15660
ctggacactg aggggaatac caacatatcc ggtgtcacgg tggtgttccg ggctggtgag   15720
caggagcaga ctccgccgga gggatttgaa tcctccggct ccgagacggt gctgggtacg   15780
gaagtgaaat atgacacgcc gatcacccgc accattacgt ctgcaaacat cgaccgtctg   15840
cgctttacct tcggtgtaca ggcactggtg gaaaccacct caaagggtga caggaatccg   15900
tcggaagtcc gcctgctggt tcagatacaa cgtaacggtg gctgggtgac ggaaaaagac   15960
atcaccatta agggcaaaac cacctcgcag tatctggcct cggtggtgat gggtaacctg   16020
ccgccgcgcc cgtttaatat ccggatgcgc aggatgacgc cggacagcac cacagaccag   16080
ctgcagaaca aaacgctctg gtcgtcatac actgaaatca tcgatgtgaa acagtgctac   16140
ccgaacacgg cactggtcgg cgtgcaggtg gactcggagc agttcggcag ccagcaggtg   16200
agccgtaatt atcatctgcg cgggcgtatt ctgcaggtgc cgtcgaacta taacccgcag   16260
```

```
acgcggcaat acagcggtat ctgggacgga acgtttaaac cggcatacag caacaacatg   16320
gcctggtgtc tgtgggatat gctgacccat ccgcgctacg gcatgggaa acgtcttggt    16380
gcggcggatg tggataaatg ggcgctgtat gtcatcggcc agtactgcga ccagtcagtg   16440
ccggacggct ttggcggcac ggagccgcgc atcacctgta atgcgtacct gaccacacag   16500
cgtaaggcgt gggatgtgct cagcgatttc tgctcggcga tgcgctgtat gccggtatgg   16560
aacgggcaga cgctgacgtt cgtgcaggac cgaccgtcgg ataagacgtg gacctataac   16620
cgcagtaatg tggtgatgcc ggatgatggc gcgccgttcc gctacagctt cagcgccctg   16680
aaggaccgcc ataatgccgt tgaggtgaac tggattgacc cgaacaacgg ctgggagacg   16740
gcgacagagc ttgttgaaga tacgcaggcc attgcccgtt acggtcgtaa tgttacgaag   16800
atggatgcct ttggctgtac cagccggggg caggcacacc gcgccgggct gtggctgatt   16860
aaaacagaac tgctggaaac gcagaccgtg gatttcagcg tcggcgcaga agggcttcgc   16920
catgtaccgg gcgatgttat tgaaatctgc gatgatgact atgccggtat cagcaccggt   16980
ggtcgtgtgc tggcggtgaa cagccagacc cggacgctga cgctcgaccg tgaaatcacg   17040
ctgccatcct ccggtaccgc gctgataagc ctggttgacg gaagtggcaa tccggtcagc   17100
gtggaggttc agtccgtcac cgacggcgtg aaggtaaaag tgagccgtgt tcctgacggt   17160
gttgctgaat acagcgtatg ggagctgaag ctgccgacgc tgcgccagcg actgttccgc   17220
tgcgtgagta tccgtgagaa cgacgacggc acgtatgcca tcaccgccgt gcagcatgtg   17280
ccggaaaaag aggccatcgt ggataacggg gcgcactttg acggcgaaca gagtggcacg   17340
gtgaatggtg tcacgccgcc agcggtgcag cacctgaccg cagaagtcac tgcagacagc   17400
ggggaatatc aggtgctggc gcgatgggac acaccgaagg tggtgaaggg cgtgagtttc   17460
ctgctccgtc tgaccgtaac agcggacgac ggcagtgagc ggctggtcag cacggcccgg   17520
acgacggaaa ccacataccg cttcacgcaa ctggcgctgg ggaactacag gctgacagtc   17580
cgggcggtaa atgcgtgggg gcagcagggc gatccggcgt cggtatcgtt ccggattgcc   17640
gcaccggcag caccgtcgag gattgagctg acgcccgggct attttcagat aaccgccacg   17700
ccgcatcttg ccgtttatga cccgacggta cagtttgagt tctggttctc ggaaaagcag   17760
attgcggata tcagacaggt tgaaaccagc acgcgttatc ttggtacggc gctgtactgg   17820
atagccgcca gtatcaatat caaaccgggc catgattatt acttttatat ccgcagtgtg   17880
aacaccgttg gcaaatcggc attcgtggag gccgtcggtc gggcgagcga tgatgcggaa   17940
ggttacctgg atttttttcaa aggcaagata accgaatccc atctcggcaa ggagctgctg   18000
gaaaaagtcg agctgacgga ggataacgcc agcagactgg aggagttttc gaaagagtgg   18060
aaggatgcca gtgataagtg gaatgccatg tgggctgtca aaattgagca gaccaaagac   18120
ggcaaacatt atgtcgcggg tattggcctc agcatggagg acacggagga aggcaaactg   18180
agccagtttc tggttgccgc caatcgtatc gcatttattg acccggcaaa cgggaatgaa   18240
acgccgatgt ttgtggcgca gggcaaccag atattcatga cgacgtgtt cctgaagcgc    18300
ctgacggccc ccaccattac cagcggcggc aatcctccgg ccttttccct gacaccggac   18360
ggaaagctga ccgctaaaaa tgcggatatc agtggcagtg tgaatgcgaa ctccgggacg   18420
ctcagtaatg tgacgatagc tgaaaactgt acgataaacg gtacgctgag ggcggaaaaa   18480
atcgtcgggg acattgtaaa ggcggcgagc gcggcttttc cgcgccagcg tgaaagcagt   18540
gtggactggc cgtcaggtac ccgtactgtc accgtgaccg atgaccatcc ttttgatcgc   18600
```

```
cagatagtgg tgcttccgct gacgtttcgc ggaagtaagc gtactgtcag cggcaggaca    18660
acgtattcga tgtgttatct gaaagtactg atgaacggtg cggtgattta tgatggcgcg    18720
gcgaacgagg cggtacaggt gttctcccgt attgttgaca tgccagcggg tcggggaaac    18780
gtgatcctga cgttcacgct tacgtccaca cggcattcgg cagatattcc gccgtatacg    18840
tttgccagcg atgtgcaggt tatggtgatt aagaaacagg cgctgggcat cagcgtggtc    18900
tgagtgtgtt acagaggttc gtccgggaac gggcgtttta ttataaaaca gtgagaggtg    18960
aacgatgcgt aatgtgtgta ttgccgttgc tgtctttgcc gcacttgcgg tgacagtcac    19020
tccggcccgt gcggaaggtg gacatggtac gtttacggtg ggctattttc aagtgaaacc    19080
gggtacattg ccgtcgttgt cgggcgggga taccggtgtg agtcatctga aagggattaa    19140
cgtgaagtac cgttatgagc tgacggacag tgtgggggtg atggcttccc tggggttcgc    19200
cgcgtcgaaa aagagcagca cagtgatgac cggggaggat acgtttcact atgagagcct    19260
gcgtggacgt tatgtgagcg tgatggccgg accggtttta caaatcagta agcaggtcag    19320
tgcgtacgcc atgccggag tggctcacag tcggtggtcc ggcagtacaa tggattaccg    19380
taagacggaa atcactcccg ggtatatgaa agagacgacc actgccaggg acgaaagtgc    19440
aatgcggcat acctcagtgg cgtggagtgc aggtatacag attaatccgg cagcgtccgt    19500
cgttgttgat attgcttatg aaggctccgg cagtggcgac tggcgtactg acggattcat    19560
cgttggggtc ggttataaat tctgattagc caggtaacac agtgttatga cagcccgccg    19620
gaaccggtgg gctttttttgt ggggtgaata tggcagtaaa gatttcagga gtcctgaaag    19680
acggcacagg aaaaccggta cagaactgca ccattcagct gaaagccaga cgtaacagca    19740
ccacggtggt ggtgaacacg gtgggctcag agaatccgga tgaagccggg cgttacagca    19800
tggatgtgga gtacggtcag tacagtgtca tcctgcaggt tgacggtttt ccaccatcgc    19860
acgccgggac catcaccgtg tatgaagatt cacaaccggg gacgctgaat gattttctct    19920
gtgccatgac ggaggatgat gcccggccgg aggtgctgcg tcgtcttgaa ctgatggtgg    19980
aagaggtggc gcgtaacgcg tccgtggtgg cacagagtac ggcagacgcg aagaaatcag    20040
ccggcgatgc cagtgcatca gctgctcagg tcgcggccct tgtgactgat gcaactgact    20100
cagcacgcgc cgccagcacg tccgccggac aggctgcatc gtcagctcag gaagcgtcct    20160
ccggcgcaga gcggcatca gcaaaggcca ctgaagcgga aaaaagtgcc gcagccgcag    20220
agtcctcaaa aaacgcggcg gccaccagtg ccggtgcggc gaaaacgtca gaaacgaatg    20280
ctgcagcgtc acaacaatca gccgccacgt ctgcctccac cgcggccacg aaagcgtcag    20340
aggccgccac ttcagcacga gatgcggtgg cctcaaaaga ggcagcaaaa tcatcagaaa    20400
cgaacgcatc atcaagtgcc ggtcgtgcag cttcctcggc aacggcggca gaaaattctg    20460
ccagggcggc aaaaacgtcc gagacgaatg ccaggtcatc tgaaacagca gcggaacgga    20520
gcgcctctgc cgcggcagac gcaaaaacag cggcggcggg gagtgcgtca acggcatcca    20580
cgaaggcgac agaggctgcg ggaagtgcgg tatcagcatc gcagagcaaa agtgcggcag    20640
aagcggcggc aatacgtgca aaaaattcgg caaaacgtgc agaagatata gcttcagctg    20700
tcgcgcttga ggatgcggac acaacgagaa aggggatagt gcagctcagc agtgcaacca    20760
acagcacgtc tgaaacgctt gctgcaacgc caaaggcggt taaggtggta atggatgaaa    20820
cgaacagaaa agcccactgg acagtccggc actgaccgga acgccaacag caccaaccgc    20880
gctcagggga acaaacaata cccagattgc gaacaccgct tttgtactgg ccgcgattgc    20940
agatgttatc gacgcgtcac ctgacgcact gaatacgctg aatgaactgg ccgcagcgct    21000
```

```
cgggaatgat ccagattttg ctaccaccat gactaacgcg cttgcgggta aacaaccgaa    21060
gaatgcgaca ctgacggcgc tggcagggct ttccacggcg aaaaataaat taccgtattt    21120
tgcggaaaat gatgccgcca gcctgactga actgactcag gttggcaggg atattctggc    21180
aaaaaattcc gttgcagatg ttcttgaata ccttggggcc ggtgagaatt cggccttcc     21240 ggcaggtgcg ccgatcccgt ggccatcaga tatcgttccg tctggctacg tcctgatgca    21300
ggggcaggcg tttgacaaat cagcctaccc aaaacttgct gtcgcgtatc catcgggtgt    21360
gcttcctgat atgcgaggct ggacaatcaa ggggaaaccc gccagcggtc gtgctgtatt    21420
gtctcaggaa caggatggaa ttaagtcgca cacccacagt gccagtgcat ccggtacgga    21480
tttggggacg aaaaccacat cgtcgtttga ttacgggacg aaaacaacag gcagtttcga    21540
ttacggcacc aaatcgacga ataacacggg ggctcatgct cacagtctga gcggttcaac    21600
aggggccgcg ggtgctcatg cccacacaag tggtttaagg atgaacagtt ctggctggag    21660
tcagtatgga acagcaacca ttacaggaag tttatccaca gttaaaggaa ccagcacaca    21720
gggtattgct tatttatcga aaacggacag tcagggcagc cacagtcact cattgtccgg    21780
tacagccgtg agtgccggtg cacatgcgca tacagttggt attggtgcgc accagcatcc    21840
ggttgttatc ggtgctcatg cccattcttt cagtattggt tcacacggac acaccatcac    21900
cgttaacgct gcgggtaacg cggaaaaacac cgtcaaaaac attgcattta actatattgt    21960
gaggcttgca taatggcatt cagaatgagt gaacaaccac ggaccataaa aatttataat    22020
ctgctggccg gaactaatga atttattggt gaaggtgacg catatattcc gcctcatacc    22080
ggtctgcctg caaacagtac cgatattgca ccgccagata ttccggctgg ctttgtggct    22140
gttttcaaca gtgatgaggc atcgtggcat ctcgttgaag accatcgggg taaaaccgtc    22200
tatgacgtgg cttccggcga cgcgttattt atttctgaac tcggtccgtt accggaaaat    22260
tttacctggt tatcgccggg aggggaatat cagaagtgga acggcacagc ctgggtgaag    22320
gatacggaag cagaaaaact gttccggatc cgggaggcgg aagaaacaaa aaaaagcctg    22380
atgcaggtag ccagtgagca tattgcgccg cttcaggatg ctgcagatct ggaaattgca    22440
acgaaggaag aaacctcgtt gctggaagcc tggaagaagt atcgggtgtt gctgaaccgt    22500
gttgatacat caactgcacc tgatattgag tggcctgctg tccctgttat ggagtaatcg    22560
ttttgtgata tgccgcagaa acgttgtatg aaataacgtt ctgcgttag ttagtatatt     22620 gtaaagctga gtattggttt atttggcgat tattatcttc aggagaataa tggaagttct    22680
atgactcaat tgttcatagt gtttacatca ccgccaattg cttttaagac tgaacgcatg    22740
aaatatggtt tttcgtcatg ttttgagtct gctgttgata tttctaaagt cggtttttt     22800 tcttcgtttt ctctaactat tttccatgaa atacattttt gattattatt tgaatcaatt    22860
ccaattacct gaagtctttc atctataatt ggcattgtat gtattggttt attggagtag    22920
atgcttgctt ttctgagcca tagctctgat atccaaatga agccataggc atttgttatt    22980
ttggctctgt cagctgcata acgccaaaaa atatatttat ctgcttgatc ttcaaatgtt    23040
gtattgatta aatcaattgg atggaattgt ttatcataaa aaattaatgt ttgaatgtga    23100
taaccgtcct ttaaaaaagt cgtttctgca agcttggctg tatagtcaac taactcttct    23160
gtcgaagtga tatttttagg cttatctacc agttttagac gctctttaat atcttcagga    23220
attattttat tgtcatattg tatcatgcta aatgacaatt tgcttatgga gtaatctttt    23280
aattttaaat aagttattct cctggcttca tcaaataaag agtcgaatga tgttggcgaa    23340
```

```
atcacatcgt cacccattgg attgtttatt tgtatgccaa gagagttaca gcagttatac   23400
attctgccat agattatagc taaggcatgt aataattcgt aatcttttag cgtattagcg   23460
acccatcgtc tttctgattt aataatagat gattcagtta aatatgaagg taatttcttt   23520
tgtgcaagtc tgactaactt ttttatacca atgtttaaca tactttcatt tgtaataaac   23580
tcaatgtcat tttcttcaat gtaagatgaa ataagagtag cctttgcctc gctatacatt   23640
tctaaatcgc cttgttttc tatcgtattg cgagaatttt tagcccaagc cattaatgga   23700 tcattttcc atttttcaat aacattattg ttataccaaa tgtcatatcc tataatctgg   23760
tttttgtttt tttgaataat aaatgttact gttcttgcgg tttggaggaa ttgattcaaa   23820
ttcaagcgaa ataattcagg gtcaaaatat gtatcaatgc agcatttgag caagtgcgat   23880
aaatctttaa gtcttctttc ccatggtttt ttagtcataa aactctccat tttgataggt   23940
tgcatgctag atgctgatat attttagagg tgataaaatt aactgcttaa ctgtcaatgt   24000
aatacaagtt gtttgatctt tgcaatgatt cttatcagaa accatatagt aaattagtta   24060
cacaggaaat ttttaatatt attattatca ttcattatgt attaaaatta gagttgtggc   24120
ttggctctgc taacacgttg ctcataggag atatggtaga gccgcagaca cgtcgtatgc   24180
aggaacgtgc tgcggctggc tggtgaactt ccgatagtgc gggtgttgaa tgatttccag   24240
ttgctaccga ttttacatat ttttttgcatg agagaatttg taccacctcc caccgaccat   24300
ctatgactgt acgccactgt ccctaggact gctatgtgcc ggagcggaca ttacaaacgt   24360
ccttctcggt gcatgccact gttgccaatg acctgcctag gaattggtta gcaagttact   24420
accggatttt gtaaaaacag ccctcctcat ataaaaagta ttcgttcact tccgataagc   24480
gtcgtaattt tctatctttc atcatattct agatccctct gaaaaaatct tccgagtttg   24540
ctaggcactg atacataact cttttccaat aattggggaa gtcattcaaa tctataatag   24600
gtttcagatt tgcttcaata aattctgact gtagctgctg aaacgttgcg gttgaactat   24660
atttccttat aacttttacg aaagagtttc tttgagtaat cacttcactc aagtgcttcc   24720
ctgcctccaa acgatacctg ttagcaatat ttaatagctt gaaatgatga agagctctgt   24780
gtttgtcttc ctgcctccag ttcgccgggc attcaacata aaaactgata gcacccggag   24840
ttccggaaac gaaatttgca tatacccatt gctcacgaaa aaaaatgtcc ttgtcgatat   24900
agggatgaat cgcttggtgt acctcatcta ctgcgaaaac ttgacctttc tctcccatat   24960
tgcagtcgcg gcacgatgga actaaattaa taggcatcac cgaaaattca ggataatgtg   25020
caataggaag aaaatgatct atattttttg tctgtcctat atcaccacaa aatggacatt   25080
tttcacctga tgaaacaagc atgtcatcgt aatatgttct agcgggtttg ttttatctc   25140 ggagattatt ttcataaagc ttttctaatt taacctttgt caggttacca actactaagg   25200
ttgtaggctc aagagggtgt gtcctgtcgt aggtaaataa ctgacctgtc gagcttaata   25260
ttctatattg ttgttctttc tgcaaaaaag tggggaagtg agtaatgaaa ttatttctaa   25320
catttatctg catcatacct tccgagcatt tattaagcat ttcgctataa gttctcgctg   25380
gaagaggtag tttttttcatt gtactttacc ttcatctctg ttcattatca tcgcttttaa   25440
aacggttcga ccttctaatc ctatctgacc attataattt tttagaatgg tttcataaga   25500
aagctctgaa tcaacggact gcgataataa gtggtggtat ccagaatttg tcacttcaag   25560
taaaaacacc tcacgagtta aaacacctaa gttctcaccg aatgtctcaa tatccggacg   25620
gataatattt attgcttctc ttgaccgtag gactttccac atgcaggatt ttggaacctc   25680
ttgcagtact actggggaat gagttgcaat tattgctaca ccattgcgtg catcgagtaa   25740
```

-continued

```
gtcgcttaat gttcgtaaaa aagcagagag caaaggtgga tgcagatgaa cctctggttc    25800
atcgaataaa actaatgact tttcgccaac gacatctact aatcttgtga tagtaaataa    25860
aacaattgca tgtccagagc tcattcgaag cagatatttc tggatattgt cataaaacaa    25920
tttagtgaat ttatcatcgt ccacttgaat ctgtggttca ttacgtctta actcttcata    25980
tttagaaatg aggctgatga gttccatatt tgaaaagttt tcatcactac ttagtttttt    26040
gatagcttca agccagagtt gtcttttttct atctactctc atacaaccaa taaatgctga    26100
aatgaattct aagcggagat cgcctagtga ttttaaacta ttgctggcag cattcttgag    26160
tccaatataa aagtattgtg taccttttgc tgggtcaggt tgttctttag gaggagtaaa    26220
aggatcaaat gcactaaacg aaactgaaac aagcgatcga aaatatccct ttgggattct    26280
tgactcgata agtctattat tttcagagaa aaaatattca ttgttttctg ggttggtgat    26340
tgcaccaatc attccattca aaattgttgt tttaccacac ccattccgcc cgataaaagc    26400
atgaatgttc gtgctgggca tagaattaac cgtcacctca aaaggtatag ttaaatcact    26460
gaatccggga gcacttttttc tattaaatga aaagtggaaa tctgacaatt ctggcaaacc    26520
atttaacaca cgtgcgaact gtccatgaat ttctgaaaga gttacccctc taagtaatga    26580
ggtgttaagg acgctttcat tttcaatgtc ggctaatcga tttggccata ctactaaatc    26640
ctgaatagct ttaagaaggt tatgtttaaa accatcgctt aatttgctga gattaacata    26700
gtagtcaatg ctttcaccta aggaaaaaaa catttcaggg agttgactga atttttatc     26760 tattaatgaa taagtgctta cttcttcttt ttgacctaca aaaccaattt taacatttcc    26820
gatatcgcat ttttcaccat gctcatcaaa gacagtaaga taaaacattg taacaaagga    26880
atagtcattc caaccatctg ctcgtaggaa tgccttattt ttttctactg caggaatata    26940
cccgcctctt tcaataacac taaactccaa catatagtaa cccttaatttt tattaaaata   27000 accgcaatttt atttggcggc aacacaggat ctctcttttta agttactctc tattacatac   27060
gttttccatc taaaaattag tagtattgaa cttaacgggg catcgtattg tagttttcca    27120
tatttagctt tctgcttcct tttggataac ccactgttat tcatgttgca tggtgcactg    27180
tttataccaa cgatatagtc tattaatgca tatatagtat cgccgaacga ttagctcttc    27240
aggcttctga agaagcgttt caagtactaa taagccgata gatagccacg gacttcgtag    27300 ccattttttca taagtgttaa cttccgctcc tcgctcataa cagacattca ctacagttat    27360
ggcggaaagg tatgcatgct gggtgtgggg aagtcgtgaa agaaaagaag tcagctgcgt    27420
cgtttgacat cactgctatc ttcttactgg ttatgcaggt cgtagtgggt ggcacacaaa    27480
gctttgcact ggattgcgag gctttgtgct tctctggagt gcgacaggtt tgatgacaaa    27540
aaattagcgc aagaagacaa aaatcacctt gcgctaatgc tctgttacag gtcactaata    27600
ccatctaagt agttgattca tagtgactgc atatgttgtg ttttacagta ttatgtagtc    27660 tgtttttttat gcaaaatcta atttaatata ttgatattta tatcattta cgtttctcgt    27720 tcagcttttt tatactaagt tggcattata aaaaagcatt gcttatcaat ttgttgcaac    27780
gaacaggtca ctatcagtca aaataaaatc attatttgat ttcaattttg tcccactccc    27840
tgcctctgtc atcacgatac tgtgatgcca tggtgtccga cttatgcccg agaagatgtt    27900
gagcaaactt atcgcttatc tgcttctcat agagtcttgc agacaaactg cgcaactcgt    27960
gaaaggtagg cggatcccct tcgaggaaa gacctgatgc ttttcgtgcg cgcataaaat    28020
accttgatac tgtgccggat gaaagcggtt cgcgacgagt agatgcaatt atggtttctc    28080
```

```
cgccaagaat ctctttgcat ttatcaagtg tttccttcat tgatattccg agagcatcaa   28140
tatgcaatgc tgttgggatg gcaatttttta cgcctgtttt gctttgctcg acataaagat   28200
atccatctac gatatcagac cacttcattt cgcataaatc accaactcgt tgcccggtaa   28260
caacagccag ttccattgca agtctgagcc aacatggtga tgattctgct gcttgataaa   28320
ttttcaggta ttcgtcagcc gtaagtcttg atctccttac ctctgatttt gctgcgcgag   28380
tggcagcgac atggtttgtt gttatatggc cttcagctat tgcctctcgg aatgcatcgc   28440
tcagtgttga tctgattaac ttggctgacg ccgccttgcc ctcgtctatg tatccattga   28500
gcattgccgc aatttctttt gtggtgatgt cttcaagtgg agcatcaggc agacccctcc   28560
ttattgcttt aattttgctc atgtaattta tgagtgtctt ctgcttgatt cctctgctgg   28620
ccaggatttt ttcgtagcga tcaagccatg aatgtaacgt aacggaatta tcactgttga   28680
ttctcgctgt cagaggcttg tgtttgtgtc ctgaaaataa ctcaatgttg gcctgtatag   28740
cttcagtgat tgcgattcgc ctgtctctgc ctaatccaaa ctctttaccc gtccttgggt   28800
ccctgtagca gtaatatcca ttgtttctta tataaaggtt aggggtaaa tcccggcgct   28860
catgacttcg ccttcttccc atttctgatc ctcttcaaaa ggccacctgt tactggtcga   28920
tttaagtcaa cctttaccgc tgattcgtgg aacagatact ctcttccatc cttaaccgga   28980
ggtgggaata tcctgcattc ccgaacccat cgacgaactg tttcaaggct tcttggacgt   29040
cgctggcgtg cgttccactc ctgaagtgtc aagtacatcg caaagtctcc gcaattacac   29100
gcaagaaaaa accgccatca ggcggcttgg tgttctttca gttcttcaat tcgaatattg   29160
gttacgtctg catgtgctat ctgcgcccat atcatccagt ggtcgtagca gtcgttgatg   29220
ttctccgctt cgataactct gttgaatggc tctccattcc attctcctgt gactcggaag   29280
tgcatttatc atctccataa aacaaaaccc gccgtagcga gttcagataa aataaatccc   29340
cgcgagtgcg aggattgtta tgtaatattg ggtttaatca tctatatgtt ttgtacagag   29400
agggcaagta tcgtttccac cgtactcgtg ataataattt tgcacggtat cagtcatttc   29460
tcgcacattg cagaatgggg atttgtcttc attagactta taaaccttca tggaatattt   29520
gtatgccgac tctatatcta taccttcatc tacataaaca ccttcgtgat gtctgcatgg   29580
agacaagaca ccggatctgc acaacattga taacgcccaa tcttttttgct cagactctaa   29640
ctcattgata ctcatttata aactccttgc aatgtatgtc gtttcagcta acggtatca   29700
gcaatgttta tgtaaagaaa cagtaagata atactcaacc cgatgtttga gtacggtcat   29760
catctgacac tacagactct ggcatcgctg tgaagacgac gcgaaattca gcattttcac   29820
aagcgttatc ttttacaaaa ccgatctcac tctcctttga tgcgaatgcc agcgtcagac   29880
atcatatgca gatactcacc tgcatcctga acccattgac ctccaacccc gtaatagcga   29940
tgcgtaatga tgtcgatagt tactaacggg tcttgttcga ttaactgccg cagaaactct   30000
tccaggtcac cagtgcagtg cttgataaca ggagtcttcc caggatggcg aacaacaaga   30060
aactggtttc cgtcttcacg gacttcgttg ctttccagtt tagcaatacg cttactccca   30120
tccgagataa caccttcgta atactcacgc tgctcgttga gttttgattt gctgtttca   30180
agctcaacac gcagttttccc tactgttagc gcaatatcct cgttctcctg gtcgcggcgt   30240
ttgatgtatt gctggtttct ttcccgttca tccagcagtt ccagcacaat cgatggtgtt   30300
accaattcat ggaaaaggtc tgcgtcaaat ccccagtcgt catgcattgc ctgctctgcc   30360
gcttcacgca gtgcctgaga gttaatttcg ctcacttcga acctctctgt ttactgataa   30420
gttccagatc ctcctggcaa cttgcacaag tccgacaacc ctgaacgacc aggcgtcttc   30480
```

```
gttcatctat cggatcgcca cactcacaac aatgagtggc agatatagcc tggtggttca   30540
ggcggcgcat ttttattgct gtgttgcgct gtaattcttc tatttctgat gctgaatcaa   30600
tgatgtctgc catctttcat taatccctga actgttggtt aatacgcttg agggtgaatg   30660
cgaataataa aaaaggagcc tgtagctccc tgatgatttt gcttttcatg ttcatcgttc   30720
cttaaagacg ccgtttaaca tgccgattgc caggcttaaa tgagtcggtg tgaatcccat   30780
cagcgttacc gtttcgcggt gcttcttcag tacgctacgg caaatgtcat cgacgttttt   30840
atccggaaac tgctgtctgg cttttttttga tttcagaatt agcctgacgg gcaatgctgc   30900
gaagggcgtt ttcctgctga ggtgtcattg aacaagtccc atgtcggcaa gcataagcac   30960
acagaatatg aagcccgctg ccagaaaaat gcattccgtg gttgtcatac ctggtttctc   31020
tcatctgctt ctgctttcgc caccatcatt tccagctttt gtgaaaggga tgcggctaac   31080
gtatgaaatt cttcgtctgt ttctactggt attggcacaa acctgattcc aatttgagca   31140
aggctatgtg ccatctcgat actcgttctt aactcaacag aagatgcttt gtgcatacag   31200
cccctcgttt attatttatc tcctcagcca gccgctgtgc tttcagtgga tttcggataa   31260
cagaaaggcc gggaaatacc cagcctcgct ttgtaacgga gtagacgaaa gtgattgcgc   31320
ctacccggat attatcgtga ggatgcgtca tcgccattgc tccccaaata caaaaccaat   31380
ttcagccagt gcctcgtcca tttttttcgat gaactccggc acgatctcgt caaaactcgc   31440
catgtacttt tcatcccgct caatcacgac ataatgcagg ccttcacgct tcatacgcgg   31500
gtcatagttg gcaaagtacc aggcattttt tcgcgtcacc cacatgctgt actgcacctg   31560
ggccatgtaa gctgacttta tggcctcgaa accaccgagc cggaacttca tgaaatcccg   31620
ggaggtaaac gggcatttca gttcaaggcc gttgccgtca ctgcataaac catcgggaga   31680
gcaggcggta cgcatacttt cgtcgcgata gatgatcggg gattcagtaa cattcacgcc   31740
ggaagtgaat tcaaacaggg ttctggcgtc gttctcgtac tgttttcccc aggccagtgc   31800
tttagcgtta acttccggag ccacaccggt gcaaacctca gcaagcaggg tgtggaagta   31860
ggacattttc atgtcaggcc acttctttcc ggagcggggt tttgctatca cgttgtgaac   31920
ttctgaagcg gtgatgacgc cgagccgtaa tttgtgccac gcatcatccc cctgttcgac   31980
agctctcaca tcgatcccgg tacgctgcag gataatgtcc ggtgtcatgc tgccaccttc   32040
tgctctgcgg ctttctgttt caggaatcca agagcttttta ctgcttcggc ctgtgtcagt   32100
tctgacgatg cacgaatgtc gcggcgaaat atctgggaac agagcggcaa taagtcgtca   32160
tcccatgttt tatccagggc gatcagcaga gtgttaatct cctgcatggt ttcatcgtta   32220
accggagtga tgtcgcgttc cggctgacgt tctgcagtgt atgcagtatt ttcgacaatg   32280
cgctcggctt catccttgtc atagatacca gcaaatccga aggccagacg ggcacactga   32340
atcatggctt tatgacgtaa catccgtttg ggatgcgact gccacggccc cgtgatttct   32400
ctgccttcgc gagttttgaa tggttcgcgg cggcattcat ccatccattc ggtaacgcag   32460
atcggatgat tacggtcctt gcggtaaatc cggcatgtac aggattcatt gtcctgctca   32520
aagtccatgc catcaaactg ctggttttca ttgatgatgc gggaccagcc atcaacgccc   32580
accaccggaa cgatgccatt ctgcttatca ggaaaggcgt aaatttcttt cgtccacgga   32640
ttaaggccgt actggttggc aacgatcagt aatgcgatga actgcgcatc gctggcatca   32700
cctttaaatg ccgtctggcg aagagtggtg atcagttcct gtgggtcgac agaatccatg   32760
ccgacacgtt cagccagctt cccagccagc gttgcgagtg cagtactcat tcgttttata   32820
```

```
cctctgaatc aatatcaacc tggtggtgag caatggtttc aaccatgtac cggatgtgtt  32880
ctgccatgcg ctcctgaaac tcaacatcgt catcaaacgc acgggtaatg gattttttgc  32940
tggccccgtg gcgttgcaaa tgatcgatgc atagcgattc aaacaggtgc tggggcaggc  33000
ctttttccat gtcgtctgcc agttctgcct ctttctcttc acgggcgagc tgctggtagt  33060
gacgcgccca gctctgagcc tcaagacgat cctgaatgta ataagcgttc atggctgaac  33120
tcctgaaata gctgtgaaaa tatcgcccgc gaaatgccgg gctgattagg aaaacaggaa  33180
agggggttag tgaatgcttt tgcttgatct cagtttcagt attaatatcc attttttata  33240
agcgtcgacg gcttcacgaa acatcttttc atcgccaata aaagtggcga tagtgaattt  33300
agtctggata gccataagtg tttgatccat tctttgggac tcctggctga ttaagtatgt  33360
cgataaggcg tttccatccg tcacgtaatt tacgggtgat tcgttcaagt aaagattcgg  33420
aagggcagcc agcaacaggc caccctgcaa tggcatattg catggtgtgc tccttattta  33480
tacataacga aaaacgcctc gagtgaagcg ttattggtat gcggtaaaac cgcactcagg  33540
cggccttgat agtcatatca tctgaatcaa atattcctga tgtatcgata tcggtaattc  33600
ttattccttc gctaccatcc attggaggcc atccttcctg accatttcca tcattccagt  33660
cgaactcaca cacaacacca tatgcattta agtcgcttga aattgctata agcagagcat  33720
gttgcgccag catgattaat acagcattta atacagagcc gtgtttattg agtcggtatt  33780
cagagtctga ccagaaatta ttaatctggt gaagtttttc ctctgtcatt acgtcatggt  33840
cgatttcaat ttctattgat gctttccagt cgtaatcaat gatgtatttt ttgatgtttg  33900
acatctgttc atatcctcac agataaaaaa tcgccctcac actggagggc aaagaagatt  33960
tccaataatc agaacaagtc ggctcctgtt tagttacgag cgacattgct ccgtgtattc  34020
actcgttgga atgaatacac agtgcagtgt ttattctgtt atttatgcca aaaataaagg  34080
ccactatcag gcagctttgt tgttctgttt accaagttct ctggcaatca ttgccgtcgt  34140
tcgtattgcc catttatcga catatttccc atcttccatt acaggaaaca tttcttcagg  34200
cttaaccatg cattccgatt gcagcttgca tccattgcat cgcttgaatt gtccacacca  34260 ttgatttta tcaatagtcg tagtcatacg gatagtcctg gtattgttcc atcacatcct  34320
gaggatgctc ttcgaactct tcaaattctt cttccatata tcaccttaaa tagtggattg  34380
cggtagtaaa gattgtgcct gtctttaac cacatcaggc tcggtggttc tcgtgtaccc  34440
ctacagcgag aaatcggata aactattaca accctacag tttgatgagt atagaaatgg  34500
atccactcgt tattctcgga cgagtgttca gtaatgaacc tctggagaga accatgtata  34560
tgatcgttat ctgggttgga cttctgcttt taagcccaga taactggcct gaatatgtta  34620
atgagagaat cggtattcct catgtgtggc atgttttcgt cttgctctt gcattttcgc  34680 tagcaattaa tgtgcatcga ttatcagcta ttgccagcgc cagatataag cgatttaagc  34740
taagaaaacg cattaagatg caaaacgata aagtgcgatc agtaattcaa aaccttacag  34800
aagagcaatc tatggttttg tgcgcagccc ttaatgaagg caggaagtat gtggttacat  34860
caaaacaatt cccatacatt agtgagttga ttgagcttgg tgtgttgaac aaaactttt  34920 cccgatggaa tggaaagcat atattattcc ctattgagga tatttactgg actgaattag  34980
ttgccagcta tgatccatat aatattgaga taaagccaag gccaatatct aagtaactag  35040
ataagaggaa tcgattttcc cttaattttc tggcgtccac tgcatgttat gccgcgttcg  35100
ccaggcttgc tgtaccatgt gcgctgatc ttgcgctcaa tacgttgcag gttgctttca  35160 atctgttgt ggtattcagc cagcactgta aggtctatcg gatttagtgc gctttctact  35220
```

```
cgtgatttcg gtttgcgatt cagcgagaga atagggcggt taactggttt tgcgcttacc   35280
ccaaccaaca ggggatttgc tgctttccat tgagcctgtt tctctgcgcg acgttcgcgg   35340
cggcgtgttt gtgcatccat ctggattctc ctgtcagtta gctttggtgg tgtgtggcag   35400
ttgtagtcct gaacgaaaac cccccgcgat tggcacattg gcagctaatc cggaatcgca   35460
cttacggcca atgcttcgtt tcgtatcaca caccccaaag ccttctgctt gaatgctgc    35520
ccttcttcag ggcttaattt ttaagagcgt caccttcatg gtggtcagtg cgtcctgctg   35580
atgtgctcag tatcaccgcc agtggtattt atgtcaacac cgccagagat aatttatcac   35640
cgcagatggt tatctgtatg tttttttatat gaatttattt tttgcagggg ggcattgttt  35700
ggtaggtgag agatctgaat tgctatgttt agtgagttgt atctatttat ttttcaataa   35760
atacaattgg ttatgtgttt tggggggcgat cgtgaggcaa agaaaacccg gcgctgaggc  35820
cgggttattc ttgttctctg gtcaaattat atagttggaa aacaaggatg catatatgaa   35880
tgaacgatgc agaggcaatg ccgatggcga tagtgggtat catgtagccg cttatgctgg   35940
aaagaagcaa taacccgcag aaaaacaaag ctccaagctc aacaaaacta agggcataga   36000
caataactac cgatgtcata tacccatact ctctaatctt ggccagtcgg cgcgttctgc   36060
ttccgattag aaacgtcaag gcagcaatca ggattgcaat catggttcct gcatatgatg   36120
acaatgtcgc cccaagacca tctctatgag ctgaaaaaga aacaccagga atgtagtggc   36180
ggaaaaggag atagcaaatg cttacgataa cgtaaggaat tattactatg taaacaccag   36240
gcatgattct gttccgcata attactcctg ataattaatc cttaactttg cccacctgcc   36300
ttttaaaaca ttccagtata tcactttttca ttcttgcgta gcaatatgcc atctcttcag  36360
ctatctcagc attggtgacc ttgttcagag gcgctgagag atggccttttt tctgatagat  36420
aatgttctgt taaaatatct ccggcctcat cttttgcccg caggctaatg tctgaaaatt   36480
gaggtgacgg gttaaaaata atatccttgg caaccttttt tatatccctt ttaaattttg   36540
gcttaatgac tatatccaat gagtcaaaaa gctccccttc aatatctgtt gcccctaaga   36600
cctttaatat atcgccaaat acaggtagct tggcttctac cttcaccgtt gttcggccga   36660
tgaaatgcat atgcataaca tcgtcttttgg tggttcccct catcagtggc tctatctgaa  36720
cgcgctctcc actgcttaat gacattcctt tcccgattaa aaaatctgtc agatcggatg   36780
tggtcggccc gaaaacagtt ctggcaaaac caatggtgtc gccttcaaca aacaaaaaag   36840
atgggaatcc caatgattcg tcatctgcga ggctgttctt aatatcttca actgaagctt   36900
tagagcgatt tatcttctga accagactct tgtcatttgt tttggtaaag agaaaagttt   36960
ttccatcgat tttatgaata tacaaataat tggagccaac ctgcaggtga tgattatcag   37020
ccagcagaga attaaggaaa acagacaggt ttattgagcg cttatctttc cctttatttt   37080
tgctgcggta agtcgcataa aaaccattct tcataattca atccatttac tatgttatgt   37140
tctgagggga gtgaaaattc ccctaattcg atgaagattc ttgctcaatt gttatcagct   37200
atgcgccgac cagaacacct tgccgatcag ccaaacgtct cttcaggcca ctgactagcg   37260
ataactttcc ccacaacgga acaactctca ttgcatggga tcattgggta ctgtgggttt   37320
agtggttgta aaaacacctg accgctatcc ctgatcagtt tcttgaaggt aaactcatca   37380
cccccaagtc tggctatgca gaaatcacct ggctcaacag cctgctcagg gtcaacgaga   37440
attaacattc cgtcaggaaa gcttggcttg gagcctgttg gtgcggtcat ggaattacct   37500
tcaacctcaa gccagaatgc agaatcactg gctttttttgg ttgtgcttac ccatctctcc   37560
```

```
gcatcacctt tggtaaaggt tctaagctca ggtgagaaca tccctgcctg aacatgagaa   37620
aaaacagggt actcatactc acttctaagt gacggctgca tactaaccgc ttcatacatc   37680
tcgtagattt ctctggcgat tgaagggcta aattcttcaa cgctaacttt gagaattttt   37740
gcaagcaatg cggcgttata agcatttaat gcattgatgc cattaaataa agcaccaacg   37800
cctgactgcc ccatccccat cttgtctgcg acagattcct gggataagcc aagttcattt   37860
ttcttttttt cataaattgc tttaaggcga cgtgcgtcct caagctgctc ttgtgttaat   37920
ggtttctttt ttgtgctcat acgttaaatc tatcaccgca agggataaat atctaacacc   37980
gtgcgtgttg actattttac ctctggcggt gataatggtt gcatgtacta aggaggttgt   38040
atggaacaac gcataaccct gaaagattat gcaatgcgct ttgggcaaac caagacagct   38100
aaagatctcg gcgtatatca agcgcgatc aacaaggcca ttcatgcagg ccgaaagatt   38160
tttttaacta taaacgctga tggaagcgtt tatgcggaag aggtaaagcc cttcccgagt   38220
aacaaaaaaa caacagcata ataaccccg ctcttacaca ttccagccct gaaaagggc    38280 atcaaattaa accacaccta tggtgtatgc atttatttgc atacattcaa tcaattgtta   38340
tctaaggaaa tacttacata tggttcgtgc aaacaaacgc aacgaggctc tacgaatcga   38400
gagtgcgttg cttaacaaaa tcgcaatgct tggaactgag aagacagcgg aagctgtggg   38460
cgttgataag tcgcagatca gcaggtggaa gagggactgg attccaaagt tctcaatgct   38520
gcttgctgtt cttgaatggg gggtcgttga cgacgacatg gctcgattgg cgcgacaagt   38580
tgctgcgatt ctcaccaata aaaaacgccc ggcggcaacc gagcgttctg aacaaatcca   38640
gatggagttc tgaggtcatt actggatcta tcaacaggag tcattatgac aaatacagca   38700
aaaatactca acttcggcag aggtaactt gccggacagg agcgtaatgt ggcagatctc   38760
gatgatggtt acgccagact atcaaatatg ctgcttgagg cttattcggg cgcagatctg   38820
accaagcgac agtttaaagt gctgcttgcc attctgcgta aaacctatgg gtggaataaa   38880
ccaatggaca gaatcaccga ttctcaactt agcgagatta caaagttacc tgtcaaacgg   38940
tgcaatgaag ccaagttaga actcgtcaga atgaatatta tcaagcagca aggcggcatg   39000
tttggaccaa ataaaaacat ctcagaatgg tgcatccctc aaaacgaggg aaaatcccct   39060
aaaacgaggg ataaaacatc cctcaaattg ggggattgct atccctcaaa acaggggggac   39120 acaaagaca ctattacaaa agaaaaaaga aagattatt cgtcagagaa ttctggcgaa   39180
tcctctgacc agccagaaaa cgacctttct gtggtgaaac cggatgctgc aattcagagc   39240
ggcagcaagt gggggacagc agaagacctg accgccgcag agtggatgtt tgacatggtg   39300
aagactatcg caccatcagc cagaaaaccg aattttgctg gtgggctaa cgatatccgc   39360 ctgatgcgtg aacgtgacgg acgtaaccac cgcgacatgt gtgtgctgtt ccgctgggca   39420
tgccaggaca acttctggtc cggtaacgtg ctgagcccgg ccaaactccg cgataagtgg   39480
acccaactcg aaatcaaccg taacaagcaa caggcaggcg tgacagccag caaaccaaaa   39540
ctcgacctga caaacacaga ctggatttac ggggtggatc tatgaaaaac atcgccgcac   39600
agatggttaa ctttgaccgt gagcagatgc gtcggatcgc caacaacatg ccggaacagt   39660
acgacgaaaa gccgcaggta cagcaggtag cgcagatcat caacggtgtg ttcagccagt   39720
tactggcaac tttcccggcg agcctggcta accgtgacca gaacgaagtg aacgaaatcc   39780
gtcgccagtg ggttctggct tttcggaaa acgggatcac cacgatggaa caggttaacg   39840
caggaatgcg cgtagcccgt cggcagaatc gaccatttct gccatcaccc gggcagtttg   39900
ttgcatggtg ccgggaagaa gcatccgtta ccgccggact gccaaacgtc agcgagctgg   39960
```

```
ttgatatggt ttacgagtat tgccggaagc gaggcctgta tccgatgcg gagtcttatc    40020 cgtggaaatc aaacgcgcac tactggctgg ttaccaacct gtatcagaac atgcgggcca    40080
atgcgcttac tgatgcggaa ttcgccgta aggccgcaga tgagcttgtc catatgactg     40140
cgagaattaa ccgtggtgag gcgatccctg aaccagtaaa acaacttcct gtcatgggcg    40200
gtagacctct aaatcgtgca caggctctgg cgaagatcgc agaaatcaaa gctaagttcg    40260
gactgaaagg agcaagtgta tgacgggcaa agaggcaatt attcattacc tggggacgca    40320
taatagcttc tgtgcgccgg acgttgccgc gctaacaggc gcaacagtaa ccagcataaa    40380
tcaggccgcg gctaaaatgg cacgggcagg tcttctggtt atcgaaggta aggtctggcg    40440
aacggtgtat taccggtttg ctaccaggga agaacgggaa ggaaagatga gcacgaacct    40500
ggtttttaag gagtgtcgcc agagtgccgc gatgaaacgg gtattggcgg tatatggagt    40560
taaaagatga ccatctacat tactgagcta ataacaggcc tgctggtaat cgcaggcctt    40620
tttatttggg ggagagggaa gtcatgaaaa aactaacctt tgaaattcga tctccagcac    40680
atcagcaaaa cgctattcac gcagtacagc aaatccttcc agacccaacc aaaccaatcg    40740
tagtaaccat tcaggaacgc aaccgcagct tagaccaaaa caggaagcta tgggcctgct    40800
taggtgacgt ctctcgtcag gttgaatggc atggtcgctg gctggatgca gaaagctgga    40860
agtgtgtgtt taccgcagca ttaaagcagc aggatgttgt tcctaacctt gccgggaatg    40920
gctttgtggt aataggccag tcaaccagca ggatgcgtgt aggcgaattt gcggagctat    40980
tagagcttat acaggcattc ggtacagagc gtggcgttaa gtggtcagac gaagcgagac    41040
tggctctgga gtggaaagcg agatggggag acagggctgc atgataaatg tcgttagttt    41100
ctccggtggc aggacgtcag catatttgct ctggctaatg gagcaaaagc gacgggcagg    41160
taaagacgtg cattacgttt tcatggatac aggttgtgaa catccaatga catatcggtt    41220
tgtcagggaa gttgtgaagt ctgggatat accgctcacc gtattgcagg ttgatatcaa    41280
cccggagctt ggacagccaa atggttatac ggtatgggaa ccaaaggata ttcagacgcg    41340
aatgcctgtt ctgaagccat ttatcgatat ggtaaagaaa tatggcactc catacgtcgg    41400
cggcgcgttc tgcactgaca gattaaaact cgttcccttc accaaatact gtgatgacca    41460
tttcgggcga gggaattaca ccacgtggat tggcatcaga gctgatgaac cgaagcggct    41520
aaagccaaag cctggaatca gatatcttgc tgaactgtca gactttgaga aggaagatat    41580
cctcgcatgg tggaagcaac aaccattcga tttgcaaata ccggaacatc tcggtaactg    41640
catattctgc attaaaaaat caacgcaaaa aatcggactt gcctgcaaag atgaggaggg    41700
attgcagcgt gttttaatg aggtcatcac gggatcccat gtgcgtgacg gacatcggga    41760
aacgccaaag gagattatgt accgaggaag aatgtcgctg gacggtatcg cgaaaatgta    41820
ttcagaaaat gattatcaag ccctgtatca ggacatggta cgagctaaaa gattcgatac    41880
cggctcttgt tctgagtcat gcgaaatatt tggaggcag cttgatttcg acttcggag    41940 ggaagctgca tgatgcgatg ttatcggtgc ggtgaatgca aagaagataa ccgcttccga    42000
ccaaatcaac cttactggaa tcgatggtgt ctccggtgtg aaagaacacc aacaggggtg    42060
ttaccactac cgcaggaaaa ggaggacgtg tggcagaca gcgacgaagt atcaccgaca    42120
taatctgcga aaactgcaaa taccttccaa cgaaacgcac cagaaataaa cccaagccaa    42180
tcccaaaaga atctgacgta aaaaccttca actacacggc tcacctgtgg gatatccggt    42240
ggctaagacg tcgtgcgagg aaaacaaggt gattgaccaa aatcgaagtt acgaacaaga    42300
```

```
aagcgtcgag cgagctttaa cgtgcgctaa ctgcggtcag aagctgcatg tgctggaagt    42360
tcacgtgtgt gagcactgct gcgcagaact gatgagcgat ccgaatagct cgatgcacga    42420
ggaagaagat gatggctaaa ccagcgcgaa gacgatgtaa aaacgatgaa tgccgggaat    42480
ggtttcaccc tgcattcgct aatcagtggt ggtgctctcc agagtgtgga accaagatag    42540
cactcgaacg acgaagtaaa gaacgcgaaa aagcggaaaa agcagcagag aagaaacgac    42600
gacgagagga gcagaaacag aaagataaac ttaagattcg aaaactcgcc ttaaagcccc    42660
gcagttactg gattaaacaa gcccaacaag ccgtaaacgc cttcatcaga gaaagagacc    42720
gcgacttacc atgtatctcg tgcggaacgc tcacgtctgc tcagtgggat gccggacatt    42780
accggacaac tgctgcggca cctcaactcc gatttaatga acgcaatatt cacaagcaat    42840
gcgtggtgtg caaccagcac aaaagcggaa atctcgttcc gtatcgcgtc gaactgatta    42900
gccgcatcgg gcaggaagca gtagacgaaa tcgaatcaaa ccataaccgc catcgctgga    42960
ctatcgaaga gtgcaaggcg atcaaggcag agtaccaaca gaaactcaaa gacctgcgaa    43020
atagcagaag tgaggccgca tgacgttctc agtaaaaacc attccagaca tgctcgttga    43080
agcatacgga aatcagacag aagtagcacg cagactgaaa tgtagtcgcg gtacggtcag    43140
aaaatacgtt gatgataaag acgggaaaat gcacgccatc gtcaacgacg ttctcatggt    43200
tcatcgcgga tggagtgaaa gagatgcgct attacgaaaa aattgatggc agcaaatacc    43260
gaaatatttg ggtagttggc gatctgcacg gatgctacac gaacctgatg aacaaactgg    43320
atacgattgg attcgacaac aaaaaagacc tgcttatctc ggtgggcgat ttggttgatc    43380
gtggtgcaga gaacgttgaa tgcctggaat taatcacatt cccctggttc agagctgtac    43440
gtggaaacca tgagcaaatg atgattgatg gcttatcaga gcgtggaaac gttaatcact    43500
ggctgcttaa tggcggtggc tggttctttta atctcgatta cgacaaagaa attctggcta    43560
aagctcttgc ccataaagca gatgaacttc cgttaatcat cgaactggtg agcaaagata    43620
aaaaatatgt tatctgccac gccgattatc cctttgacga atacgagttt ggaaagccag    43680
ttgatcatca gcaggtaatc tggaaccgcg aacgaatcag caactcacaa aacgggatcg    43740
tgaaagaaat caaaggcgcg gacacgttca tctttggtca tacgccagca gtgaaaccac    43800
tcaagtttgc caaccaaatg tatatcgata ccggcgcagt gttctgcgga aacctaacat    43860
tgattcaggt acagggagaa ggcgcatgag actcgaaagc gtagctaaat ttcattcgcc    43920
aaaaagcccg atgatgagcg actcaccacg ggccacggct tctgactctc tttccggtac    43980
tgatgtgatg gctgctatgg ggatggcgca atcacaagcc ggattcggta tggctgcatt    44040
ctgcggtaag cacgaactca gccagaacga caaacaaaag gctatcaact atctgatgca    44100
atttgcacac aaggtatcgg ggaaataccg tggtgtggca aagcttgaag gaaatactaa    44160
ggcaaaggta ctgcaagtgc tcgcaacatt cgcttatgcg gattattgcc gtagtgccgc    44220
gacgccgggg gcaagatgca gagattgcca tggtacaggc cgtgcggttg atattgccaa    44280
aacagagctg tgggggagag ttgtcgagaa agagtgcgga agatgcaaag gcgtcggcta    44340
ttcaaggatg ccagcaagcg cagcatatcg cgctgtgacg atgctaatcc caaaccttac    44400
ccaacccacc tggtcacgca ctgttaagcc gctgtatgac gctctggtgg tgcaatgcca    44460
caaagaagag tcaatcgcag acaacatttt gaatgcggtc acacgttagc agcatgattg    44520
ccacggatgg caacatatta acggcatgat attgacttat tgaataaaat tgggtaaatt    44580
tgactcaacg atgggttaat tcgctcgttg tggtagtgag atgaaaagag gcggcgctta    44640
ctaccgattc cgcctagttg gtcacttcga cgtatcgtct ggaactccaa ccatcgcagg    44700
```

```
cagagaggtc tgcaaaatgc aatcccgaaa cagttcgcag gtaatagtta gagcctgcat    44760
aacggtttcg ggattttta tatctgcaca acaggtaaga gcattgagtc gataatcgtg     44820
aagagtcggc gagcctggtt agccagtgct ctttccgttg tgctgaatta agcgaatacc    44880
ggaagcagaa ccggatcacc aaatgcgtac aggcgtcatc gccgcccagc aacagcacaa    44940
cccaaactga gccgtagcca ctgtctgtcc tgaattcatt agtaatagtt acgctgcggc    45000
cttttacaca tgaccttcgt gaaagcgggt ggcaggaggt cgcgctaaca acctcctgcc    45060
gttttgcccg tgcatatcgg tcacgaacaa atctgattac taaacacagt agcctggatt    45120
tgttctatca gtaatcgacc ttattcctaa ttaaatagag caaatcccct tattgggggt    45180
aagacatgaa gatgccagaa aaacatgacc tgttggccgc cattctcgcg gcaaaggaac    45240
aaggcatcgg ggcaatcctt gcgtttgcaa tggcgtacct tcgcggcaga tataatggcg    45300
gtgcgtttac aaaaacagta atcgacgcaa cgatgtgcgc cattatcgcc tggttcattc    45360
gtgaccttct cgacttcgcc ggactaagta gcaatctcgc ttatataacg agcgtgttta    45420
tcggctacat cggtactgac tcgattggtt cgcttatcaa acgcttcgct gctaaaaaag    45480
ccggagtaga agatggtaga aatcaataat caacgtaagg cgttcctcga tatgctggcg    45540
tggtcggagg gaactgataa cggacgtcag aaaaccagaa atcatggtta tgacgtcatt    45600
gtaggcggag agctatttac tgattactcc gatcaccctc gcaaacttgt cacgctaaac    45660
ccaaaactca aatcaacagg cgccggacgc taccagcttc tttcccgttg gtgggatgcc    45720
taccgcaagc agcttggcct gaaagacttc tctccgaaaa gtcaggacgc tgtggcattg    45780
cagcagatta aggagcgtgg cgcttttacct atgattgatc gtggtgatat ccgtcaggca    45840
atcgaccgtt gcagcaatat ctgggcttca ctgccgggcg ctggttatgg tcagttcgag    45900
cataaggctg acagcctgat tgcaaaattc aaagaagcgg gcggaacggt cagagagatt    45960
gatgtatgag cagagtcacc gcgattatct ccgctctggt tatctgcatc atcgtctgcc    46020
tgtcatgggc tgttaatcat taccgtgata acgccattac ctacaaagcc cagcgcgaca    46080
aaaatgccag agaactgaag ctggcgaacg cggcaattac tgacatgcag atgcgtcagc    46140
gtgatgttgc tgcgctcgat gcaaaataca cgaaggagtt agctgatgct aaagctgaaa    46200
atgatgctct gcgtgatgat gttgccgctg tcgtcgtcg gttgcacatc aaagcagtct    46260
gtcagtcagt gcgtgaagcc accaccgcct ccggcgtgga taatgcagcc tcccccgac    46320 tggcagacac cgctgaacgg gattatttca ccctcagaga gaggctgatc actatgcaaa    46380
aacaactgga aggaacccag aagtatatta atgagcagtg cagatagagt tgcccatatc    46440
gatgggcaac tcatgcaatt attgtgagca atacacacgc gcttccagcg gagtataaat    46500
gcctaaagta ataaaaccga gcaatccatt tacgaatgtt tgctgggttt ctgttttaac    46560
aacattttct gcgccgccac aaattttggc tgcatcgaca gttttcttct gcccaattcc    46620
agaaacgaag aaatgatggg tgatggtttc ctttggtgct actgctgccg gtttgttttg    46680
aacagtaaac gtctgttgag cacatcctgt aataagcagg gccagcgcag tagcgagtag    46740 cattttttc atggtgttat tcccgatgct ttttgaagtt cgcagaatcg tatgtgtaga    46800
aaattaaaca aaccctaaac aatgagttga aatttcatat tgttaatatt tattaatgta    46860
tgtcaggtgc gatgaatcgt cattgtattc ccggattaac tatgtccaca gccctgacgg    46920
ggaacttctc tgcgggagtg tccgggaata attaaaacga tgcacacagg gtttagcgcg    46980
tacacgtatt gcattatgcc aacgccccgg tgctgacacg gaagaaaccg gacgttatga    47040
```

```
tttagcgtgg aaagatttgt gtagtgttct gaatgctctc agtaaatagt aatgaattat    47100
caaaggtata gtaatatctt ttatgttcat ggatatttgt aacccatcgg aaaactcctg    47160
ctttagcaag attttccctg tattgctgaa atgtgatttc tcttgatttc aacctatcat    47220
aggacgtttc tataagatgc gtgtttcttg agaatttaac atttacaacc tttttaagtc    47280
cttttattaa cacggtgtta tcgttttcta acacgatgtg aatattatct gtggctagat    47340
agtaaatata atgtgagacg ttgtgacgtt ttagttcaga ataaaacaat tcacagtcta    47400
aatcttttcg cacttgatcg aatatttctt taaaaatggc aacctgagcc attggtaaaa    47460
ccttccatgt gatacgaggg cgcgtagttt gcattatcgt ttttatcgtt tcaatctggt    47520
ctgacctcct tgtgttttgt tgatgattta tgtcaaatat taggaatgtt ttcacttaat    47580
agtattggtt gcgtaacaaa gtgcggtcct gctggcattc tggagggaaa tacaaccgac    47640
agatgtatgt aaggccaacg tgctcaaatc ttcatacaga aagatttgaa gtaatatttt    47700
aaccgctaga tgaagagcaa gcgcatggag cgacaaaatg aataaagaac aatctgctga    47760
tgatccctcc gtggatctga ttcgtgtaaa aaatatgctt aatagcacca tttctatgag    47820
ttaccctgat gttgtaattg catgtataga acataaggtg tctctggaag cattcagagc    47880
aattgaggca gcgttggtga agcacgataa taatatgaag gattattccc tggtggttga    47940
ctgatcacca taactgctaa tcattcaaac tatttagtct gtgacagagc caacacgcag    48000
tctgtcactg tcaggaaagt ggtaaaactg caactcaatt actgcaatgc cctcgtaatt    48060
aagtgaattt acaatatcgt cctgttcgga gggaagaacg cgggatgttc attcttcatc    48120
acttttaatt gatgtatatg ctctcttttc tgacgttagt ctccgacggc aggcttcaat    48180
gacccaggct gagaaattcc cggacccttt ttgctcaaga gcgatgttaa tttgttcaat    48240
catttggtta ggaaagcgga tgttgcgggt tgttgttctg cgggttctgt tcttcgttga    48300
catgaggttg ccccgtattc agtgtcgctg atttgtattg tctgaagttg tttttacgtt    48360
aagttgatgc agatcaatta atacgatacc tgcgtcataa ttgattattt gacgtggttt    48420
gatggcctcc acgcacgttg tgatatgtag atgataatca ttatcacttt acgggtcctt    48480
tccggtgatc cgacaggtta cg                                            48502
```

GENETICALLY MODIFIED PHAGE AND USE THEREOF

FIELD OF INVENTION

The present invention relates to the field of production of biomolecules of interest in biologic systems. Specifically, the present invention relates to a genetically modified phage, and use thereof in order to avoid phage contamination of the culture broth and/or bacterial lysis.

BACKGROUND OF INVENTION

Bacterial cells are systems of choice for the production of biomolecules, especially of target proteins. Among other advantages, bacterial systems are easy to use and allow the rapid production of large quantities of proteins in a limited volume of culture.

One of the most widely and routinely used bacterial system is the bacteriophage T7 expression system. This bacterial system was described in U.S. Pat. No. 4,952,496. In this system, the gene encoding the target protein is placed under the control of a T7 promoter, and is transformed in a bacterial host, usually *E. coli*, which comprises an integrated lambda DE3 lysogen phage. The lambda DE3 lysogen phage carries the gene encoding the T7 RNA polymerase under the control of a lacUV5 promoter. When cultured on an IPTG-containing medium, the expression of the T7 RNA polymerase is induced, and allows the expression of the target protein.

Due to the integration of the gene of the T7 RNA polymerase (T7 gene 1) within the sequence of the Int gene, Lambda DE3 phage should be defective in its ability to enter into the lytic phase. However, bacterial lysis is observed during some protein productions and in the absence of any other phage, suggesting that the DE3 phage may recover its lytic properties. The bacterial lysis and even more, the presence of infectious phages in the culture broth is highly problematic because (i) it compromises the use of produced target proteins for some applications, such as, for example, pharmaceutical applications, (ii) the decontamination process in order to remove any trace of phages requires the shutdown of the production lines and the complete renewal of the batches of culture and (iii) it reduces dramatically the yield of recombinant protein.

Alternative methods to the use of a phage have been described:

WO 03/050240 describes an expression system for producing a target protein in a host cell comprising a gene encoding T7 RNA polymerase integrated using homologous recombination. However, the system of WO 03/050240 is difficult to implement, due to the size of the T7 RNA polymerase gene and due to the fact that homologous recombination is not possible or easy to do in all *E. coli* strains (as mentioned by Phue et al., Biotechnology and Bioengineering, 101, 831-836, 2008). Consequently, the number of transformed cells carrying the T7 RNA polymerase integration remains very low or these cells are not obtained. Moreover, using homologous recombination, it is necessary to use a selective marker to select bacteria containing integration of the T7 RNA polymerase gene. This marker will not be usable for another selection step and could be undesired for the final use of the strain. For example, selective markers often used are antibiotic resistance genes but it is recommended to avoid these genes in biopharmaceutical productions. An additional step is thus required to remove the antibiotic resistance gene from the strain and it is not always possible to do it.

WO 2008/139153 describes another expression system, wherein the host cell is transformed with a plasmid comprising an expression cassette for T7 RNA polymerase. However, due to the use of a plasmid, hosts cells have to be maintained in selective conditions to make sure that they still comprise the plasmid. In addition, plasmids are frequently subjected to recombination, which impaired the expression system.

Therefore, there is a need for a novel method for producing a biomolecule of interest, wherein, when a phage is used, the culture is not contaminated by infectious phages or unintentionally lysed during growth or protein production.

The present invention hereby provides a genetically modified phage that does not recover its lytic properties during culture, thereby allowing the production of a biomolecule of interest without phage contamination.

SUMMARY OF THE INVENTION

One object of the invention is a genetically modified phage wherein:
an expression system is inserted, and
the S and/or the R genes are inactivated.

In one embodiment of the invention, the Int and/or Xis gene is inactivated.

In another embodiment of the invention, the Rz gene is inactivated.

In another embodiment of the invention, an expression system is inserted and the Int gene, the Xis gene and the R, S and Rz genes are inactivated.

In another embodiment of the invention, the expression system is the T7 expression system.

In another embodiment of the invention, the phage is the lambda phage, the 434 phage, the phi80 phage, the phi81 phage, the HK97 phage, the P21 phage.

In another embodiment of the invention, the genetically modified phage as described here above has the sequence SEQ ID NO: 10.

Another object of the invention is a kit comprising the genetically modified phage as described here above and a helper phage.

Another object if the invention is a host cell comprising the genetically modified phage as described here above.

In one embodiment of the invention, the host cell is an enterobacteria, preferably *E. coli*.

In another embodiment of the invention, the host cell as described here above further comprises the inactivation of at least one of the genes tonA, galK, araB, araA, lon, ompT, rcsA, hsdR, mrr, endA and recA.

In another embodiment of the invention, the host cell as described here above comprises the insertion of the ccdb gene.

Another object of the invention is a kit comprising the host cell as described here above and a plasmid comprising the ccdA gene.

Another object of the invention is a process for preparing a host cell as described here above, comprising infecting a host cell with a genetically modified phage as described here above.

Another object of the invention is a process for producing a biomolecule of interest, comprising:
cultivating a host cell comprising the genetically modified phage according to any one of claims 1 to 7 and the nucleic acid sequence of the biomolecule of interest, and
recovering the biomolecule of interest.

DETAILED DESCRIPTION

The present invention relates to a genetically modified phage, wherein the ability of the phage to regain its lytic properties is limited.

The Inventors focused on the genetic modification of a phage. Surprisingly, the Inventors showed that it was not possible to delete all viral sequences of the integrated phage, because the viability of the infected bacteria was severely compromised in that case. In particular, the Inventors showed that the deletion of a DNA fragment comprising the coding sequences of the ral gene and the N gene leads to the death of the host cell (See EXAMPLES). This result was surprising because the ral and N genes are not known to be involved in the lysogenic state; the N gene is only described as essential for lytic growth. On the contrary, in lysogenic state, a repressor of the phage, named C1 or C2, blocks the expression of N and ral.

The present invention thus relates to a genetically modified phage wherein
an expression system is inserted, and
at least one of the Int, Xis, R, S and Rz genes are inactivated.

In one embodiment, the genetically modified phage comprises an expression system and the S gene is inactivated.

In one embodiment, the genetically modified phage comprises an expression system and the R gene is inactivated.

In one embodiment, the genetically modified phage comprises an expression system and the Int gene is inactivated.

In one embodiment, the genetically modified phage comprises an expression system and the Xis gene is inactivated.

In one embodiment, the genetically modified phage comprises an expression system and the S and Int genes are inactivated.

In one embodiment, the genetically modified phage comprises an expression system and the S and Xis genes are inactivated.

In one embodiment, the genetically modified phage comprises an expression system and the S and R genes are inactivated.

In one embodiment, the genetically modified phage comprises an expression system and the S and Rz genes are inactivated.

In one embodiment, the genetically modified phage comprises an expression system and the R and Rz genes are inactivated.

In one embodiment, the genetically modified phage comprises an expression system and the R and Int genes are inactivated.

In one embodiment, the genetically modified phage comprises an expression system and the R and Xis genes are inactivated.

In one embodiment, the genetically modified phage comprises an expression system and the S, Int and Xis genes are inactivated.

In one embodiment, the genetically modified phage comprises an expression system and the S, Int and Rz genes are inactivated.

In one embodiment, the genetically modified phage comprises an expression system and the S, Int and R genes are inactivated.

In one embodiment, the genetically modified phage comprises an expression system and the S, Xis and Rz genes are inactivated.

In one embodiment, the genetically modified phage comprises an expression system and the S, Xis and R genes are inactivated.

In one embodiment, the genetically modified phage comprises an expression system and the S, R and Rz genes are inactivated.

In one embodiment, the genetically modified phage comprises an expression system and the R, Int and Xis genes are inactivated.

In one embodiment, the genetically modified phage comprises an expression system and the R, Int and Rz genes are inactivated.

In one embodiment, the genetically modified phage comprises an expression system and the R, Xis and Rz genes are inactivated.

In one embodiment, the genetically modified phage comprises an expression system and the S, Int, Xis and Rz genes are inactivated.

In one embodiment, the genetically modified phage comprises an expression system and the S, Int, Xis and R genes are inactivated.

In one embodiment, the genetically modified phage comprises an expression system and the S, Int, R and Rz genes are inactivated.

In one embodiment, the genetically modified phage comprises an expression system and the S, R, Xis and Rz genes are inactivated.

In one embodiment, the genetically modified phage comprises an expression system and the R, Rz, Xis and Int genes are inactivated.

In one embodiment, the genetically modified phage comprises an expression system and the S, R, Rz, Xis and Int genes are inactivated.

Examples of phages which can be used in the invention include, but are not limited to, the lambda (λ) phage, lambda-like and lambdoid phages. Lambda phage, also known as coliphage lambda, is a virus that infects *Escherichia coli*. Lambda is a temperate bacteriophage. Lambda-like phages form a family of bacteriophages and archaeal viruses which are characterized by long, non-contractile tails. Lambdoid phages are natural relatives of lambda phage. Most of them grow on *E. coli*, but a few come from other host cells, such as, for example, *Salmonella typhimurium*. These phages may have the same gene order as lambda.

Examples of lambda-like and lambdoid phages which could be used in the present invention include, but are not limited to, coliphage 434, phi80, phi81, HK97, P21 and P22.

In an embodiment, the phage is lambda (Enterobacteria phage lambda, accession number NC_001416) having a sequence of SEQ ID NO:35.

TABLE 1

| Start | End | Name | Description |
|---|---|---|---|
| 191 | 736 | nu1 | DNA packaging protein |
| 711 | 2636 | A | DNA packaging protein |
| 2633 | 2839 | W | head-tail joining protein |
| 2836 | 4437 | B | capsid component |
| 4418 | 5737 | C | capsid component |
| 5132 | 5737 | nu3 | capsid assembly protein |
| 5747 | 6079 | D | head-DNA stabilization protein |
| 6135 | 7160 | E | capsid component |
| 7202 | 7600 | Fi | DNA packaging protein |
| 7612 | 7965 | Fii | head-tail joining protein |
| 7977 | 8555 | Z | tail component |
| 8552 | 8947 | U | tail component |
| 8955 | 9695 | V | tail component |

TABLE 1-continued

| Start | End | Name | Description |
|---|---|---|---|
| 9711 | 10133 | G | tail component |
| 10115 | 10549 | T | tail component |
| 10542 | 13103 | H | tail component |
| 13100 | 13429 | M | tail component |
| 13429 | 14127 | L | tail component |
| 14276 | 14875 | K | tail component |
| 14773 | 15444 | I | tail component |
| 15505 | 18903 | J | tail:host specificity protein |
| 18965 | 19585 | lom | outer host membrane |
| 19650 | 20855 | orf-401 | Tail fiber protein |
| 20767 | 20147 | orf206b | hypothetical protein |
| 21029 | 21973 | orf-314 | Tail fiber |
| 21973 | 22557 | orf-194 | Putative fiber assembly protein |
| 23918 | 22686 | ea47 | ea47 |
| 25399 | 24509 | ea31 | ea31 |
| 26973 | 25396 | ea59 | ea59 |
| 28882 | 27812 | int | integration protein |
| 29078 | 28860 | xis | Excisionase |
| 29285 | 29118 | hypothetical | hypothetical protein |
| 29655 | 29374 | ea8.5 | ea8.5 |
| 30395 | 39847 | ea22 | ea22 |
| 31024 | 30839 | orf61 | hypothetical protein |
| 31196 | 31005 | orf63 | hypothetical protein |
| 31351 | 31169 | orf60a | hypothetical protein |
| 32028 | 31348 | exo | exonuclease |
| 32810 | 32025 | bet | bet |
| 33232 | 32816 | gam | host-nuclease inhibitor protein Gam |
| 33330 | 33187 | kil | host-killing protein |
| 33463 | 33299 | cIII | antitermination protein |
| 35582 | 33494 | ea10 | Putative single-stranded DNA binding protein |
| 35582 | 33930 | ral | restriction alleviation protein |
| 34357 | 34271 | orf28 | hypothetical protein |
| 34482 | 35036 | lambdap48 | Superinfection exclusion protein B |
| 35582 | 34560 | N | early gene regulator |
| 36259 | 35825 | rexb | exclusion protein |
| 37114 | 36275 | rexa | exclusion protein |
| 37940 | 37227 | cI | repressor |
| 38023 | 38135 | cro | antirepressor |
| 38360 | 38653 | cII | transcriptional activator |
| 38686 | 39585 | O | DNA replication protein |
| 39582 | 40283 | P | DNA replication protein |
| 40280 | 40570 | ren | ren exclusion protein |
| 40644 | 41084 | NinB | NinB |
| 41081 | 41953 | NinC | NinC protein |
| 41950 | 42123 | NinD | NinD protein |
| 42090 | 42272 | NinE | NinE protein |
| 42269 | 42439 | NinF | NinF protein |
| 42429 | 43043 | NinG | NinG protein |
| 43040 | 43246 | NinH | NinH protein |
| 43224 | 43889 | NinI | NinI protein |
| 43886 | 44509 | Q | late gene regulator |
| 44621 | 44815 | orf-64 | hypothetical protein |
| 45186 | 45509 | S | Cell lysis protein |
| 45493 | 45969 | R | endolysin |
| 45966 | 46427 | Rz | cell lysis protein |
| 46186 | 46368 | Rz1 | Rz1 protein |
| 46752 | 46459 | bor | Bor protein precursor |
| 47575 | 47042 | lambdap78 | putative enveloppe protein |
| 47738 | 47944 | lambdap79 | hypothetical protein |

In the present invention, the position of the residues within the sequence of the lambda phage relates to NC_001416.

In another embodiment, the phage is lambda DE3 (accession number EU078592). The Lambda DE3 phage is a modified lambda phage D69, comprising the gene encoding the T7 RNA polymerase under the control of a lacUV5 promoter. The list of the genes carried by the sequence of Lambda DE3 and their position are shown in the Table 2 below.

TABLE 2

| Start | End | Name | Description |
|---|---|---|---|
| 341 | 1423 | lacI | lactose operon repressor |
| 1546 | 1995 | lacZ | N-terminal fragment of beta-galactosidase |
| 2026 | 4677 | 1 | T7 DNA-directed RNA polymerase |
| 5804 | 5586 | xis | excisionase |
| 6011 | 5844 | hypothetical | Hypothetical protein |
| 6381 | 6100 | ea8.5 | ea8.5 |
| 7121 | 6573 | ea22 | ea22 |
| 7750 | 7565 | hypothetical | Hypothetical protein |
| 7922 | 7731 | hypothetical | Hypothetical protein |
| 8077 | 7895 | hypothetical | Hypothetical protein |
| 8754 | 8074 | exo | exonuclease |
| 9536 | 8751 | bet | Bet |
| 9958 | 9542 | gam | host-nuclease inhibitor protein Gam |
| 10056 | 9913 | kil | host-killing protein |
| 10189 | 10025 | cIII | antitermination protein |
| 10630 | 10262 | ea10 | putative single-stranded DNA binding protein |
| 11013 | 10813 | ral | restriction alleviation protein |
| 11083 | 10997 | hypothetical | Hypothetical protein |
| 11391 | 11092 | N | probable regulatory protein N (early gene regulator) |
| 12356 | 11706 | C2 | repressor protein C2 |
| 12437 | 12622 | cro | regulatory protein cro (Antirepressor) |
| 12738 | 13037 | cII | antitermination protein |
| 13070 | 13969 | O | DNA replication protein |
| 13966 | 14667 | P | DNA replication protein |
| 14664 | 15467 | ren | Ren exclusion protein |
| 15464 | 16087 | Q | late gene regulator |
| 16199 | 16393 | hypothetical | Hypothetical protein |
| 16764 | 17087 | S | cell lysis protein |
| 17071 | 17547 | R | cell lysis protein |
| 17544 | 18005 | Rz | cell lysis protein |
| 18330 | 18037 | Bor | Bor protein precursor |
| 19153 | 18620 | putative | putative envelope protein |
| 19316 | 19522 | hypothetical | Hypothetical protein |
| 20270 | 20815 | nu1 | DNA packaging protein |
| 20790 | 22715 | A | DNA packaging protein |
| 22712 | 22918 | W | head-tail joining protein |
| 22915 | 24516 | B | capsid component |
| 24497 | 25816 | C | capsid component |
| 25826 | 26158 | D | head-DNA stabilization protein |
| 26214 | 27239 | E | capsid component |
| 27281 | 27679 | Fi | DNA packaging protein |
| 27691 | 28044 | Fii | head-tail joining protein |
| 28056 | 28634 | Z | tail component |
| 28631 | 29026 | U | tail component |
| 29034 | 29774 | V | tail component |
| 29790 | 30212 | G | tail component |
| 30194 | 30628 | T | tail component |
| 30621 | 33182 | H | tail component |
| 33179 | 33508 | M | tail component |
| 33508 | 34206 | L | tail component |
| 34356 | 34955 | K | tail component |
| 34853 | 35524 | I | tail component |
| 35585 | 38983 | J | tail:host specificity protein |
| 39045 | 39665 | lom | outer host membrane |
| 39730 | 40935 | tail | tail fiber protein |
| 41109 | 41372 | tail | tail fiber |
| 42175 | 41237 | ea59 | ea59 |

In the present invention, the position of the residues within the sequence of the lambda DE3 phage relates to EU078592.

As used herein, an "expression system" refers to a linear or circular DNA molecule composed of a fragment encoding a nucleic acid sequence operably linked to an additional fragment for the transcription of the system.

The additional fragment includes a promoter and a stop codon sequence. The expression system may further contain one or more origins of replication, one or more selection markers and a sequence encoding a ribosome binding site.

"Operably linked" means that fragments are arranged to be functioning as they are supposed to be, for example once transcription starts at the promoter, it goes through coded fragment to stop codon.

"Promoter" in the meaning of the present invention is an expression control element that permits binding of RNA polymerase and the initiation of transcription.

In one embodiment of the invention, the nucleic acid sequence is under the control of a "strong" promoter. A strong promoter is characterized by a high binding affinity of the promoter sequence to an RNA polymerase, usually the naturally occurring corresponding RNA polymerase, on the one hand and the rate of formation of mRNA by that RNA polymerase on the other hand.

In a preferred embodiment, the nucleic acid sequence is under the control of an "inducible promoter". An "inducible promoter" is a promoter that may be regulated by external factors, e.g. the presence of an inductor (also termed "inducer") molecule or the absence of a repressor molecule, or physical factors like increased or decreased temperature, osmolarity, or pH value. Different promoters and the respective induction principles were reviewed by Makrides et al. (Microbiological Reviews, 1996, (60)$_3$: 512-538). Examples of inducible promoters which may be used in the present invention include, but are not limited to the tac or the trc promoter, the lac or the lacUV5 promoter (all inducible by lactose or its analog IPTG (isopropylthiol-β-D-galactoside)), the tightly regulatable araBAD promoter (PBAD; Guzman et al., 1995, inducible by arabinose), the trp promoter (inducible by β-indole acrylic acid addition or tryptophan starvation, repressible by tryptophan addition), the lambda promoter pL (λ) (induction by an increase of temperature), the phoA promoter (inducible by phosphate starvation), the PprpB (induction with propionate) or other promoters suitable for recombinant protein expression, which all use E. coli RNA polymerase.

Among inducible promoters are those that show a "leaky" expression behavior. Such promoters (so-called "leaky promoters") are, in principle, inducible, but show nevertheless also basal expression without being externally induced. Inducible promoters that show leaky expression under non-induced conditions may behave similarly to constitutive promoters (i.e. they are steadily and continuously active or they may be activated or enhanced as a result of certain cultivation conditions). Leaky promoters may be particularly useful for continuously operated cultivation processes. Examples of leaky promoters are the T7 promoter and the trp promoter.

In one embodiment of the invention, the promoter may also be constitutive, i.e. a promoter which controls expression without the need for induction on the one hand, or the possibility of repression on the other hand. Hence, there is continuous and steady expression at a certain level. As an example, the strong constitutive HCD promoter (Poo et al., Biotechnology Letters, 2002, 24:1185-1189; Jeong et al., Protein expression and purification, 2004, 36:150-156) may be applied for constitutive expression.

In one embodiment, the expression system comprises a nucleic acid sequence encoding a protein that induces the expression of the biomolecule of interest. Advantageously, the expression of the biomolecule of interest is induced in particular conditions, such as, for example, under selection.

Examples of such nucleic acid sequences include, but are not limited to, the gene encoding the T7 RNA polymerase, T7 gene 1. In that case, the expression of the T7 RNA polymerase induces the expression of the biomolecule of interest placed under the control of a T7 promoter.

Preferably, the expression system is the T7 expression system. The T7 expression system was described in U.S. Pat. No. 4,952,496, which is incorporated herein by reference. The T7 expression system comprises a DNA fragment from the T7 phage, containing the entire coding sequence for the T7 RNA polymerase (i.e. the T7 gene 1). Any natural active promoter of the T7 gene 1 was removed and an inducible lacUV5 promoter was inserted ahead of the coding sequence. The lacUV5 promoter is induced by addition of IPTG to the culture medium.

According to another embodiment, the expression system comprises the nucleic acid sequence of the biomolecule of interest.

With regard to the biomolecule of interest, there are no limitations. It may, in principal, be any amino acid sequences, nucleic acid sequences, such as, for example, DNA or RNA.

Examples of amino acid sequences include polypeptide, protein or peptide that is to be produced on a manufacturing scale, e.g. an industrial biomolecule or a therapeutic biomolecule.

Examples for biomolecules that can be produced by the method of the invention are, without limitation, enzymes, regulatory proteins, receptors, peptides, e.g. peptide hormones, cytokines, membrane or transport proteins.

The biomolecules of interest may also be antigens as used for vaccination, vaccines, antigen-binding proteins, immune stimulatory proteins, allergens, full-length antibodies or antibody fragments or derivatives. Antibody derivatives may be selected from the group of single chain antibodies, (scFv), Fab fragments, Fv fragments, single domain antibodies (VH or VL fragment), domain antibodies like camelid single domain antibodies (VHH, nanobodies) or other antibody formats as described for instance in Andersen and Reilly (Current Opinion in Biotechnology, 2004, 15:456-462) or Holliger and Hudson (Nature Biotechnology, 2005 (23)$_9$: 1126-1136).

The biomolecules of interest in the present invention can also be exemplified by protein (viral antigen), e.g., coat protein, core protein, protease, reverse transcriptase, integrase, and so forth, encoded in the genome of a pathogenic virus, e.g., hepatitis B virus, hepatitis C virus, I-HV, influenza, and so forth; growth factors such as platelet-derived growth factor (PDGF), stem cell growth factor (SCF), hepatocyte growth factor (HGF), transforming growth factor (TGF), nerve growth factor (NGF), epidermal growth factor (EGF), fibroblast growth factor (FGF), insulin-like growth factor (IGF), and so forth; cytokines such as tumor necrosis factor, interferon, interleukin, and so forth; hematopoietic factors such as erythropoietin, granulocyte colony-stimulating factor, granulocyte-macrophage colony-stimulating factor, macrophage colony-stimulating factor, thrombopoietin, and so forth; peptide hormones such as luteinizing hormone-releasing hormone (LB-RH), thyrotropin-releasing hormone (TRH), insulin, somatostatin, growth hormone, prolactin, adrenocorticotropic hormone (ACTH), melanocyte-stimulating hormone (MSH), thyroidstimulating hormone (TSH), luteinizing hormone (LU), follicle-stimulating hormone (FSH), vasopressin, oxytoxin, calcitonin, parathyroid hormone (PTH), glucagon, gastrin, secretin, pancreozymin, cholecystokinin, angiotensin, human placenta lacto8en, human chorionic gonadotropin (HCG), cerulein, motilin, and so forth; analgesic peptides such as enkephalin, endorphin, dynorphin, kyotorphin, and so forth; enzymes such as superoxide dismutase (SOD), urokinase, tissue plasminogen activator (TPA), asparaginase, kallikrein, and so forth; peptide neurotransmitters such as bombesin, neutrotensin, bradykinin, substance P, Alzheimer's amyloid peptide (AD), SOD1, presenillin 1 and 2, renin, Dsynuclein, amyloid A, amyloid P, activin, anti-HER-2, bombesin, enkephalinase, protease inhibitors, therapeutic enzymes, D 1-antitrypsin, mammalian trypsin inhibitor, mammalian pancreatic trypsin inhibitor, calcitonin, cardiac hypertrophy factor, cardiotrophins (such as cardiotrophin-1), CD proteins (such as CD-3, CD-4, CD-8 and CD-19), CFTR, CTNF, DNase, human chorionic gonadotropin, mouse gonadotropin-associated peptide, cytokines, transthyretin, amylin, lipoproteins, lymphokines, lysozyme, a growth hormone (including human growth hormone), bovine growth hormone, growth hormone releasing factor, parathyroid hormone, thyroid stimulating hormone, growth factors, brain-derived neurotrophic growth factor, epidermal growth factor (EGF), fibroblast growth factor (such as D FGF and D FGF), insulin-like growth factor-I and -II, des(1-3)-IGF-I (brain IGF-I), insulin-like growth factor binding proteins, nerve growth factor (such as NGF-D), platelet derived growth factor (PDGF), vascular endothelial growth factor (VEGF), receptors for growth hormones or growth factors, transforming growth factor (TGF) (such as TGF-D, TGF-D 1, TGF-D2, TGF-D3, TGF-D4 or TGF-D5), neurotrophic factors (such as neurotrophin-3, -4, -5, or -6), gelsolin, glucagon, kallikreins, mullerian-inhibiting substance, neurotrophic factors, p53, protein A or D, prorelaxin, relaxin A-chain, relaxin B-chain, rheumatoid factors, rhodopsin, a serum albumin (such as human serum albumin), inhibin, insulin, insulin chains, insulin A-chain, insulin D-chain, insulin receptor, proinsulin, luteinizing hormone, integrin, interleukins (ILs) (such as IL-1 to IL-10, IL-12, IL-13), erythropoietin, thrombopoietin, fibrillin, follicle stimulating hormone, clotting factors (such as factor VIIIC, factor IX, tissue factor, and von Willebrands factor), anticlotting factors (such as Protein C, atrial naturietic factor, lung surfactant), a plasminogen activator (such as human tissue plasminogen activator or urokinase), thrombin, tumor necrosis factor-D or D, D-ketoacid dehydrogenase, addressins, bone morphogenetic proteins (BMPs), collagen, colony stimulating factors (CSFs) (such as M-CSF, GM-CSF and G-CSF), decay accelerating factor, homing receptors, interferons (such as interferon-alpha, -gamma and -beta), keratin, osteoinductive factors, PRNP, regulatory proteins, superoxide dismutase, surface membrane proteins, transport proteins, T-cell receptors, antigens such as gpl 20(HIb) immuno toxins, atrial natriuretic peptide, seminal vesicle exocrine protein, D 2-microglobulin, PrP, precalcitonin, ataxin 1, ataxin 2, ataxin 3, ataxin 6, ataxin 7, huntingtin, androgen receptor, CREB-binding protein, gp120, p300, CREB, API, ras, NFAT, jun, fos, dentaorubral pallidoluysian atrophy-associated protein, a microbial protein (e.g., maltose binding protein, ABC transporter, glutathione S transferase, thioredoxin, D-lactamase), green fluorescent protein, red fluorescent protein, an enzyme such as superoxide dismutase, asparaginase, arginase, arginine deaminase, adenosine deaminase, ribonuclease, catalase, uricase, bilirubin oxidase, trypsin, papain, alkaline phosphatase, beta-glucoronidase, purine nucleoside phosphorylase or batroxobin, an opioid, e.g. endorphins, enkephalins or non-natural opioids, a hormone or neuropeptide, e.g. calcitonin, glucagon, gastrins, adreno-corticotropic hormone (ACTH), cholecystokinins, lutenizing hormone, gonadotropin-releasing hormone, chorionic gonadotropin, corticotrophin-releasing factor, vasopressin, oxytocin, antidiuretic hormones, thyroid-stimulating hormone, thyrotropin-releasing hormone, relaxin, prolactin, peptide YY, neuropeptide Y, pancreatic polypeptide, leptin, CART (cocaine and amphetamine regulated transcript), a CART related peptide, perilipin, melano-cortins (melanocyte-stimulating hormones) such as MC-4, melanin-concentrating hormones, natriuretic peptides, adrenomedullin, endothelin, secretin, amylin, vasoactive intestinal peptide (VIP), pituitary adenylate cyclase activating polypeptide (PACAP), bombesin, bombesin-like peptides, thymosin, heparin-binding protein, soluble CD4, hypothalamic releasing facto-rand melatonin or functional analogs thereof. In another embodiment of the invention the target protein may be a processing enzyme such as proteases (e.g. enterokinase, caspases, trypsine like serine proteases), lipase, phosphatase, glycosyl hydrolases (e.g. mannosidases, xylosidases, fucosidases), kinase, mono or dioxidase, peroxidase, transglutaminase, carboxypeptidase, amidase, esterase, and phosphatase . . . .

Preferred sources for such mammalian polypeptides include human, bovine, equine, porcine, lupine and rodent sources, with human proteins being particularly preferred.

The biomolecule of interest of the present invention also encompasses variants of the aforementioned protein. These variants encompass, for example, protein that has the same activity as the aforementioned protein and that comprises an amino acid sequence with, in the amino acid sequence of the aforementioned protein, one or more deleted, substituted, inserted and/or added amino acids. Such protein can be exemplified by protein that has the same activity as the aforementioned protein and that comprises an amino acid sequence with, in the amino acid sequence of the aforementioned protein, one or more deleted, substituted, inserted and/or added amino acids. Two or more different types of modifications selected from deletion, substitution, insertion, and addition may be carried out concurrently.

The biomolecule of interest of the present invention also encompasses "partial peptides" of the aforementioned protein. A partial peptide of the protein can be exemplified by a partial peptide comprising an amino acid sequence in which a portion of the amino acid sequence of the aforementioned protein runs uninterrupted, wherein the partial peptide preferably has the same activity as said protein. Such a partial peptide can be exemplified by a polypeptide that has an amino acid sequence comprising at least 20 and preferably at least 50 of the amino acid residues in the amino acid sequence of the aforementioned protein. This polypeptide preferably contains the amino acid sequence that corresponds to the region that is involved with the activity of the aforementioned protein. In addition, the partial peptide used in the present invention may also be a partial peptide as yielded by a modification of this polypeptide wherein 1 or a plurality of amino acid residues (for example, approximately 1 to 20, more preferably approximately 1 to 10, and even more preferably approximately 1 to 5) is deleted from, substituted in, inserted into, and/or added to its amino acid sequence. The partial peptide used in the present invention can also be used as an antigen for antibody production.

In one embodiment of the invention, the biomolecule of interest is selected from the group comprising Human growth hormone, human insulin, follicle-stimulating hormone, Factor VIII, Erythropoeietin, Granulocyte colony-stimulating factor, Alpha-glactosidase A, Alpha-L-iduronidase, N-actetylgalactosamine-4-sulfatase, Dornase alfa, Tisssue plasminogen activator, Glucocerebrosidase, Interferon, Insulin-like growth factor 1, bovine somatotropin, Porcine somatotropin, bovine chymosin, and envelop protein of the hepaptitis B virus.

The biomolecule of interest also encompasses modified polypeptides or proteins that have underwent posttranslational and post-export modifications in the periplasm such as cyclization, glycosylation, phosphorylation, methylation, oxidation, dehydration, proteolytic cleavage.

In one embodiment, the biomolecule of interest is an enzyme for metabolizing a biomolecule in the extracellular medium (herein referred as "extracellular biomolecule"). In one embodiment, the extracellular biomolecule comprises a polysaccharide or a lipid. In one embodiment of the invention, the polysaccharide comprises alginate, pectin, cellulose, cellobiose, laminarin, or a mixture thereof. In one embodiment of the invention, the lipid comprises a fatty acid, a glycolipid, a betaine lipid, a glycerolipid, a phospholipid, a glycerolphospholipid, a sphingolipid, a sterol lipid, a prenol lipid, a saccharolipid, a polyketide, or a mixture thereof. In one embodiment of the invention, the biomolecule of interest is an enzyme converting the polysaccharide to a monosaccharide, an oligosaccharide, or both.

In one embodiment of the invention, the biomolecule of interest is an enzyme converting the lipid to a fatty acid, a monosaccharide, or both. In one embodiment of the invention, the monosaccharide or oligosaccharide is oligoalginate, mannuronate, guluronate, mannitol, a-keto acid, 4-deoxy-L-erythro-hexoselulose uronate (DEHU), 2-keto-3-deoxy D-gluconate (KDG), glucose, glucuronate, galacturonate, galactose, xylose, arabinose, or mannose. In one embodiment of the invention, the fatty acid is 14:0, trans-14, 16:0, 16:1n-7, trans-16, 16:2n-6, 18:0, 18:1n-9, 18:2n-6, 18:3n-6, 18:3n-3, 18:4n-3, 20:0, 20:2n-6, 20:3n-6, 20:4n-3, 20:4n-6, or 20:5n-3.

In one embodiment of the invention, the biomolecule of interest is an enzyme converting the extracellular biomolecule to a commodity chemical. In one embodiment of the invention, the commodity chemical is ethanol, butanol, or biodiesel. In one embodiment of the invention, the biodiesel is a fatty acid, a fatty acid ester, or a terpenoid.

As used herein, the term "inactivated" refers to the interruption or to the suppression of the expression of a gene at transcriptional or translational levels. Preferably, the term "inactivated" refers to a gene whose transcription is suppressed.

According to the invention, the inactivation of a gene may be due to the mutation of the gene or to the insertion of the expression system within the coding sequence of the gene.

In the meaning of the present invention, the term "mutation" refers to a stable change in the genetic sequence. Examples of mutation which could lead to the inactivation of a gene in the present invention include, but are not limited to, point mutations, insertions, deletions and amplification or gene duplication.

Preferably, the mutation is a deletion. The term "deletion" as used herein means the loss or absence of a gene, preferably the total loss or absence of a gene. More preferably, the deletion starts at or before the start codon of the deleted gene, and ends at or after the stop codon of the deleted gene.

In one embodiment of the invention, the S gene is inactivated. The S gene encodes both a holin (S105) and an anti-holin (S107) protein. The holin protein triggers the formation of holes in the membrane. The holing holin is required for release of the endolysin encoded by the R gene. At the opposite, the antiholin protein inhibits the 5105 hole formation. According to an embodiment, the S gene has the sequence SEQ ID NO: 1. In another embodiment, the sequence of the S gene presents a sequence identity of at least 70%, at least 75%, at least 80%, at least 85%, at least 90%, at least 91%, at least 92%, at least 93%, at least 94%, at least 95%, 5 at least 96%, at least 97%, at least 98%, and even more preferably of at least 99% with SEQ ID NO: 1.

The S gene may contain conservative sequence modifications that refer to amino acid modifications that do not significantly affect or alter the function of the S protein. Such conservative modifications include amino acid substitutions, additions and deletions. Modifications can be introduced into the S gene sequence by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. The modified sequence of the S protein may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the sequence of the S protein can be replaced with other amino acid residues from the same side chain family and the modified S protein can be tested for retained function (i.e., the properties set forth herein) by comparison with the S protein encoded by the sequence SEQ ID NO: 1.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics 5 and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/ NIH Bethesda, Md. 20894; Altschul et al., supra). The well-known Smith Waterman algorithm may also be used to determine identity.

In another embodiment, the R gene is inactivated. The R protein is an endolysin: this transglycosylase degrades the murein of the cell wall of the host cell. According to an embodiment, the R gene has the sequence SEQ ID NO: 2. In another embodiment, the sequence of the R gene presents a sequence identity of at least 70%, at least 75%, at least 80%, at least 85%, at least 90%, at least 91%, at least 92%, at least 93%, at least 94%, at least 95%, 5 at least 96%, at least 97%, at least 98%, and even more preferably of at least 99% with SEQ ID NO: 2.

The R gene may contain conservative sequence modifications as described here above that refer to amino acid modifications that do not significantly affect or alter the function of the R protein. The modified sequence of the R protein may comprise one, two, three, four or more amino acid insertions, deletions or substitutions. Thus, one or more amino acid residues within the sequence of the R protein can be replaced with other amino acid residues from the same side chain family and the modified R protein can be tested for retained function (i.e., the properties set forth herein) by comparison with the R protein encoded by the sequence SEQ ID NO: 2.

In another embodiment, the Rz gene is inactivated. The Rz protein belongs to the spanin family. This protein may be involved in disrupting the outer membrane of the host cell during the lytic phase. According to an embodiment, the Rz gene has the sequence SEQ ID NO: 3. In another embodiment, the sequence of the Rz gene presents a sequence identity of at least 70%, at least 75%, at least 80%, at least 85%, at least 90%, at least 91%, at least 92%, at least 93%, at least 94%, at least 95%, 5 at least 96%, at least 97%, at least 98%, and even more preferably of at least 99% with SEQ ID NO: 3.

The Rz gene may contain conservative sequence modifications as described here above that refer to amino acid modifications that do not significantly affect or alter the function of the Rz protein. The modified sequence of the Rz protein may comprise one, two, three, four or more amino acid insertions, deletions or substitutions. Thus, one or more amino acid residues within the sequence of the Rz protein can be replaced with other amino acid residues from the same side chain family and the modified Rz protein can be tested for retained function (i.e., the properties set forth herein) by comparison with the Rz protein encoded by the sequence SEQ ID NO: 3.

In another embodiment, a nucleic acid fragment comprising the coding sequence of the S gene is deleted. According to the invention, said nucleic acid fragment does not comprise the coding sequences of the ral gene (SEQ ID NO: 4) and/or of the N gene (SEQ ID NO: 5). Therefore, according to an embodiment, when the phage is lambda, the region between residues 33930 and 35582 is not deleted.

According to another embodiment, when the phage is lambda(DE3), the region between residues 10813 and 11391 is not deleted.

Preferably, said nucleic acid fragment does not comprise the coding sequence of N and C2 (SEQ ID NO: 6), as well as the regulatory sequences of the promoter of C2. To make sure that the regulatory sequences of C2 are not deleted, the fragment to be deleted may begin at the start codon ATG of the following gene: the Cro gene.

More preferably, said nucleic acid fragment does not comprise the coding sequence of ral, N and C2 (SEQ ID NO: 6), as well as the regulatory sequences of the promoter of C2.

The C2 gene encodes a repressor protein, which is important for maintaining the lysogenic state. This gene is also called cI in the sequence of several other lambdoid phages. In the lambda phage, the coding sequence of the ral, N and cI genes is from residues 33930 to 38040. In the lambda DE3 phage, the coding sequence of the ral, N, C2 genes is from residues 10813 to 12436.

In one embodiment, the length of said deleted nucleic acid fragment is from 30 kb to 300 b, preferably from 5 kb to 500 b. In another embodiment, the length of said deleted nucleic acid fragment is 30 kb, 25 kb, 20 kb, 15 kb, 10 kb, 9 kb, 8 kb, 7 kb, 6 kb, 5 kb, 4 kb, 3 kb, 2 kb, 1 kb, 750 b, 500 b.

According to one embodiment where the phage is lambda, the deleted nucleic acid fragment starts at a position ranging from the position 35582 to the position 45186, preferably from 38041 to 45186 and ends at a position ranging from the position 45510 to the position 48502

According to another embodiment where the phage is lambda DE3, the deleted nucleic acid fragment starts at a position ranging from the position 11392 to the position 16764, preferably from 12437 to the position 16764 and ends at a position ranging from 17088 and 42925.

In another embodiment, the nucleic acid fragment to be deleted comprises at least the coding sequence of the S and R genes. According to one embodiment, when the phage is lambda, the nucleic acid fragment starts at a position ranging from the position 35582 to the position 45186, preferably from 38041 to 45186, and ends at a position ranging from the position 45970 to the position 48502. In another embodiment, when the phage is lambda DE3, the nucleic acid fragment starts at a position ranging from the position 11392 to the position 16764, preferably from 12437 to the position 16764, and ends at a position ranging from 17548 and 42925.

In another embodiment, the nucleic acid fragment to be deleted comprises at least the coding sequence of the S, R and Rz genes. According to one embodiment, when the phage is lambda, the nucleic acid fragment starts at a position ranging from the position 35582 to the position 45186, preferably from 38041 to 45186. According to this embodiment, the fragment may end at a position ranging from the position 46428 to the position 46458. Still according to this embodiment, the nucleic acid fragment may end at a position ranging from 46128 to 48502.

According to another embodiment, when the phage is lambda DE3, the nucleic acid fragment starts at a position ranging from the position 11392 to the position 16764, preferably from 12437 to the position 16764. According to this embodiment, the fragment may end at a position ranging from position 18006 and 18036. Still according to this embodiment, the nucleic acid fragment may end at a position ranging from position 18006 to 24496. Still according to this embodiment, the nucleic acid fragment may end at a position ranging from position 18006 to 42925.

According to another embodiment, the nucleic acid fragment to be deleted comprises at least the coding sequence of the R gene.

According to one embodiment, when the phage is lambda, the nucleic acid fragment starts at a position ranging from the position 35582 to the position 45493, preferably ranging from the position 38041 to the position 45493. According to this embodiment, the nucleic acid fragment to be deleted may end at a position ranging from 45970 to the position 48502.

According to another embodiment, when the phage is lambda DE3, the nucleic acid fragment starts at a position ranging from the position 11392 to the position 17071, preferably ranging from the position 12437 to the position 17071. According to this embodiment, the nucleic acid fragment to be deleted may end at a position ranging from 17548 to the position 24496. Still according to this embodiment, the nucleic acid fragment to be deleted may end at a position ranging from 17548 to the position 42925.

According to another embodiment, the nucleic acid fragment to be deleted comprises at least the coding sequence of the R and Rz genes.

According to one embodiment, when the phage is lambda, the nucleic acid fragment starts at a position ranging from the position 35582 to the position 45493, preferably ranging from the position 38041 to the position 45493. According to this embodiment, the nucleic acid fragment to be deleted may end at a position ranging from 46428 to the position 46458. Still according to this embodiment, the nucleic acid fragment to be deleted may end at a position ranging from 46428 to the position 48502.

According to another embodiment, when the phage is lambda DE3, the nucleic acid fragment starts at a position ranging from the position 11392 to the position 17071, preferably ranging from the position 12437 to the position 17071. According to this embodiment, the nucleic acid fragment to be deleted may end at a position ranging from 18006 to the position 18330. Still according to this embodiment, the nucleic acid fragment to be deleted may end at a position ranging from 18006 to the position 24496. Still according to this embodiment, the nucleic acid fragment to be deleted may end at a position ranging from 18006 to the position 42925.

In one embodiment, the Int gene is inactivated. The Int protein manages the insertion and the excision of phage genome into the host's genome. According to an embodiment, the Int gene has the sequence SEQ ID NO: 7. In another embodiment, the sequence of the Int gene presents a sequence identity of at least 70%, at least 75%, at least 80%, at least 85%, at least 90%, at least 91%, at least 92%, at least 93%, at least 94%, at least 95%, 5 at least 96%, at least 97%, at least 98%, and even more preferably of at least 99% with SEQ ID NO: 7.

The Int gene may contain conservative sequence modifications as described here above that refer to amino acid modifications that do not significantly affect or alter the function of the Int protein. The modified sequence of the Int protein may comprise one, two, three, four or more amino acid insertions, deletions or substitutions. Thus, one or more amino acid residues within the sequence of the Int protein can be replaced with other amino acid residues from the same side chain family and the modified Int protein can be tested for retained function (i.e., the properties set forth herein) by comparison with the Int protein encoded by the sequence SEQ ID NO: 7.

In one embodiment, the Xis gene is inactivated. The Xis protein is an excisionase, which is involved in the process of excision of the lambda phage DNA out of the bacterial host chromosome. According to an embodiment, the Xis gene has the sequence SEQ ID NO: 8. In another embodiment, the sequence of the Xis gene presents a sequence identity of at least 70%, at least 75%, at least 80%, at least 85%, at least 90%, at least 91%, at least 92%, at least 93%, at least 94%, at least 95%, 5 at least 96%, at least 97%, at least 98%, and even more preferably of at least 99% with SEQ ID NO: 8.

The Xis gene may contain conservative sequence modifications as described here above that refer to amino acid modifications that do not significantly affect or alter the function of the Xis protein. The modified sequence of the Xis protein may comprise one, two, three, four or more amino acid insertions, deletions or substitutions. Thus, one or more amino acid residues within the sequence of the Xis protein can be replaced with other amino acid residues from the same side chain family and the modified Xis protein can be tested for retained function (i.e., the properties set forth herein) by comparison with the Xis protein encoded by the sequence SEQ ID NO: 8.

In one embodiment, a nucleic acid fragment comprising the coding sequence of the Int gene is deleted. According to an embodiment, the phage is lambda and the nucleic acid fragment to be deleted comprises the residues from position 27812 to 28882. According to another embodiment, the phage is lambda and the nucleic acid fragment to be deleted starts at a position ranging from position 1 to position 27812; and ends at a position ranging from 28882 to 33929.

In one embodiment, a nucleic acid fragment comprising the coding sequence of the Xis gene is deleted.

According to one embodiment, the phage is lambda and the deleted nucleic acid fragment to be deleted comprises the residues from position 28860 to 29078. According to another embodiment, the phage is lambda and the fragment starts at a position ranging from position 1 to position 28860, and ends at a position ranging from position 29078 to position 33929.

According to another embodiment, the phage is DE3 and the deleted nucleic acid comprises the residues from position 5586 to 5804. According to another embodiment, the fragment to be deleted starts at a position ranging from position 1 to position 5586, and ends at a position ranging from position 5804 to position 10812.

In one embodiment, a nucleic acid fragment comprising the coding sequences of the Xis and Int genes is deleted. According to an embodiment, the phage is lambda and the nucleic acid fragment to be deleted comprises the residues from position 27812 to 29078. According to another embodiment, the phage is lambda and the nucleic acid fragment to be deleted starts at a position ranging from position 1 to position 27812; and ends at a position ranging from 29078 to 33929.

According to an embodiment, the attP sequence is not deleted from the sequence of the phage of the invention. The attP sequence is SEQ ID NO: 9. The attP sequence is located from position 27586 and 27817 in the sequence of the Lambda Phage, and from position 42788 to 42925 and from 1 to 94 in the genome of the Lambda DE3 phage (the genome of the phage is circular, the attP sequence is thus continue).

In one embodiment of the invention, the genetically modified phage comprises the attP sequence and the sequence of the C2 gene. In another embodiment, the genetically modified phage consists of the attP sequence and the sequence of the C2 gene.

According to a preferred embodiment, the genetically modified phage of the invention has the sequence SEQ ID NO: 10.

The present invention also relates to a process for producing the modified phage of the invention, wherein said process comprises at least two steps of deletion of genes.

In an embodiment, the process of the invention is carried out with a phage integrated in the genome of a host cell.

In an embodiment, the host cell is a microorganism, preferably a prokaryote, more preferably a bacterium, more preferably a gram negative bacterium. Advantageously, the host cell is a bacterium from the Enterobacteriacea family according to the current applicable taxonomy. If the taxonomy should change, the skilled artisan would now how to adapt the changes in the taxonomy to deduce the strains that could be used in the present invention. Examples of bacteria from the Enterobacteriacea family include, but are not limited to, bacteria belonging to the genera *Escherichia, Enterobacter, Erwinia, Klebsiella, Pantoea, Photorhabdus, Providencia, Salmonella, Serratia, Shigella, Morganella* and *Yersinia*. According to a preferred embodiment, the host cell belongs to the *Escherichia* genus, and more preferably the host cell is *Escherichia coli (E. coli)*.

Methods for deleting genes from an integrated phage are well known to the skilled artisan. Examples of such methods include, but are not limited to homologous recombination (also called recombineering) using the lambda Red-encoded genes: exo, bet and gam. It is also possible to use the corresponding recE and recT genes from the prophage Rac. The genes exo and recE encode a 5'-3' exonuclease that produces 3' overhangs. The bet and recT genes encode a pairing or also called annealing protein that binds the 3' overhangs and mediates its annealing and homologous recombination between two complementary DNA sequences. The gam gene encodes an inhibitor of the *E. coli* RecBCD exonuclease and thus protects linear DNA fragments of interest. The method of recombineering was well described by several researchers including Datsenko and Wanner (PNAS 97-12, 6640-6645, 2000) and Stewart et al. (WO0104288). The principle of the method is to generate (by PCR amplification for example) a DNA fragment containing the fragment to integrate and two recombination arms. These arms are homologous to the regions adjacent to the gene to be inactivated. They will be used to target the insertion of the fragment of interest. It is possible to create this kind of DNA fragment by PCR using primers containing homologous arms from 20 to 60 nucleotides.

The present invention also relates to a host cell comprising the genetically modified phage of the invention. In a preferred embodiment, the host cell of the invention comprises the genetically modified phage integrated in its genome.

In one embodiment, the host cell is a microorganism, preferably a prokaryote, more preferably a bacterium, more preferably a gram negative bacterium. Advantageously, the host cell is a bacterium from the Enterobacteriacea family according to the current applicable taxonomy. If the taxonomy should change, the skilled artisan would now how to adapt the changes in the taxonomy to deduce the strains that could be used in the present invention. Examples of bacteria from the Enterobacteriacea family include, but are not limited to, bacteria belonging to the genera *Escherichia, Enterobacter, Erwinia, Klebsiella, Pantoea, Photorhabdus, Providencia, Salmonella, Serratia, Shigella, Morganella* and *Yersinia*. According to a preferred embodiment, the host cell belongs to the *Escherichia* genus, and more preferably the host cell is *Escherichia coli (E. coli)*. Examples of strains of *E. coli* which could be used in the present invention include, but are not limited to, strains derived from *E. coli* K-12 and *E. coli E. coli* B, such as, for example, MG1655, Top10, DH10B, DH5alpha, HMS174, BL21, BL21(DE3), BL21(DE3) pLysS, BL21(DE3) pLysE.

In one embodiment, genes of the host cells may be inactivated.

In one embodiment, the gene tonA (also known as fhuA, SEQ ID NO: 11) is inactivated. The TonA/FhuA protein is a receptor for the phages T1, T5 and Phi80.

In one embodiment, the gene galK (SEQ ID NO: 12) is inactivated. The deletion of this gene allows the use of the galK positive/negative selection for deletion of genes by a method based on homologous recombination.

In one embodiment, the gene araB (SEQ ID NO: 13) is inactivated. In another embodiment, the gene araA (SEQ ID NO: 14) is inactivated. The inactivation of araB and/or araA is required for the use of the promoter PBAD (inducible by arabinose) within the host cell.

In one embodiment, the gene lon (SEQ ID NO: 15) and/or the gene ompT (SEQ ID NO: 16) are inactivated. The Lon protein is an ATP dependent protease. The OmpT protein is an outer membrane protease. Preferably, the genes lon and ompT are inactivated.

In one embodiment, the gene rcsA (SEQ ID NO: 17) is inactivated. The protein RcsA is a positive regulator of the synthesis of the capsule, which is degraded by the Lon protease.

In one embodiment, the gene hsdR (SEQ ID NO: 18) and/or the gene mrr (SEQ ID NO: 19) are inactivated. The HsdR and Mrr proteins are restriction enzymes with different specificity. Preferably, the genes hsdR and mrr are both inactivated.

In one embodiment, the gene endA (SEQ ID NO: 20) and/or the gene recA (SEQ ID NO: 21) are inactivated. EndA is a DNA specific endonuclease. RecA is a recombination protein with protease and nuclease activity. Preferably, the genes endA and recA are both inactivated.

In one embodiment of the invention, at least one of the genes tonA, galK, araB, araA, lon, ompT, rcsA, hsdR, mrr, endA and recA are inactivated. Preferably, the inactivated genes are deleted.

In a preferred embodiment, the genes tonA, galK, araB, lon, ompT, rcsA, hsdR, mrr, endA and recA are inactivated. Preferably, the genes tonA, galK, araB, lon, ompT, rcsA, hsdR, mrr, endA and recA are deleted.

In one embodiment of the invention, the host cell of the invention is transformed with a nucleic acid sequence encoding a toxic molecule, as described in US 2004/0115811. The presence of the nucleic acid sequence encoding the toxic molecule will allow the selection of recombinant clones having integrated a gene of interest and a nucleotide sequence encoding a functional antidote protein to a toxic molecule, wherein said recombinant clones are the ones which survive following their integration into a host cell comprising in its genome a nucleotide sequence encoding said toxic molecule.

According to a preferred embodiment of the present invention, the antidote protein and the toxic molecule are respectively, an anti-poison protein and a poison protein. Said anti-poison or poison proteins could be wild type proteins or modified proteins which are naturally or artificially poisonous and affect one or more vital functions of a cell (preferably, a prokaryote cell) and may lead to the killing of the cell.

The antidote protein and the toxic molecule are preferably selected from the group consisting of CcdA/CcdB proteins, Kis/Kid proteins, Phd/Doc proteins, SoK/HoK proteins, RelB/relE proteins, PasB (or PasC)/PasA proteins, mazF/mazE proteins as described in US 2004/0115811, or any other couple of anti-poison/poison molecules which are or are not of plasmid origin. The toxic molecule can also be a toxin protein being naturally or artificially toxic and affecting one or more vital functions of a (prokaryote) cell. The protein encoded by the gene sacB (from *Bacillus amylolique-faciens*), the protein GpE, the protein GATA-1 and the protein Crp are other examples of such toxic molecules. The gene sacB encodes the levan sucrase which catalyses the hydrolysis of sucrose into products which are toxic for *E. coli* (Pierce et al. Proc. Natl. Acad. Sci., Vol. 89, N[deg.]6 (1992) p. 2056-2060). The protein GpE encodes the E genes from the bacteriophage [phi]X174 which includes six unique restriction sites and encodes gpE and which causes lysis of *E. coli* cell (Heinrich et al., Gene, Vol.

42 n[deg.]3 (1986) p. 345-349). The protein GATA-1 has been described by Trudel et al. (Biotechniques 1996, Vol. 20(4), p. 684-693). The protein Crp has been described by Schlieper et al. (Anal. Biochem. 1998, Vol. 257(2), p. 203-209).

The antidote proteins to said toxic molecule are any protein able to reduce or suppress the effect of the corresponding toxic molecule on a cell (preferably a prokaryotic cell), when said toxic molecule is produced by said cell.

According to a preferred embodiment, the host cell of the invention comprises a nucleic acid sequence encoding the protein CcdB. The ccdB gene has the sequence SEQ ID NO: 22.

The present invention also relates to a kit comprising a host cell as hereinabove described, wherein the gene encoding a poison protein is inserted, and a plasmid carrying the nucleic acid sequence of the gene encoding the anti-poison protein. The expression of the anti-poison protein in the host cell is required for maintaining the viability of the host cell. In a preferred embodiment, the poison protein is encoded by the ccdB gene, and the anti-poison protein is encoded by the ccdA gene (SEQ ID NO: 23).

According to an embodiment of the invention, the plasmid of the kit may further contain, or may be modified to further contain, the nucleic acid sequence of the biomolecule of interest.

The present invention also refers to a process for preparing a host cell as hereinabove described.

In one embodiment, the process of the invention comprises a step of infection of the host cell by a genetically modified phage according to the invention. In one embodiment of the invention, said infection step includes the use of a helper phage. In the meaning of the present invention, the term "helper phage" refers to a phage used to complement a deletion or an inactivation of another phage. The helper phage will provide the missing functions to another phage to be able to infect bacteria or to prepare phage stock. Usually, the helper phage cannot form a lysogen by itself because it is cI minus (it has no repressor and is thus virulent).

The process for infecting a host cell with a phage using a helper phage is well known in the art. The first step is the preparation of the lysates and the second one is the lysogenization. Briefly, the bacterial lysates of the helper phage are prepared using standard methods as described in "Molecular cloning: a laboratory manual", Sambrook et al (2001, ISBN 978-087969577-4) or in "Large- and Small-Scale Preparation of Bacteriophage lambda lysate and DNA", Su et al, BioTechniques 25:44-46 (July 1998). Preparation of the phage of interest is done using the same principle, after phage induction (most often using UV irradiation or any situation where a lysogen undergoes DNA damage or the SOS response of the host or Cro production) in order to launch the lytic cycle and using a helper phage to provide the missing functions. An alternative to the helper phage is the use of a plasmid encoding the missing functions.

Next, the phage lysates are mixed with the targeted bacteria and plated on LB plates in order to get lysogens (as described in lambda DE3 lysogenization kit from Novagen, User Protocol TB031 or an alternative method is described in Studier and Moffat, Journal of Molecular Biology, 1986, 189:113-130). A selection phage can be used to select specifically bacteria containing the phage of interest. This selection phage is a virulent phage having the same immunity as the phage of interest. Consequently, the selection phage is unable to form plaques or to kill bacteria lysogens for the phage of interest because this phage produces the cI repressor (also called C2 in DE3 lambda phage).

The present invention thus also relates to a kit comprising the modified phage of the invention, as hereinabove described, and a helper phage. Examples of helper phages include, but are not limited to, helper phage B10 or any other lambdoid phage with a different immunity than the phage of interest (example: phage with immunity 434, 80, . . . ). Some helper phages and their manipulations were well described in the literature including in Haldimann and Wanner (Journal of Bacteriology, 183, 6384-6393, 2001).

In one embodiment, the process for preparing a host cell of the invention further comprise a step of deletion, wherein nucleic acid sequences of the host cell are deleted. Methods for deleting the sequence of a gene are well known by the skilled artisan. The more efficient method is the homologous recombination method mediated by the lambda Red-encoded genes or the recE and recT genes from the prophage Rac. As described above, this method was well described by several researchers including Datsenko and Wanner (PNAS 97-12, 6640-6645, 2000) and Stewart et al (WO0104288). PCR products are generated using primers with 20- to 60-nt extensions that are homologous to regions adjacent to the gene to be inactivated. Since only a small amount of bacteria will effectively recombine the fragment of interest, it is necessary to have a strong selection marker to select it. Antibiotic markers can be used to select the recombinants: the modified primers are used to amplify an antibiotic resistance gene. After transformation and activation of the recombination genes, recombinant bacteria are selected on medium containing the appropriate antibiotic. In this case, the targeted gene is replaced by an antibiotic resistance gene. In order to use the same strategy for the next deletion, it is necessary to remove this antibiotic resistance gene during a second step. As described in Datsenko and Wanner, it is possible to use antibiotic resistance gene that are flanked by FRT (FLP recognition target) sites. The resistance genes are then eliminated by using a helper plasmid encoding the FLP recombinase. The antibiotic resistance gene is removed by this site-specific recombinase but this method leaves traces: one site-specific recombination site is still present after removal of the antibiotic resistance gene.

To avoid the presence of this site, more preferably, the method uses galK as a marker gene. The principle of the galK selection is described in Warming et al. (Nucleic acid research, 2005, 33(4)). This method uses galK as a positive selection marker (growth on minimal medium containing galactose) during the first recombination (insertion). The removal of this marker is performed during a second homologous recombination step. During this step, galK is used as a negative selection marker on minimal medium containing 2-deoxy-galactose (DOG). The galK gene product, galactokinase, catalyzes the first step in the galactose degradation pathway. Galactokinase also efficiently catalyzes the phosphorylation of the DOG galactose analog. The product of this reaction cannot be further metabolized, leading to the accumulation of a toxic molecule (2-deoxy-galactose-1-phosphate). The advantage of this method is to avoid the presence of specific recombination site after deletion of the targeted gene and removal of the selective marker.

The present invention also relates to a process for producing a biomolecule of interest, comprising:
cultivating a host cell comprising the genetically modified phage according to the invention and the nucleic acid sequence of the biomolecule of interest, and recovering the biomolecule of interest.

In one embodiment of the invention, the nucleic acid sequence of the biomolecule of interest is comprised within the expression system of the genetically modified phage. According to this embodiment, the production of the biomolecule of interest is direct, i.e. results from the expression of the gene of the expression system, for example by culture in a medium wherein the promoter comprised in the expression system is induced.

In another embodiment of the invention, the expression system of the genetically modified phage comprises the nucleic acid sequence of the T7 RNA polymerase under the control of a lac promoter, preferably the lacUV5 promoter. According to this embodiment, the process for producing the biomolecule of interest comprises the transformation of the host cell with a plasmid comprising the nucleic acid sequence of the biomolecule of interest under the control of a the T7 promoter. The expression from the T7 promoter is under the control of T7 RNA polymerase, which is stringently specific for the T7 promoter, i.e. the T7 promoter can only be utilized by the RNA polymerase of bacteriophage T7. When IPTG is added to the culture medium, T7 RNA polymerase is expressed by transcription from the lac promoter, and allows the expression of the biomolecule of interest.

In the meaning of the present invention, the term "T7 promoter" includes promoters that are present in the genome of bacteriophage T7, as well as consensus sequences and variants of such promoters with the ability to mediate transcription by the T7 RNA polymerase. The bacteriophage T7 contains seventeen different promoter sequences, all of which comprise a highly conserved nucleotide sequence.

According to a preferred embodiment, the plasmid comprising the nucleic acid sequence of the biomolecule of interest also comprises the nucleic acid sequence of ccdA, and the host cell comprises the sequence of ccdB integrated in its genome. Therefore, only recombinant clones containing the plasmid are propagated.

According to one embodiment, the biomolecule of interest is secreted by the host cell in the fermentation broth. According to this embodiment, the biomolecule of interest may be easily recovered from the fermentation broth.

According to another embodiment, the biomolecule of interest is not secreted by the host cell in the fermentation broth. Methods for recovering an intracellular biomolecule of interest are well-known in the art. Examples of such method include, but are not limited to, the use of trichloroacetic acid (TCA) or cracking buffer containing sodium dodecyl sulfate (SDS) to recover total cytoplasmic proteins in denaturing conditions or the use of sonication, French press or equivalent to disrupt bacteria under pressure in order to recover total cytoplasmic proteins in native (not denaturing) conditions. Next, the protein of interest can be purified using specific methods including but not limited to the use of affinity or ion exchange columns.

BRIEF DESCRIPTION OF THE DRAWINGS

FIG. 1: Picture of a SDS-Page gel colored with Coomassie blue staining, showing the production of the protein of interest. 1 and 6: size; 2: pellet [pScherry1] M11DE3 before induction; 3: pellet [pScherry1] M11DE3 after induction; 4: pellet [pScherry1] HMS174DE3 before induction; 5: pellet [pScherry1] HMS174DE3 after induction. The array is for identifying the protein of interest.

EXAMPLES

The present invention is further illustrated by the following examples.

Example 1

Deletion of the xis, exo, bet, gam, kil, cIII, N and ral Genes

Deletion of xis DNA Region and Replacement by galK

First the galK gene was amplified by polymerase chain reaction (PCR) on pGalK plasmid using the primers XisgalKstart (5' GGGGGTAAATCCCGGCGCTCATGACTTCGCCTTCTTCCCAGAATTCCTGTTGACAATTA 3', SEQ ID NO: 24) and XisgalK stop (5' GTTCTGATTATTGGAAATCTTCTTTGCCCTCCAGTGTGAGCAGCACTGTCCTGCTCCTTG 3', SEQ ID NO: 25). These primers contain at the 5' end a sequence of 40 bases identical to the DNA target (italicized). These sequences of 40 bases are the recombination arms. The 3' ends were designed to amplify the galK gene and its constitutive promoter. The DNA fragment amplified by PCR (1315 bp) targeted the genes xis, exo, bet, gam, kil and cIII (DNA fragment of 5133 bp): these genes were replaced during homologous recombination by the galK gene and its promoter. Electrocompetent bacteria carrying the T7(DE3) prophage and the pKD46 plasmid were prepared according to Datsenko and Wanner (PNAS 97-12, 6640-6645, 2000). Next, the amplified galK fragment was electroporated in these bacteria according to standard procedures (200 ng of DNA fragment was used for each electroporation). SOC medium was added and bacteria were incubated during 1 hour at 37° C. Next, bacteria were washed (centrifuged, medium removal, addition of fresh medium and resuspension) twice with M9 minimal medium (Sambrook et al (2001, ISBN 978-087969577-4)) and plated on bacterial plates containing minimal M9 medium and 1% galactose. Plates were incubated at 37° C. during 1 or 2 days.

The next step was the bacterial screening: PCR screening was performed directly on colonies using the Xis1 (5'GTCTTCAAGTGGAGCATCAG3', SEQ ID NO: 26) and Xis4 (5'ACCAGGACTATCCGTATGAC3', SEQ ID NO: 27) primers. An amplification of a 5774 bp DNA fragment corresponds to a non-modified chromosome (non-recombinant colony) and, on the contrary, an amplification of a 1955 bp DNA fragment corresponds to a recombinant chromosome. Bacteria allowing amplification of the 1955 bp DNA fragment were selected and streaked two times on selective plates (minimal M9 medium supplemented with 1% galactose) in order to purify it and to remove possible unmodified copies of the chromosome. The PCR screening was done one more time at the end of the purification step and 3 bacteria allowing amplification of the 1955 bp DNA fragment were selected. The amplified DNA fragments corresponding to these bacteria were sequenced using the same primers in order to confirm the DNA recombination and the deletion of the Xis DNA region (xis, exo, bet, gam, kil and cIII genes).

GalK Removal

A DNA fragment containing large recombination arms (of 350 bp and 343 bp) was constructed by PCR to remove galK and the N and ral genes. The first arm was amplified by PCR on bacterial colonies containing the T7(DE3) prophage using the Xis1 and Xis2 (5'CCAAACGGAACAGATGAAGAAGGCGAAGTCATGAC3', SEQ ID NO: 28) primers. A DNA fragment of 365 bases was amplified. The second arm was also performed by PCR on the same bacteria using the Xis3 (5' GACTTCGCCTTCTTCATCTGTTC-CGTTTGGCTTCC3', SEQ ID NO: 29) and Xis6 (5' GTAATGGAAAGCTGGTAGTCG3', SEQ ID NO: 30) primers. A DNA of fragment of 358 bases was amplified. Both recombination arms were purified after agarose gel electrophoresis. Xis2 and Xis3 primers were designed to generate DNA fragments containing an identical sequence of 30 base pairs. This sequence was used to join both recombination arms in a third PCR using Xis1 and Xis6 primers. A DNA fragment of 693 bp was generated. This DNA fragment was electroporated in bacteria selected above and carrying the pKD46 plasmid (prepared as described in Datsenko and Wanner). SOC medium was added and bacteria were incubated at 37° C. during 1 hour. Next, bacteria were washed twice with M9 medium and plated on selective plates containing M9 medium supplemented with 0.2% glycerol and 1% DOG. Plates were incubated during 2 days at 37° C. Several colonies were screened by PCR using the Xis S (5' CAGCCGTAAGTCTTGATCTC3', SEQ ID NO: 31) and Xis7 (5'CAGCAGGCATGATCCAAGAG3', SEQ ID NO: 32) primers. An amplification of 3246 bp corresponding to the unmodified DNA chromosome was always obtained instead of an amplification of 1122 bp corresponding to the modified chromosome. The experiment was reproduced completely and independently three times without success: no bacteria comprising the desired deletion was obtained.

Consequently, we decided to remove only the GalK fragment and to leave the N and ral genes. The DNA fragment containing the recombination arms was generated as described above using Xis,1 Xis2b (5' TTTGCCCTCCA-GTGTGAAGAAGGCGAAGTCATGAG3', SEQ ID NO: 33) for the first recombination arm (365 bp) and Xis8 (5' CTCATGACTTCGCCTTCTTCACACTG-GAGGGCAAAGAAG, SEQ ID NO: 34) and Xis4 for the second recombination arm (384 bp). The joining PCR was performed using Xis1 and Xis4 primers and generated a DNA fragment of 714 bp. This fragment was electroporated as described above in the bacteria selected and carrying the pKD46 plasmid. Bacteria were plated on the same selective plates containing DOG and incubated during two days at 37° C. PCR screening was performed using Xis5 and Xis6 primers. Bacteria showing an amplification of 1770 bp (instead of an amplification of 3010 bp corresponding to the unmodified chromosome) were selected and purified. The DNA fragment was sequenced using the Xis5 and Xis6 primers and showed the right removal of the galK gene. This recombination was performed only once since bacteria were obtained immediately.

These results show that it was not possible to remove galK associated to the N and ral genes using homologous recombination. However, using exactly the same procedure, we were able to remove galK alone.

In conclusion, we demonstrated that removal of the N and ral genes leads to the death of bacteria, which was unexpected.

Example 2

Protein Expression

In order to test the protein production efficiency of the strain constructed according to the invention, small-scale expression test were performed using bacteria called M11 (DE3). The genotype of this strain is MG1655 ΔgalK, ΔrcsA, Δlon, ΔhsdR-mrr, ΔfhuA, ΔendA, ΔrecA, ΔaraB, ΔompT, λ-DE3 (T7pol, Δxis-ea10, ΔS-C). Since MG1655 is an *Escherichia coli* K-12, it was compared to another K-12 strain used as a standard in the field of protein production and called HSM174(DE3) (genotype: recA1, hsdR, λ-DE3, (Rif R)). Both strains were transformed with pSCherry1 plasmid DNA (Delphi Genetics, Belgium). This plasmid encodes a protein called "cherry" easily detectable (by eyes) under the control of the T7 promoter.

Protocol for a Small-Scale Expression Using IPTG:
1) Two Erlenmeyer flasks containing 10 ml of LB medium were inoculated each with a single colony of the HMS174 (DE3) and the M11(DE3) carrying both the pSCherry1 plasmid and incubated at 30° C. overnight.
2) Two new flasks containing fresh medium were inoculated with 1 ml of the overnight cultures and incubated with shaking at 37° C. until OD600 reached 0.6.
3) A sample (1 ml) from each flask was taken and centrifuged. The medium was discarded and the pellet was kept on ice. The samples were the non-induced controls. To induce protein expression in the remaining culture, IPTG (Isopropyl β-D-1-thiogalactopyranoside, 90 μl of a fresh 100 mM stock solution) was added to reach a final concentration of 1 mM in both flasks. Incubation of both flasks was continued for 4 hours.
4) At the end of the induction period, the Optical Density at 600 nm was measured for each culture (1.09 for M11(DE3) and 1.13 for HMS174 (DE3)). A 1 ml sample of each flask was centrifuged at maximum speed (13000 g) for 10 min at 4° C. It was observed that the pellet was red according to the expression of the Cherry protein. The supernatant was discarded and 100 μl of water was added to resuspend the bacteria. 100 μl of "cracking" buffer (100 mM DTT, 2% SDS, 80 mM Tris-HCl, pH 6.8, 0.006% bromophenol blue, 15% glycerol) was also added to lyse the bacteria. The non-induced samples were treated with the same protocol except that only 60 μl of water and 60 μl of cracking buffer were used (according to the optical density of the samples).
5) The samples were heated at 70° C.-100° C. (10 min.) to resuspend all proteins and to denature the proteins.
6) 10 μl of each sample was loaded on 12% SDS-PAGE gel and migrated during 2 hours at 100 Volt.
7) After migration, the proteins were colored with Coomassie-blue staining.

As shown on FIG. 1, both strains were able to produce the protein of interest (Cherry protein, indicated by the array) but the production is about 5 to 10 times higher using M11(DE3) than using HMS174(DE3). The experiment was performed twice with exactly the same results.

The invention claimed is:

1. A lambda phage, comprising the sequence of SEQ ID NO: 35 or a sequence that is at least 90% identical, wherein the lambda phage is modified by:
   insertion of a T7 expression system; and
   deletion of the S and R genes, wherein the S gene corresponds to SEQ ID NO:1 (wildtype S gene) or to a sequence which is at least 90% identical to SEQ ID NO: 1, wherein the R gene corresponds to SEQ ID NO:2 (wildtype R gene) or to a sequence which is at least 90% identical to SEQ ID NO: 2 and wherein the deletion of the S and R genes reduce the ability of the phage to regain its lytic properties.

2. The lambda phage of claim 1, further comprising at least one deleted Int gene or deleted Xis gene; wherein the Int gene corresponds to SEQ ID NO:7 (wildtype Int gene) or to a sequence which is at least 90% identical to SEQ ID NO:7 wherein the Xis gene corresponds to SEQ ID NO:8 (wildtype Xis gene) or a sequence which is at least 90% identical to SEQ ID NO:8, and wherein the deletion of the Int and/or Xis gene reduces the ability of the phage to excise itself.

3. The lambda phage of claim 1, further comprising at least one deleted Int gene, Xis gene or Rz gene wherein the Int gene corresponds to SEQ ID NO:7 (wildtype Int gene) or to a sequence which is at least 90% identical to SEQ ID NO:7, wherein the Xis gene corresponds to SEQ ID NO:8 (wildtype Xis gene) or a sequence which is at least 90% identical to SEQ ID NO:8, wherein the Rz gene corresponds to SEQ ID NO:3 (wildtype Rz gene) or a sequence which is at least 90% identical to SEQ ID NO:3, wherein the deletion of the Rz gene reduces the ability of the phage to regain its lytic properties, and wherein the deletion of the Int and/or Xis gene reduces the ability of the phage to excise itself.

4. The lambda phage of claim 1, further comprising deleted Int gene, deleted Xis gene, and deleted Rz gene, wherein the Int gene corresponds to SEQ ID NO:7 (wildtype Int gene) or to a sequence which is at least 90% identical to SEQ ID NO:7, wherein the Xis gene corresponds to SEQ ID NO:8 (wildtype Xis gene) or a sequence which is at least 90% identical to SEQ ID NO:8, wherein the Rz gene corresponds to SEQ ID NO:3 (wildtype Rz gene) or a sequence which is at least 90% identical to SEQ ID NO:3, wherein the deletion of the Rz gene reduces the ability of the phage to regain its lytic properties, and wherein the deletion of the Int and Xis genes reduces the ability of the phage to excise itself.

5. The lambda phage of claim 1, comprising a sequence of SEQ ID NO: 10.

6. A host cell comprising the lambda phage of claim 1.

7. The host cell of claim 6, wherein the lambda phage comprises at least one deleted Int gene, Xis gene or Rz gene, wherein the deletion of the Rz gene reduces the ability of the phage to regain its lytic properties, wherein the deletion of the Int and/or Xis gene reduces the ability of the phage to excise itself wherein the Int gene corresponds to SEQ ID NO:7 (wildtype Int gene) or to a sequence which is at least 90% identical to SEQ ID NO:7, wherein the Xis gene corresponds to SEQ ID NO:8 (wildtype Xis gene) or a sequence which is at least 90% identical to SEQ ID NO:8, and wherein the Rz gene corresponds to SEQ ID NO:3 (wildtype Rz gene) or a sequence which is at least 90% identical to SEQ ID NO:3.

8. The host cell of claim 6, wherein the lambda phage comprises a deleted Int gene, deleted Xis gene, and deleted Rz gene, wherein the Int gene corresponds to SEQ ID NO:7 (wildtype Int gene) or to a sequence which is at least 90% identical to SEQ ID NO:7, wherein the Xis gene corresponds to SEQ ID NO:8 (wildtype Xis gene) or a sequence which is at least 90% identical to SEQ ID NO:8, wherein the Rz gene corresponds to SEQ ID NO:3 (wildtype Rz gene) or a sequence which is at least 90% identical to SEQ ID NO:3, wherein the deletion of the Rz gene reduces the ability of the phage to regain its lytic properties, and wherein the deletion of the Int and Xis genes reduces the ability of the phage to excise itself.

9. The host cell of claim 6, wherein the lambda phage comprises a sequence of SEQ ID NO: 10.

10. The host cell of claim 6, wherein the host cell is an enterobacteria.

11. The host cell of claim 10, wherein the enterobacteria is *Escherichia coli*.

12. The host cell of claim 6, further comprising at least one inactivated tonA, galK, araB, araA, ion, ompT, rcsA, hsdR, mrr, endA, or recA gene.

13. The host cell of claim 6, comprising an inserted ccdb gene.

14. A process for preparing the host cell of claim 6, comprising infecting the host cell with a lambda phage comprising the sequence of SEQ ID NO: 35 or a sequence that is at least 90% identical to SEQ ID NO: 35,
wherein the lambda phage is modified by:
    insertion of a T7 expression system; and
    deletion of the S and R genes, wherein the S gene corresponds to SEQ ID NO:1 (wildtype S gene) or to a sequence which is at least 90% identical to SEQ ID NO: 1 wherein the R gene corresponds to SEQ ID NO:2 (wildtype R gene) or to a sequence which is at least 90% identical to SEQ ID NO: 2, and
wherein the deletion of the S and R genes reduces the ability of the phage to regain its lytic properties.

15. The lambda phage of claim 1, wherein the lambda phage further comprises a T7 RNA polymerase.

* * * * *